United States Patent
Uhrich et al.

(10) Patent No.: US 10,759,740 B2
(45) Date of Patent: Sep. 1, 2020

(54) ANTIBACTERIAL AGENTS

(71) Applicant: Rutgers, The State University of New Jersey, New Brunswick, NJ (US)

(72) Inventors: Kathryn Uhrich, Riverside, CA (US); Yingyue Zhang, New Brunswick, NJ (US); Allison Faig, New Brunswick, NJ (US); Michael Chikindas, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 16/086,927

(22) PCT Filed: Mar. 24, 2017

(86) PCT No.: PCT/US2017/024125
§ 371 (c)(1),
(2) Date: Sep. 20, 2018

(87) PCT Pub. No.: WO2017/165836
PCT Pub. Date: Sep. 28, 2017

(65) Prior Publication Data
US 2019/0161436 A1 May 30, 2019

Related U.S. Application Data

(60) Provisional application No. 62/312,588, filed on Mar. 24, 2016.

(51) Int. Cl.
| | |
|---|---|
| C07C 235/10 | (2006.01) |
| A61K 31/23 | (2006.01) |
| A61K 31/7036 | (2006.01) |
| A61K 31/4164 | (2006.01) |
| A61K 31/4168 | (2006.01) |
| A61P 31/04 | (2006.01) |
| C07C 235/06 | (2006.01) |
| A61K 45/06 | (2006.01) |
| A61K 31/164 | (2006.01) |
| A61K 31/7056 | (2006.01) |

(52) U.S. Cl.
CPC .......... *C07C 235/10* (2013.01); *A61K 31/164* (2013.01); *A61K 31/23* (2013.01); *A61K 31/4164* (2013.01); *A61K 31/4168* (2013.01); *A61K 31/7036* (2013.01); *A61K 31/7056* (2013.01); *A61K 45/06* (2013.01); *A61P 31/04* (2018.01); *C07C 235/06* (2013.01)

(58) Field of Classification Search
None
See application file for complete search history.

(56) References Cited

U.S. PATENT DOCUMENTS

| | | | |
|---|---|---|---|
| 4,065,598 A | 12/1977 | Takahashi et al. |
| 4,559,157 A | 12/1985 | Smith et al. |
| 4,608,392 A | 8/1986 | Jacquet et al. |
| 4,820,508 A | 4/1989 | Wortzman |
| 4,938,949 A | 7/1990 | Borch et al. |
| 4,992,478 A | 2/1991 | Geria |
| 6,328,988 B1 | 12/2001 | Uhrich et al. |
| 6,365,146 B1 | 4/2002 | Uhrich et al. |
| 6,497,895 B2 | 12/2002 | Uhrich et al. |
| 7,262,221 B2 | 8/2007 | Uhrich et al. |
| 7,470,802 B2 | 12/2008 | Uhrich et al. |
| 8,192,754 B2 | 6/2012 | Uhrich et al. |
| 8,846,850 B2 | 9/2014 | Uhrich et al. |

(Continued)

FOREIGN PATENT DOCUMENTS

| | | |
|---|---|---|
| JP | 04326209 | 12/1992 |
| WO | 2000065024 A2 | 11/2000 |

(Continued)

OTHER PUBLICATIONS

Chemical Abstract Registry No. 252571-18-9, indexed in the Registry File on STN CAS Online Jan. 10, 2000.*

(Continued)

*Primary Examiner* — Po-Chih Chen
(74) *Attorney, Agent, or Firm* — Viksnins Harris Padys Malen LLP

(57) ABSTRACT

The invention provides an antibacterial compound of formula (I) or a salt thereof, as well as an antibacterial compound of formula (II) or a salt thereof, wherein $R^1$, $R^2$, W, X, Y and n have any of the values defined in the specification.

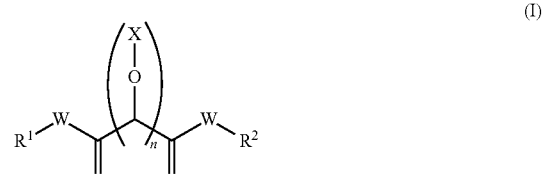

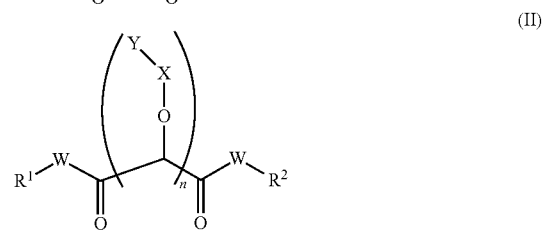

46 Claims, 15 Drawing Sheets

(56) References Cited

U.S. PATENT DOCUMENTS

| | | | |
|---|---|---|---|
| 9,434,681 | B2 | 9/2016 | Uhrich et al. |
| 9,630,905 | B2 | 4/2017 | Uhrich et al. |
| 10,138,203 | B2 * | 11/2018 | Uhrich ............... A61K 9/1272 |
| 2004/0198641 | A1 | 10/2004 | Uhrich et al. |
| 2005/0089504 | A1 | 4/2005 | Uhrich et al. |
| 2008/0057026 | A1 | 3/2008 | Uhrich et al. |
| 2009/0175932 | A1 | 7/2009 | Uhrich et al. |
| 2011/0008396 | A1 | 1/2011 | Moghe et al. |
| 2011/0229416 | A1 | 9/2011 | Uhrich et al. |
| 2012/0022159 | A1 | 1/2012 | Uhrich et al. |
| 2012/0039983 | A1 | 2/2012 | Uhrich et al. |
| 2012/0219598 | A1 | 8/2012 | Uhrich et al. |
| 2012/0225926 | A1 | 9/2012 | Uhrich et al. |
| 2013/0005785 | A1 | 1/2013 | Nordsiek et al. |
| 2018/0037840 | A1 | 2/2018 | Uhrich et al. |
| 2019/0119199 | A1 | 4/2019 | Uhrich et al. |

FOREIGN PATENT DOCUMENTS

| | | | |
|---|---|---|---|
| WO | 2001005873 | A1 | 1/2001 |
| WO | 2003005959 | A2 | 1/2003 |
| WO | 2003047518 | A2 | 6/2003 |
| WO | 2003103594 | A2 | 12/2003 |
| WO | 2005074887 | A2 | 8/2005 |
| WO | 2009039505 | A1 | 3/2009 |
| WO | 2013188882 | A1 | 12/2013 |
| WO | 2015191742 | A1 | 12/2015 |
| WO | 2015195563 | A1 | 12/2015 |
| WO | 2018027227 | A1 | 2/2018 |

OTHER PUBLICATIONS

Ito et al. A medium-term rat liver bioassay for rapid in vivo detection of carcinogenic potential of chemicals. Cancer Science, 2003, 94, 3-8.*

Abstract of "Edwin et al., The Use and Abuse of the Broad Spectrum Antibiotics. JAMA, 1963, 185, 273-279".*

Lebreton et al., Structure-Immunosuppressive Activity Relationships of New Analogues of 15-Deoxyspergualin. 1. Structural Modification of the Hydroxyglycine Moiety. Journal of Medicinal Chemistry, 1999, 42, 277-290.*

Algburi, A , et al., "Gemini Cationic Amphiphiles Control Biofilm Formation by Bacterial Vaginosis Pathogens", Antimicrob Agents Chemother 61(12), e00650-17, 13 pages (2017).

Allen, C. , et al., "Nano-engineering block copolymer aggregates for drug delivery", Colloids and Surfaces B: Biointerfaces 16, 3-27 (1999).

Amara, N , et al., "Covalent Inhibition of Bacterial Quorum Sensing", J Am Chem Soc 131(30), 10610-10619 (2009).

Binder, H , et al., "Charge-dependent translocation of the Trojan peptide penetratin across lipid membranes", Biophys J 85(2), 982-995 (2003).

Boucher, H , et al., "Bad bugs, no drugs: no ESKAPE! An update from the Infectious Diseases Society of America", Clin Infect Dis 48(1), 1-12 (2009).

Breukink, E , et al., "Binding of Nisin Z to bilayer vesicles as determined with isothermal titration calorimetry", Biochemistry 39(33), 10247-10254 (2000).

Brogden, K , "Antimicrobial peptides: pore formers or metabolic inhibitors in bacteria?", Nature Reviews Microbiology 3, 238-250 (2005).

Buijnsters, P , et al., "Cationic Gemini Surfactants Based on Tartaric Acid: Synthesis, Aggregation, Monolayer Behaviour, and Interaction with DNA", Eur J Org Chem, 1397-1406 (2002).

Calvez, P , et al., "Parameters modulating the maximum insertion pressure of proteins and peptides in lipid monolayers", Biochimie 91(5), 718-733 (2009).

Camejo , et al., "The extracellular matrix on atherogenesis and diabetes-associated vascular disease", Atherosclerosis Supplements 3, 3-9 (2002).

Cammas , et al., "Functional poly[(ethylene oxide)—co-(□-benzyl-L-aspartate)] polymeric micelles: block copolymer synthesis and micelles formation", Macromol. Chem. Phys., 196, 1899-1905 (1995).

Chemical Abstract of , JP-6305820, 1994.

Chnari, E. , et al., "Engineered polymeric nanoparticles for receptor-targeted blockage of oxidized low density lipoprotein uptake and atherogenesis in macrophages", Biomacromolecules 7(6), 1796-1805 (2006).

Chnari, E. , et al., "Nanoscale anionic macromolecules can inhibit cellular uptake of differentially oxidized LDL", Biomacromolecules 7 (2), 597-603 (2006).

Chnari, E. , et al., "Nanoscale anionic macromolecules for selective retention of low-density lipoproteins", Biomaterials 26 (17), 3749-3758 (2005).

Djodjevic , et al., "Polymeric Micelles Based on Amphiphilic Scorpion-like Macromolecules: Novel Carriers for Water-Insoluble Drugs", Pharmaceutical Research, 22(1), 24-32 (2005).

Djordjevic, J , et al., "Amphiphilic Scorpion-like Macromolecules as Micellar Nanocarriers", Journal of Bioactive and Compatible Polymers, vol. 23 (6), 532-551 (2008).

Djordjevic , et al., "Amphiphilic Star-Like Macromolecules as Novel Carriers for Topical Delivery of Nonsteroidal Anti-Inflammatory Drugs", AAPS PharmSci, 5 (4), 1-12, 2003.

Domingues, T , et al., "Interaction of the antimicrobial peptide gomesin with model membranes: a calorimetric study", Langmuir 29, 8609-8618 (2013).

Dubertret, B , et al., "In vivo Imaging of Quantum Dots Encapsulated in Phospholipid Micelles", Science 298, 1759-1762 (2002).

Epand, R , et al., "Dual mechanism of bacterial lethality for a cationic sequence-random copolymer that mimics host-defense antimicrobial peptides", J Mol Biol 379(1), 38-50 (2008).

Faig, A , et al., "Biscationic Tartaric Acid-Based Amphiphiles: Charge Location Impacts Antimicrobial Activity", Langmuir 31(43), 11875-1185 (2015).

Faig, A , et al., "Cationic amphiphiles as disruptive antimicrobial agents", Abstract No. 434, 248th ACS National Meeting & Exposition, San Francisco, California, 1 page, (Jun. 16, 2014).

Faig, A , et al. "Cationic amphiphiles as disruptive antimicrobial agents", Poster, 248th ACS National Meeting & Exposition, San Francisco, California (Aug. 2014).

Faig, A , "Design, Synthesis, and Characterization of Bioactive Amphiphiles for Therapeutic Applications", Dissertation Defense Presentation, Rutgers, the State University of New Jersey, 37 pages, (Apr. 2015).

Faig, A, "Design, Synthesis, and Characterization of Bioactive Amphiphiles for Therapeutic Applications", Dissertation, Rutgers, the State University of New Jersey, 171 pages, (Oct. 2015).

Gabriel, G , et al., "Interactions between antimicrobial polynorbornenes and phospholipid vesicles monitored by light scattering and microcalorimetry", Langmuir 24(21), 12489-12495 (2008).

Gabriel, G , et al., "Synthetic mimic of antimicrobial peptide with nonmembrane-disrupting antibacterial properties", Biomacromolecules 9, 2980-2983 (2008).

Gao , et al., "A model of micellization for block copolymers in solutions", Macromolecules 26, 7353-7360 (1993).

Gitsov , et al., "Micelles with highly branched nanoporous interior: solution properties and binding capabilities of amphiphilic copolymers with linear dendritic architecture", Journal of Polymer Science: Part A: Polymer Chemistry 38, 2711-2727 (2000).

Grenier, M , et al., "The antibacterial activity of 4,4'-bipyridinium amphiphiles with conventional, bicephalic and gemini architectures", Bioorganic & Medicinal Chemistry Letters 22(12), 4055-4058 (2012).

Hancock, R , et al., "Antimicrobial and host-defense peptides as new anti-infective therapeutic strategies", Nature Biotechnology 24, 1551-1557 (2006).

Harmon , et al., "In Vitro Evaluation of Amphiphilic Macromolecular Nanocarriers for Systemic Drug Delivery", Journal of Bioactive and Compatible Polymers 24, 185-197 (2009).

(56) References Cited

OTHER PUBLICATIONS

Iverson, N , et al., "Controllable inhibition of cellular uptake of oxidized low-density lipoprotein: Structure-function relationships for nanoscale amphiphilic polymers", Acta Biomaterialia 6, 3081-3091 (2010).
Karlsson, L , et al., "Compaction of DNA by Gemini Surfactants: Effects of Surfactant Architecture", Journal of Colloid and Interface Science 252, 290-296 (2002).
Kataoka, K. , et al., "Block copolymer micelles for drug delivery: design, characterization and biological significance", Adv Drug Deliv Rev. 47(1), 113-31 (2001).
Kennedy, M , et al., "Determinants of Calcineurin Binding to Model Membranes", Biochemistry 36(44), 3579-13585 (1997).
Klancnik, A , et al., "Evaluation of Diffusion and Dilution Methods to Determine the Antibacterial Activity of Plant Extracts", J Microbiol Methods 81(2), 121-126 (2010).
Kleinschmidt, J , et al., "Structural transitions in short-chain lipid assemblies studied by (31)P-NMR spectroscopy", Biophys J 83(2), 994-1003 (2002).
Kreig , et al., "Micelle formation of randomly grafted copolymers in slightly selective solvents", Journal of Chemical Physics 115(13), 6243-6251 (2001).
Ladow, J , et al., "Bicephalic amphiphile architecture affects antibacterial activity", European Journal of Medicinal Chemistry 46, 4219-4226 (2011).
Langer, R. , et al., "New methods of drug delivery", Science, 249, pp. 1527-1533, 1990.
Laverty, G , et al., "The potential of antimicrobial peptides as biocides", International Journal of Molecular Sciences 12, 6566-6596 (2011).
Ling, L , et al., "A new antibiotic kills pathogens without detectable resistance", Nature 517(7535), 455-459 (2015).
Ling, L , et al., "Erratum: A new antibiotic kills pathogens without detectable resistance", Nature 520(7547), 388 (2015).
Liu, D , et al., "Nontoxic membrane-active antimicrobial arylamide oligomers", Angewandte Chemie-International Edition 43, 1158-1162 (2004).
Liu , et al., "Unimolecular micelles: Synthesis and characterization of amphiphilic polymer systems", Journal of Polymer Science, Part A:P Polymer Chemistry, 37(6), 703-711 (1999).
Livne, L , et al., "Design and characterization of a broad-spectrum bactericidal acyl-lysyl oligomer", Chemistry Biology 16, 1250-1258 (2009).
Martin, V , et al., "Colloidal and biological properties of cationic single-chain and dimeric surfactants", Colloids and Surfaces B: Biointerfaces 114, 247-254 (2014).
Moghimi, S. M., et al., "Exploiting bone marrow microvascular structure for drug delivery and future therapies", Advanced Drug Delivery Reviews 17, 61-73 (1995).
Moghimi, S. M., et al., "Long-Circulating and Target-Specific Nanoparticles: Theory to Practice", Pharmacological Reviews 53, 283-318 (2001).
Mondal, D , et al., "Synthesis and antibacterial properties of carbohydrate-templated lysine surfactants", Carbohydrate Research 346, 588-594 (2011).
Moore, Jeffrey S., et al., "Room temperature polyesterification", Macromolecules 23 (1), 65-70 (1990).
Orwig, K , et al., "Comparison of N-terminal modifications on neurotensin(8-13) analogues correlates peptide stability but not binding affinity with in vivo efficacy", J Med Chem 52(7), 1803-1813 (2009).
O'Toole, G , et al., "Diphosphonium Ionic Liquids as Broad Spectrum Antimicrobial Agents", Cornea 31(7), 810-816 (2012).
Otsuka, H. , et al., "Self-assembly of poly(ethylene glycol)-based block copolymers for biomedical applications", Current Opinion in Colloid & Interface Science 6(1), 3-10 (2001).
Palermo, E , et al., "Cationic Spacer Arm Design Strategy for Control of Antimicrobial Activity and Conformation of Amphiphilic Methacrylate Random Copolymers", Biomacromolecules 13(5), 1632-1641 (2012).
Papisov, M.I., et al., "Modeling in vivo transfer of long-circulating polymers (two classes of long circulating polymers and factors affecting their transfer in vivo)", Advanced Drug Delivery Reviews 16, 127-139 (1995).
Park, S , et al., "The role of antimicrobial peptides in preventing multidrug-resistant bacterial infections and biofilm formation", International Journal of Molecular Sciences 12, 5971-5992 (2011).
Paslay, L , et al., "Antimicrobial poly(methacrylamide) derivatives prepared via aqueous RAFT polymerization exhibit biocidal efficiency dependent upon cation structure", Biomacromolecules 13, 2472-2482 (2012).
Patent Cooperation Treaty, International Searching Authority, Search Report and Written Opinion for PCT/US2017/024125, 19 pages, dated Jun. 19, 2017.
Poree, D , et al., "Nanoscale Amphiphilic Macromolecules with Variable Lipophilicity and Stereochemistry Modulate Inhibition of Oxidized Low-Density Lipoprotein Uptake", Biomacromolecules 14 (8), 2463-2469 (2013).
Rousselle , et al., "New advances in the transport of doxorubicin through the blood-brain barrier by a peptide vector-mediated strategy", Molecular Pharmacology 57, 679-686 (2000).
Sahl, H , "Antimicrobial and host-defense peptides as new anti-infective therapeutic strategies", Nature Biotechnology 24, 1551-1557 (2006).
Schmalenberg , et al., "Cytotoxicity of a unimolecular polymeric micelle and its degradation products", Biomacromolecules 2, 851-855 (2001).
Scorciapino, M , et al., "A novel dendrimeric peptide with antimicrobial properties: structure-function analysis of SB056", Biophys J 102, 1039-1048 (2012).
Seelig, J , "Thermodynamics of lipid-peptide interactions", Biochim Biophys Acta 1666(1-2), 40-50 (2004).
Seelig, J , "Titration calorimetry of lipid-peptide interactions", Biochim Biophys Acta 1331(1), 103-116 (1997).
Sparks , "Design, Synthesis, and Utility of Functionalized Nanoscale Amphiphilic Macromolecules for Biomedical Applications", Dissertation, Rutgers, the State University of New Jersey, 198 pages, (2011).
Sparks, S , et al., "Synthesis of Functionalized Amphiphilic Scorpion-like Macromolecules for Biomedical Applications", Polymeric Mater: Science & Engineering 97,695 (2007).
Tao, L. , et al., "Novel amphiphilic macromolecules and their in vitro characterization as stabilized micellar drug delivery systems", J. Colloid Interface Sci 298 (1), 102-110 (2006).
Temsamani , et al., "Brain drug delivery technologies: novel approaches for transporting therapeutics", PSTT 3(5), 155-162 (2000).
Tew, G , et al., "De Novo Design of Antimicrobial Polymers, Foldamers, and Small Molecules: From Discovery to Practical Applications", Acc Chem Res 43(1), 30-39 (2010).
Tian, Lu , et al., "Amphiphilic Scorpion-like Macromolecules: Design, Synthesis and Characterization", Macromolecules 37, 538-543 (2004).
Tian , et al., "Design and synthesis of amphiphilic poly(ethylene glycol) derivaties as a micellar drug delivery system", Polymer Preprints, 43(2), 719-720 (2002).
Tian , et al., "Design and synthesis of amphiphilic poly(ethylene glycol) derivatives as a micellar drug delivery system", Abstracts of Papers, Part 2, 224, (1-2), abstract 748, 224th ACS National Meeting (2002).
Tian , et al., "Novel amphiphilic macromolecules for drug delivery applications: design, synthesis and characterization", in Dissertation, New Brunswick, New Jersey, pp. 13-48, 114-138 and 160-175, 2004.
Torchilin, V.P. , et al., "Structure and design of polymeric surfactant-based drug delivery systems", J Control Release 73(2-3), 137-172 (2001).
Tounsi, N , et al., "Thermodynamic and spectroscopic studies of copper (II) complexes with three bis(amide) ligands derived from l-tartaric acid", Journal of Inorganic Biochemistry 99(12), 2423-2435 (2005).
Tuzar , et al., "Micelles of Block and Graft Copolymers in Solutions", Surface and Colloid Science 15, 1-83 (1993).

(56) References Cited

OTHER PUBLICATIONS

Wang, et al., "Comparison of PEG chain length and density on amphiphilic macromolecular nanocarriers: Self-assembled and unimolecular micelles", Acta Biomaterialia 5, 883-892 (2009).

Wang, et al., "Nanoscale amphiphilic macromolecules as lipoprotein inhibitors: the role of charge and architecture", Int. J. Nanomedicine 2(4), 697-705 (2007).

Williams, et al., "The response-to-retention hypothesis of early atherogenesis", Arteriosclerosis, Thrombosis & Vascular Biology 15(5), 551-561 (1995).

Wu, R, et al., "Functionalized Polycarbonate Derived From Tartaric Acid: Enzymatic Ring-Opening Polymerization of a Seven-Membered Cyclic Carbonate", Biomacromolecules 9(10), 2921-2928 (2008).

Zhang, T, et al., "Cardiolipin Prevents Membrane Translocation and Permeabilization by Daptomycin", Journal of Biological Chemistry 289, 11584-11591 (2014).

Zhang, Y, "Design, synthesis and characterization of amphiphiles for biomedical applications", Princeton, 11 pages, (Mar. 29, 2016).

Zhang, Y, et al. "Self-assembled cationic amphiphiles as antimicrobial peptide mimics", National ACS Meeting, Philadelphia, PA, 5 pages, Aug. 2016.

Zhang, et al., "Self-assembled cationic amphiphiles as antimicrobial peptides mimics with potent antimicrobial activity and high selectivity", Coll 122 Poster Abstract, 252nd ACS National Meeting, Philadelphia, PA, 2 pages (Jun. 2016).

Zhang, Y, et al., "Self-assembled cationic amphiphiles as antimicrobial peptides mimics: Role of hydrophobicity, linkage type, and assembly state", Nanomedicine 13(2), 343-352 (2017).

Zhang, Y, et al., "Synthesis and antibacterial characterization of gemini surfactant monomers and copolymers", Polymer Chem 3, 907-913 (2012).

Zhao, Y, "Facial amphiphiles in molecular recognition: From unusual aggregates to solvophobically driven foldamers", Current Opinion in Colloid & Interface Science 12(2), 92-97 (2007).

Zhu, et al., "Super Microcapsules" (SMC. I. Preparation and Characterization of Star Polyethylene Oxide (POE)-Polylactide (PLA) Copolymers, J. Polym. Sci. Polm. Chem. 27, 2151 (1989).

U.S. Appl. No. 16/164,517, 2019-0119199.

* cited by examiner

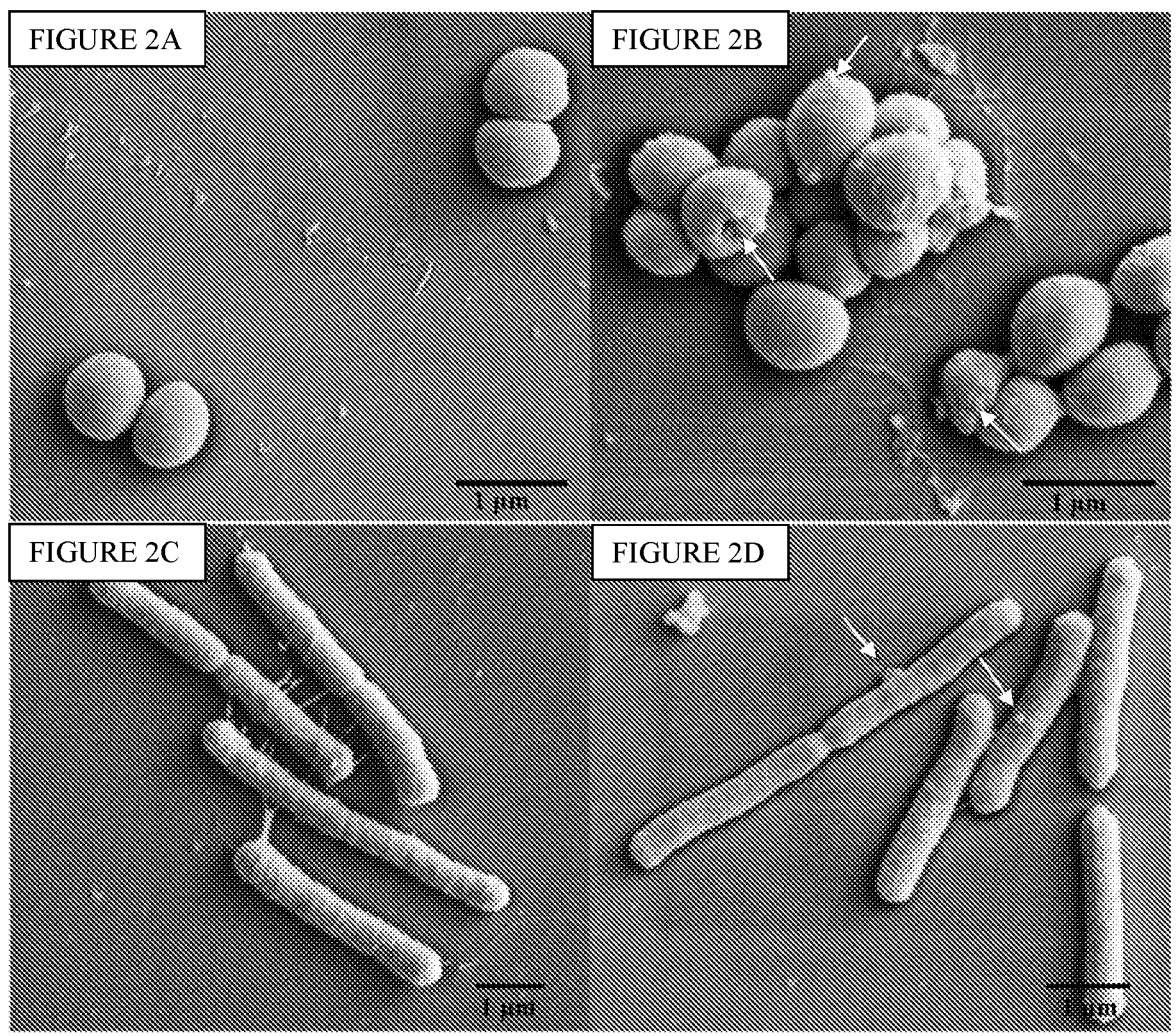

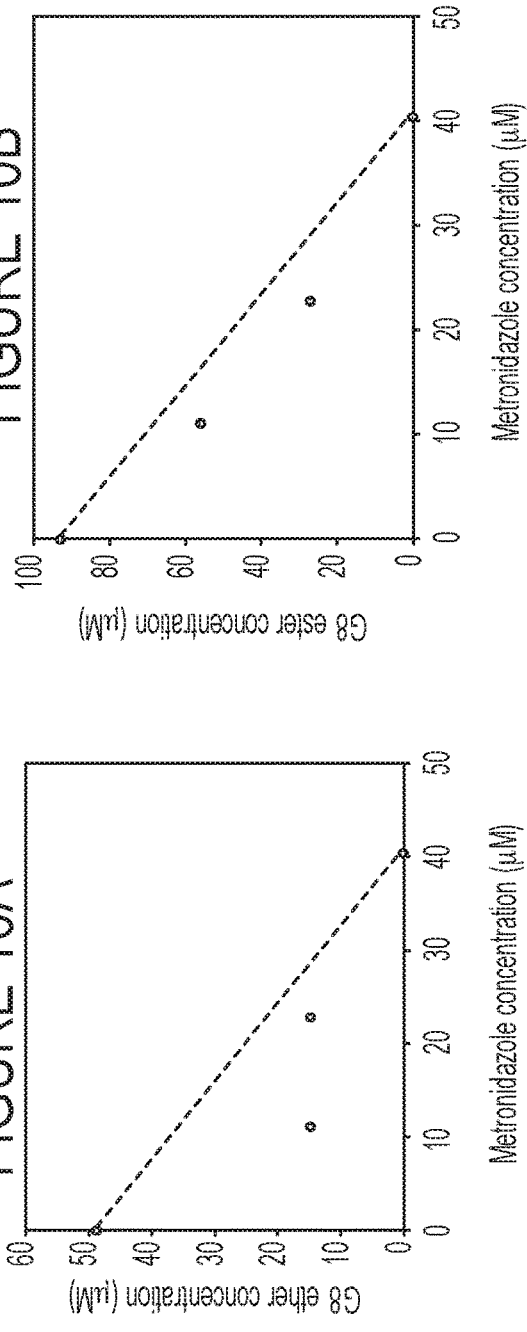
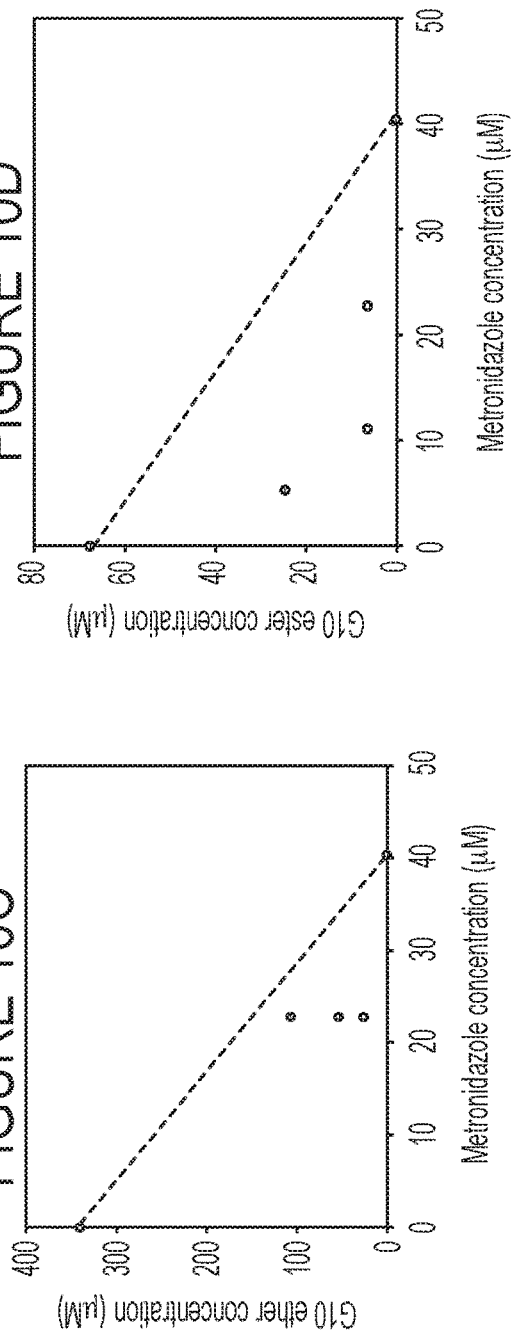
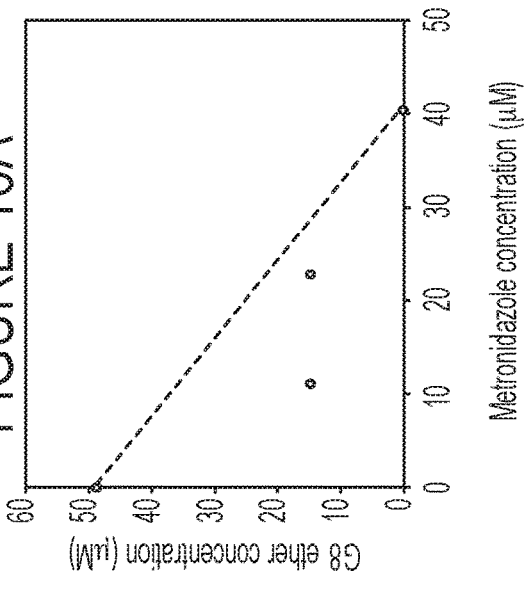
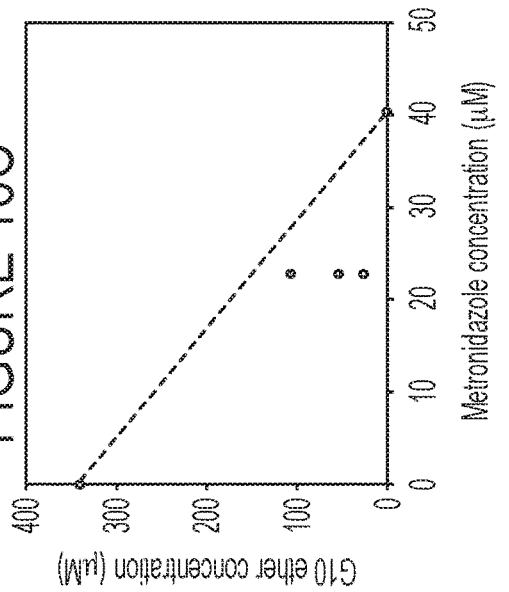
FIGURE 10A
FIGURE 10B
FIGURE 10C
FIGURE 10D

ANTIBACTERIAL AGENTS

RELATED APPLICATION

This application claims the benefit of priority of U.S. Provisional Application Ser. No. 62/312,588 filed on Mar. 24, 2016, which application is incorporated by reference herein.

GOVERNMENT FUNDING

This invention was made with government support under R21 AI126053 awarded by the National Institutes of Health. The government has certain rights in the invention.

BACKGROUND OF THE INVENTION

The development of antibiotic-resistant bacteria is a prevalent concern that has prompted the development of new antimicrobial agents (Park, et al., *International Journal of Molecular Sciences* 2011, 12, 5971; Laverty, et al., *International Journal of Molecular Sciences* 2011, 12, 6566; Tew, et al., *Accounts of Chemical Research* 2010, 43, 30; Boucher, et al., *Clinical Infectious Diseases* 2009, 48, 1). As an alternative to conventional antibiotics, antimicrobial peptides (AMPs) have received widespread attention. Many of the naturally occurring AMPs elicit antibacterial activity by targeting the cellular membrane (Park, et al., *International Journal of Molecular Sciences* 2011, 12, 5971; Laverty, et al., *International Journal of Molecular Sciences* 2011, 12, 6566; Tew, et al., *Accounts of Chemical Research* 2010, 43, 30). Although these peptides have diverse primary structures, many exhibit a net cationic charge and facially amphiphilic secondary structure in which hydrophobic and hydrophilic domains exist on opposite 'faces' of the molecule (Zhao, Y. *Current Opinion in Colloid & Interface Science* 2007, 12, 92); it is the cationic, amphiphilic character that appears to give rise to AMPs' unique mechanism of action (Park, et al., *International Journal of Molecular Sciences* 2011, 12, 5971; Laverty, et al., *International Journal of Molecular Sciences* 2011, 12, 6566; Tew, et al., *Accounts of Chemical Research* 2010, 43, 30). These AMPs first interact with negatively charged bacterial membranes via electrostatic bonding (Laverty, G.; Gorman, S. P.; Gilmore, B. F. *International Journal of Molecular Sciences* 2011, 12, 6566; Brogden, K. A. *Nature Reviews Microbiology* 2005, 3, 238). After the initial interaction, AMPs' hydrophobic domains interact with the hydrophobic membrane interior, ultimately disrupting the membrane and resulting in cell death (Laverty, G.; Gorman, S. P.; Gilmore, B. F. *International Journal of Molecular Sciences* 2011, 12, 6566; Brogden, K. A. *Nature Reviews Microbiology* 2005, 3, 238). Owing to their membrane-targeting activity, AMPs exhibit reduced instances of bacterial resistance and are promising antibiotic alternatives (Laverty, G.; Gorman, S. P.; Gilmore, B. F. *International Journal of Molecular Sciences* 2011, 12, 6566; Grenier, et al., *Bioorganic & Medicinal Chemistry Letters* 2012, 22, 4055; Ling, et al., *Nature* 2015, advance online publication). However, high production costs and scalability difficulties, as well as low solubility, bioavailability and metabolic stability (e.g., instability in the presence of proteases), has limited their clinical application (Tew, et al., *Accounts of Chemical Research* 2010, 43, 30; Scorciapino, et al., *Biophys. J.* 2012, 102, 1039; Hancock, R. E. W.; Sahl, H.-G. *Nature Biotechnology* 2006, 24, 1551).

Accordingly, there is a need for new agents that have antibacterial properties.

SUMMARY OF THE INVENTION

Applicant has discovered novel cationic amphiphiles, which may be used as therapeutic compounds. These amphiphiles may also be useful in biomedical applications, including antimicrobial and delivery applications. Research suggests that such cationic amphiphiles can self assemble into micelles, complex with liposomes, or be formulated into nanoparticles for various delivery applications. These amphiphiles could thus be used as therapeutic compounds, as delivery vehicles for bioactives, including oligonucleotides, or for diagnostics. Additionally, these cationic amphiphiles could improve the performance of current antimicrobial products. Thus, therapeutic compounds are described below. In particular, compounds with antibacterial properties are described below.

Accordingly, the invention provides a compound of formula I:

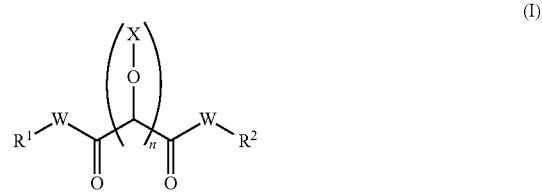

wherein:
R$^1$ is a polyether or a (C$_1$-C$_6$)alkyl that is substituted with one or more NR$_a$R$_b$;
R$^2$ is a polyether or a (C$_1$-C$_6$)alkyl that is substituted with one or more NR$_a$R$_b$;
each W is independently —NH—, —O— or —S—;
each X is independently (C$_1$-C$_{20}$)alkyl;
each R$_a$ is independently H or (C$_1$-C$_6$)alkyl;
each R$_b$ is independently H, (C$_1$-C$_6$)alkyl or —C(=NH)NH$_2$; and
n is 1, 2, 3, 4, 5, 6, 7, or 8;
or a salt thereof.

The invention also provides a compound of formula II:

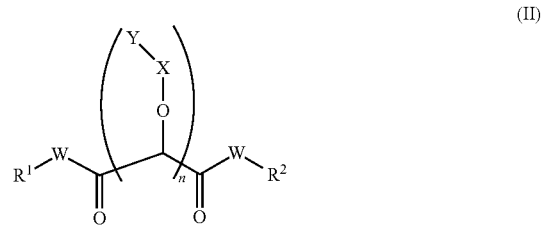

wherein:
R$^1$ is a polyether or a (C$_1$-C$_6$)alkyl that is optionally substituted with one or more NR$_a$R$_b$;
R$^2$ is a polyether or a (C$_1$-C$_6$)alkyl that is optionally substituted with one or more NR$_a$R$_b$;
each W is independently —NH—, —O— or —S—;
each X is independently (C$_2$-C$_{20}$)alkyl;
R$_a$ and R$_b$ are each independently H or (C$_1$-C$_6$)alkyl;
each Y is independently —NH$_2$, —N$^+$(R$^c$)$_3$Z$^-$, —NH—C(=NH)—NH$_2$ or —NH—BOC;

each $R^c$ is independently $(C_1\text{-}C_6)$alkyl;

Z is a counter ion; and n is 1, 2, 3, 4, 5, 6, 7, or 8;

or a salt thereof.

The invention also provides a method for treating a bacterial infection in a mammal (e.g., a human) comprising administering to the mammal an effective amount of a compound of formula I, or a pharmaceutically acceptable salt thereof, or a compound of formula II, or a pharmaceutically acceptable salt thereof.

The invention also provides a composition comprising a compound of formula I, or a pharmaceutically acceptable salt thereof, or a compound of formula II, or a pharmaceutically acceptable salt thereof, and a pharmaceutically acceptable vehicle.

The invention also provides a compound of formula I, pharmaceutically acceptable salt thereof, or a compound of formula II, or a pharmaceutically acceptable salt thereof, for the prophylactic or therapeutic treatment of a bacterial infection.

The invention also provides a compound of formula I, or a pharmaceutically acceptable salt thereof, or a compound of formula II, or a pharmaceutically acceptable salt thereof, for use in medical treatment.

The invention also provides the use of a compound of formula I, or a pharmaceutically acceptable salt thereof, or a compound of formula II, or a pharmaceutically acceptable salt thereof, for the preparation of a medicament for treating a bacterial infection in a mammal (e.g., a human).

Certain embodiments of the invention provide a kit comprising a compound of formula I, or a pharmaceutically acceptable salt thereof, or a compound of formula II, or a pharmaceutically acceptable salt thereof, packaging material, and instructions for administering the compound, or a pharmaceutically acceptable salt thereof, to a mammal to treat a bacterial infection.

Certain embodiments of the invention also provide a method for treating bacterial vaginosis in a mammal comprising administering to the mammal an effective amount of a compound of formula (I):

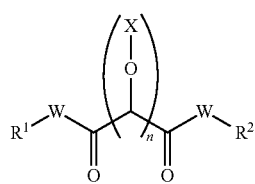

(I)

wherein:

$R^1$ is a polyether or a $(C_1\text{-}C_6)$alkyl that is substituted with one or more $NR_aR_b$;

$R^2$ is a polyether or a $(C_1\text{-}C_6)$alkyl that is substituted with one or more $NR_aR_b$;

each W is independently —NH—, —O— or —S—;

each X is independently $(C_1\text{-}C_{20})$alkyl or $(C_2\text{-}C_{20})$alkanoyl;

each $R_a$ is independently H or $(C_1\text{-}C_6)$alkyl;

each $R_b$ is independently H, $(C_1\text{-}C_6)$alkyl or —C(=NH)NH$_2$; and n is 1, 2, 3, 4, 5, 6, 7, or 8;

or a pharmaceutically acceptable salt thereof.

Certain embodiments of the invention also provide a method for treating bacterial vaginosis in a mammal comprising administering to the mammal an effective amount of a compound of formula (II):

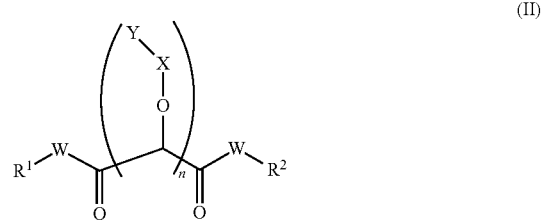

(II)

wherein:

$R^1$ is a polyether or a $(C_1\text{-}C_6)$alkyl that is optionally substituted with one or more $NR_aR_b$;

$R^2$ is a polyether or a $(C_1\text{-}C_6)$alkyl that is optionally substituted with one or more $NR_aR_b$;

each W is independently —NH—, —O— or —S—;

each X is independently $(C_2\text{-}C_{20})$alkyl or $(C_2\text{-}C_{20})$alkanoyl;

$R_a$ and $R_b$ are each independently H or $(C_1\text{-}C_6)$alkyl;

each Y is independently —NH$_2$, —N$^+$(R$^c$)$_3$Z, —NH—C(=NH)—NH$_2$ or —NH—BOC;

each $R^c$ is independently $(C_1\text{-}C_6)$alkyl;

Z is a counter ion; and n is 1, 2, 3, 4, 5, 6, 7, or 8;

or a pharmaceutically acceptable salt thereof.

The invention also provides processes and intermediates disclosed herein that are useful for preparing compounds of formula I, or salts thereof, or compounds of formula II, or salts thereof.

As described in the Examples, experiments measuring the minimum inhibitory concentrations (MIC) and minimum bactericidal concentrations (MBC) against gram positive, gram negative and gram variable bacteria were performed using compounds of formula (I). The compounds may be useful as therapeutic agents for clinical applications. The compounds may also be useful to provide an antibiotic effect in soaps and coatings or as delivery agents for other therapeutic or diagnostic agents. The compounds may kill bacterial cells through a membrane disrupting mechanism, which is difficult for bacteria to develop resistance against and has broad antimicrobial spectrum. Additionally, the compounds are simple and inexpensive to prepare, feasible to scale-up, generally have sufficient solubility at both salt-rich conditions (human plasma) and salt-free conditions (water), and generally are not susceptible to degradation.

BRIEF DESCRIPTION OF THE FIGURES

FIG. 1A shows the structure of CAms 5a, 5b, 5c, 8a, 8b and 8c. FIG. 1B shows hemolysis (%) for various concentrations of CAms 5a, 5b, 5c, 8a, 8b and 8c. FIG. 1C shows cell viability (%) for 5b and 8b at 3.9 ug/ml and 0.95 ug/ml.

FIGS. 2A-D. FIGS. 2A and 2C show SEM micrographs of S. aureus (FIG. 2A) and E. coli (FIG. 2C) before incubation with 5b at their respective MICs. FIGS. 2B and 2D show SEM micrographs of S. aureus (FIG. 2B) and E. coli (FIG. 2D) after incubation with 5b at their respective MICs. Varied morphology changes of cell membranes are indicated by arrows.

FIGS. 3A and 3C show TEM micrographs of S. aureus (FIG. 3A) and E. coli (FIG. 3C) before incubation with 5b at their respective MICs. FIGS. 3B and 3D show TEM micrographs of S. aureus (FIG. 3B) and E. coli (FIG. 3D) after incubation with 5b at their respective MICs. CW (cell wall or outer membrane), CM (cell membrane).

FIGS. 10A-D. Combination of metronidazole with CAms against biofilm cells of *G. vaginalis*. Combination of metronidazole with G8 ether (FIG. 10A), with G8 ester (FIG. 10B), with G10 ether (FIG. 10C) and with G10 ester (FIG. 10D).

(FIG. 11A) CAms-untreated *G. vaginalis* biofilm, (FIG. 11B) *G. vaginalis* biofilm treated with 58.8 μM of G8 ether, (FIG. 11C) *G. vaginalis* biofilm treated with a combination of 29.4 μM of G8 ether and 40.4 μM of metronidazole.

DETAILED DESCRIPTION

Figure 1A:
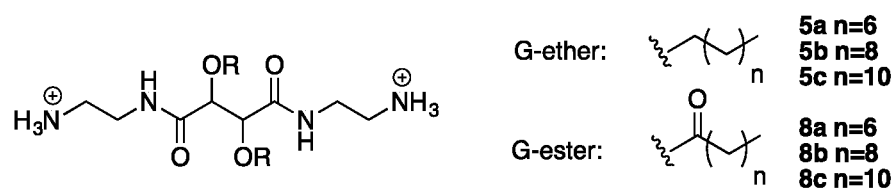
FIGS. 1A-C.

Described herein are amphiphiles comprised of branched backbones (e.g., sugar-based) that are modified with alkyl chains of varying length via an ether linkage. The ether linkage, which is resistant to enzyme-catalyzed degradation, imparts enhanced stability to the molecule, while also potentially improving the pharmacokinetic profile (e.g., bioavailability, circulation time) of the compound. Additionally, amine-containing moieties were terminally incorporated on the amphiphiles' backbones to impart an overall cationic charge. As described in the Examples, amphiphiles with varying antimicrobial potencies, solubilities, and stabilities were developed by altering the length of the hydrophobic chains and the type of cationic charge. These cationic amphiphiles have been shown to interact with bacterial cell membranes and may be used to improve the performance of current antimicrobial products or as alternatives to existing antimicrobial technologies.

Compounds of Formula (I)

Accordingly, the invention provides a compound of formula I:

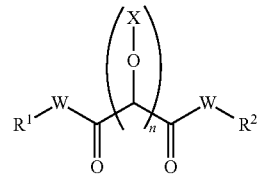

(I)

wherein:

$R^1$ is a polyether or a $(C_1-C_6)$alkyl that is substituted with one or more $NR_aR_b$;

$R^2$ is a polyether or a $(C_1-C_6)$alkyl that is substituted with one or more $NR_aR_b$;

each W is independently —NH—, —O— or —S—;

each X is independently $(C_1-C_{20})$alkyl;

each $R_a$ is independently H or $(C_1-C_6)$alkyl;

each $R_b$ is independently H, $(C_1-C_6)$alkyl or —C(═NH)$NH_2$; and n is 1, 2, 3, 4, 5, 6, 7, or 8;

or a salt thereof.

In certain embodiments, each $R_a$ is independently H. In certain embodiments, each $R_a$ is independently $(C_1-C_6)$ alkyl.

In certain embodiments, each $R_b$ is independently H. In certain embodiments, each $R_b$ is independently $(C_1-C_6)$ alkyl. In certain embodiments, each $R_b$ is independently —C(═NH)$NH_2$.

In certain embodiments, n is 2. In certain embodiments, n is 3. In certain embodiments, n is 4. In certain embodiments, n is 5.

In certain embodiments, a compound of formula I is a compound of formula (Ia):

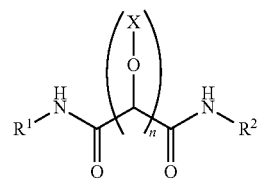

(Ia)

wherein:

$R^1$ is a polyether or a $(C_1-C_6)$alkyl that is substituted with one or more $NR_aR_b$;

$R^2$ is a polyether or a $(C_1-C_6)$alkyl that is substituted with one or more $NR_aR_b$;

each X is independently $(C_1-C_{20})$alkyl;

each $R_a$ is independently H or $(C_1-C_6)$alkyl;

each $R_b$ is independently H, $(C_1-C_6)$alkyl or —C(═NH)$NH_2$; and n is 1, 2, 3, 4, 5, 6, 7, or 8;

or a salt thereof.

In certain embodiments, a compound of formula I is a compound of formula Ib:

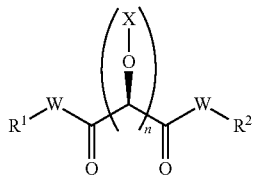
(Ib)

wherein:
R¹ is a polyether or a $(C_1-C_6)$alkyl that is substituted with one or more $NR_aR_b$;
R² is a polyether or a $(C_1-C_6)$alkyl that is substituted with one or more $NR_aR_b$;
each W is independently —NH—, —O— or —S—;
each X is independently $(C_1-C_{20})$alkyl;
$R_a$ is each independently H or $(C_1-C_6)$alkyl;
$R_b$ is each independently H, $(C_1-C_6)$alkyl or —C(=NH)NH$_2$; and
n is 1, 2, 3, 4, 5, 6, 7, or 8;
or a salt thereof.

In certain embodiments, a compound of formula I is a compound of formula Ib':

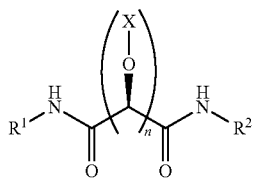
(Ib')

wherein:
R¹ is a polyether or a $(C_1-C_6)$alkyl that is substituted with one or more $NR_aR_b$;
R² is a polyether or a $(C_1-C_6)$alkyl that is substituted with one or more $NR_aR_b$;
each X is independently $(C_1-C_{20})$alkyl;
$R_a$ is each independently H or $(C_1-C_6)$alkyl;
$R_b$ is each independently H, $(C_1-C_6)$alkyl or —C(=NH)NH$_2$; and
n is 1, 2, 3, 4, 5, 6, 7, or 8;
or a salt thereof.

In certain embodiments, a compound of formula I is a compound of formula Ic:

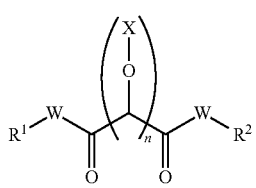
(Ic)

wherein:
R¹ is a polyether or a $(C_1-C_6)$alkyl that is substituted with one or more $NR_aR_b$;
R² is a polyether or a $(C_1-C_6)$alkyl that is substituted with one or more $NR_aR_b$;
each W is independently —NH—, —O— or —S—;
each $R_a$ is H; and
each $R_b$ is H;
or a salt thereof.

In certain embodiments, a compound of formula I is a compound of formula Ic':

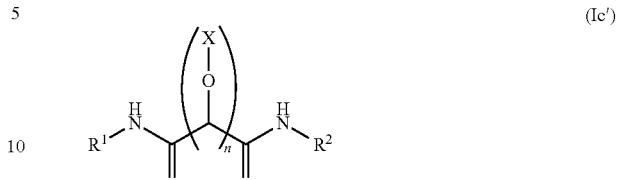
(Ic')

wherein:
R¹ is a polyether or a $(C_1-C_6)$alkyl that is substituted with one or more $NR_aR_b$;
R² is a polyether or a $(C_1-C_6)$alkyl that is substituted with one or more $NR_aR_b$;
each $R_a$ is H; and
each $R_b$ is H;
or a salt thereof.

In certain embodiments, a compound of formula I is a compound of formula Id:

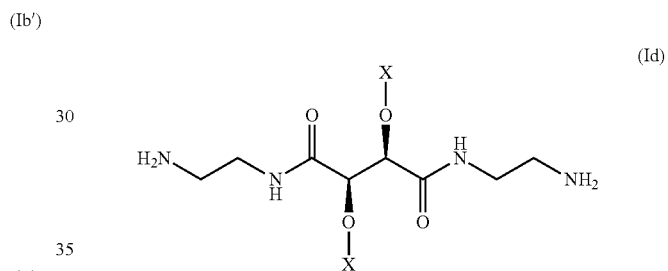
(Id)

or a salt thereof.

In certain embodiments, a compound of the invention is selected from:

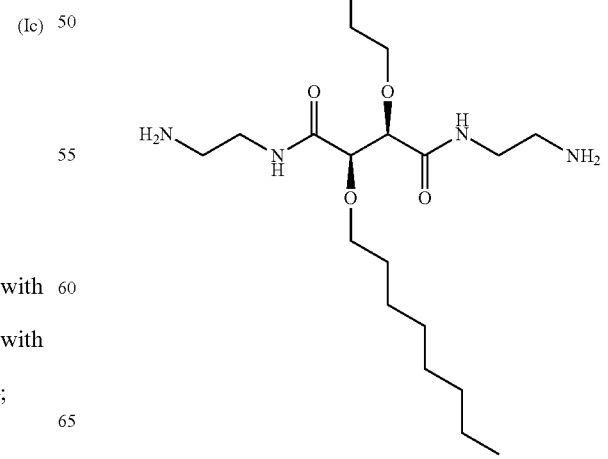

-continued
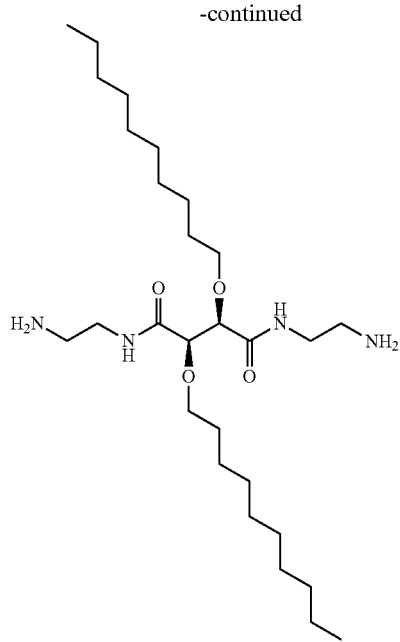
and
and salts thereof.
In certain embodiments, a compound of the invention is:
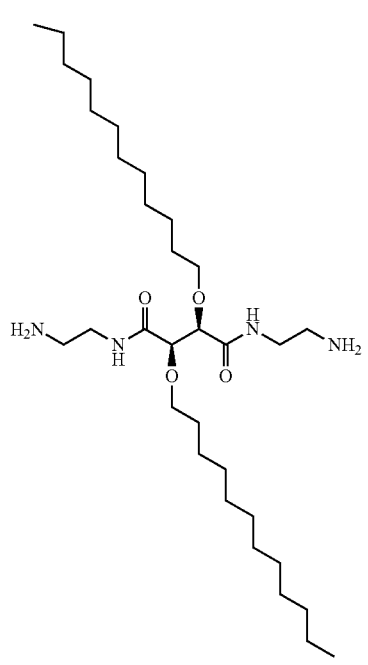 [SMILES: CCCCCCCCCCCCO[C@@H](C(=O)NCCN)[C@@H](OCCCCCCCCCCCC)C(=O)NCCN]
or a pharmaceutically acceptable salt thereof.
In certain embodiments, a compound of the invention is selected from:

-continued

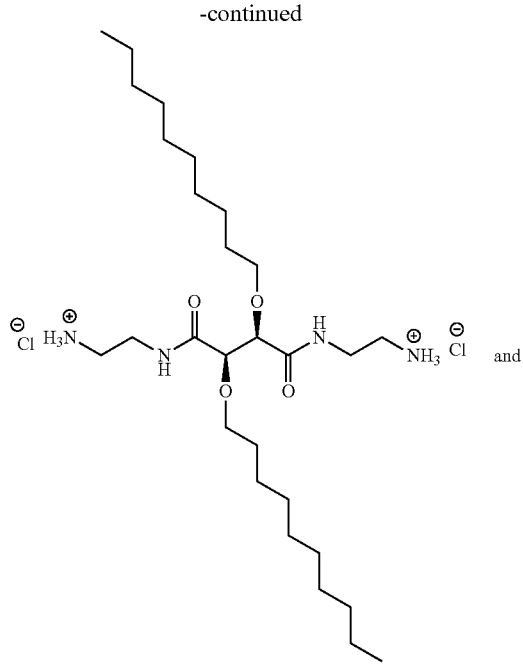

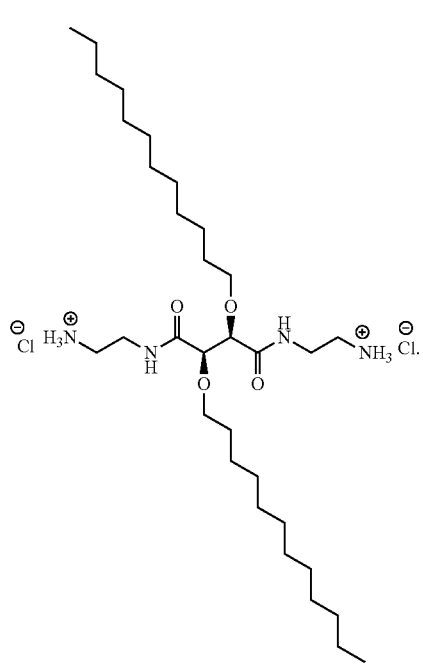

In certain embodiments, a compound of the invention is:

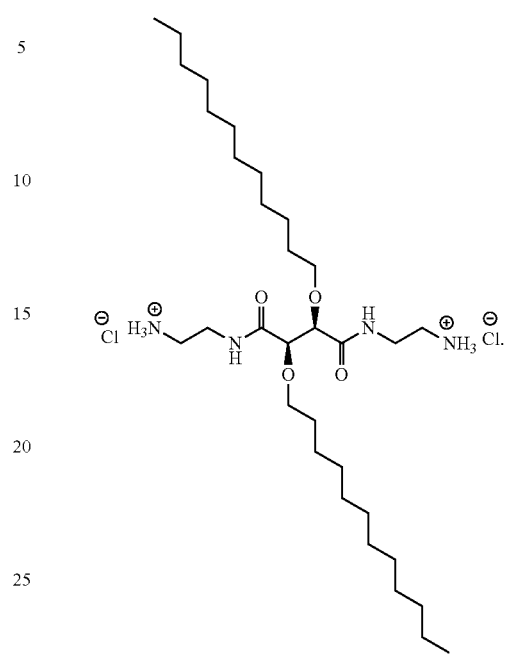

Compounds of Formula (II)

The invention also provides a compound of formula II:

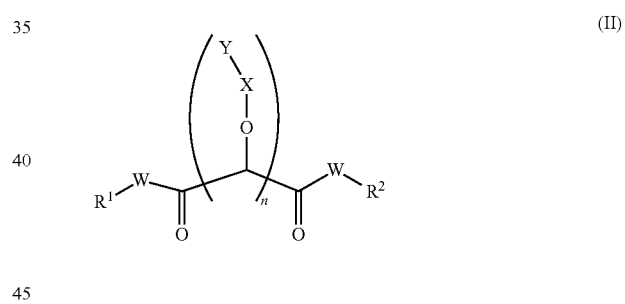

(II)

wherein:

$R^1$ is a polyether or a $(C_1\text{-}C_6)$alkyl that is optionally substituted with one or more $NR_aR_b$;

$R^2$ is a polyether or a $(C_1\text{-}C_6)$alkyl that is optionally substituted with one or more $NR_aR_b$;

each W is independently —NH—, —O— or —S—;

each X is independently $(C_2\text{-}C_{20})$alkyl;

$R_a$ and $R_b$ are each independently H or $(C_1\text{-}C_6)$alkyl;

each Y is independently —NH$_2$, —N$^+$(R$^c$)$_3$Z$^-$, —NH—C(=NH)—NH$_2$ or —NH—BOC;

each $R^c$ is independently $(C_1\text{-}C_6)$alkyl;

Z is a counter ion; and n is 1, 2, 3, 4, 5, 6, 7, or 8;

or a salt thereof.

Certain embodiments of the invention also provide a compound of formula IIa:

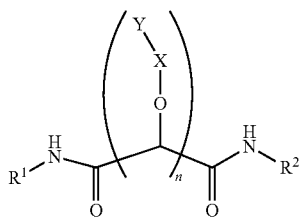

(IIa)

wherein:
R$^1$ is a polyether or a (C$_1$-C$_6$)alkyl that is optionally substituted with one or more NR$_a$R$_b$;
R$^2$ is a polyether or a (C$_1$-C$_6$)alkyl that is optionally substituted with one or more NR$_a$R$_b$;
each X is independently (C$_2$-C$_{20}$)alkyl;
R$_a$ and R$_b$ are each independently H or (C$_1$-C$_6$)alkyl;
each Y is independently —NH$_2$, —N$^+$(R$^c$)$_3$Z, —NH—C(=NH)—NH$_2$ or —NH—BOC;
each R$^c$ is independently (C$_1$-C$_6$)alkyl;
Z is a counter ion; and
n is 1, 2, 3, 4, 5, 6, 7, or 8;
or a salt thereof.

In certain embodiments, each Y is independently —NH$_2$.
In certain embodiments, each Y is independently —N$^+$(R$^c$)$_3$Z$^-$.
In certain embodiments, each Y is independently —NH—C(=NH)—NH$_2$.
In certain embodiments, each Y is independently —NH—BOC.

In certain embodiments, each R$_a$ is independently H. In certain embodiments, each R$_a$ is independently (C$_1$-C$_6$)alkyl.
In certain embodiments, each R$_b$ is independently H. In certain embodiments, each R$_b$ is independently (C$_1$-C$_6$)alkyl.
In certain embodiments, n is 2. In certain embodiments, n is 3. In certain embodiments, n is 4. In certain embodiments, n is 5.

In certain embodiments, a compound of formula II is a compound of formula IIb:

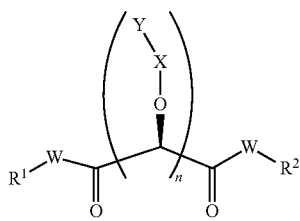

(IIb)

wherein:
R$^1$ is a polyether or a (C$_1$-C$_6$)alkyl that is optionally substituted with one or more NR$_a$R$_b$;
R$^2$ is a polyether or a (C$_1$-C$_6$)alkyl that is optionally substituted with one or more NR$_a$R$_b$;
each W is independently —NH—, —O— or —S—;
each X is independently (C$_2$-C$_{20}$)alkyl;
R$_a$ and R$_b$ are each independently H or (C$_1$-C$_6$)alkyl;
each Y is independently —NH$_2$, —N$^+$(R$^c$)$_3$Z$^-$, —NH—C(=NH)—NH$_2$ or —NH—BOC;
each R$^c$ is independently (C$_1$-C$_6$)alkyl;
Z is a counter ion; and
n is 1, 2, 3, 4, 5, 6, 7, or 8;
or a salt thereof.

In certain embodiments, a compound of formula II is a compound of formula IIb':

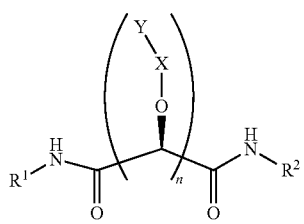

(IIb')

wherein:
R$^1$ is a polyether or a (C$_1$-C$_6$)alkyl that is optionally substituted with one or more NR$_a$R$_b$;
R$^2$ is a polyether or a (C$_1$-C$_6$)alkyl that is optionally substituted with one or more NR$_a$R$_b$;
each X is independently (C$_2$-C$_{20}$)alkyl;
R$_a$ and R$_b$ are each independently H or (C$_1$-C$_6$)alkyl;
each Y is independently —NH$_2$, —N$^+$(R$^c$)$_3$Z$^-$, —NH—C(=NH)—NH$_2$ or —NH—BOC;
each R$^c$ is independently (C$_1$-C$_6$)alkyl;
Z is a counter ion; and
n is 1, 2, 3, 4, 5, 6, 7, or 8;
or a salt thereof.

In certain embodiments, a compound of formula II is a compound of formula IIc:

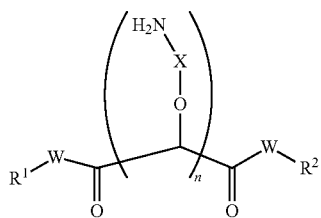

(IIc)

wherein:
each W is independently —NH—, —O— or —S—;
R$^1$ is a polyether or a (C$_1$-C$_6$)alkyl; and
R$^2$ is a polyether or a (C$_1$-C$_6$)alkyl;
or a salt thereof.

In certain embodiments, a compound of formula II is a compound of formula IIc':

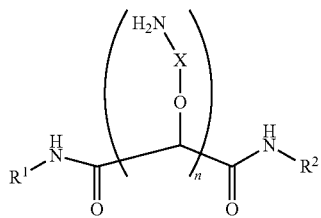

(IIc')

wherein:
R$^1$ is a polyether or a (C$_1$-C$_6$)alkyl; and
R$^2$ is a polyether or a (C$_1$-C$_6$)alkyl;
or a salt thereof.

In certain embodiments, a compound of formula II is a compound of formula IIc":

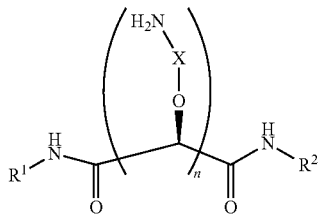
(IIc")

wherein:
R¹ is a polyether or a $(C_1$-$C_6)$alkyl; and
R² is a polyether or a $(C_1$-$C_6)$alkyl;
or a salt thereof.

In certain embodiments, a compound of formula II is a compound of formula IId:

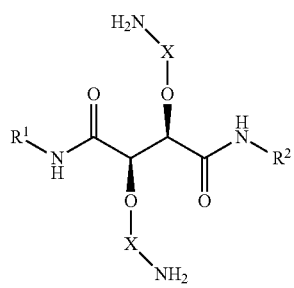
(IId)

or a salt thereof.

In certain embodiments, a compound of the invention is selected from:

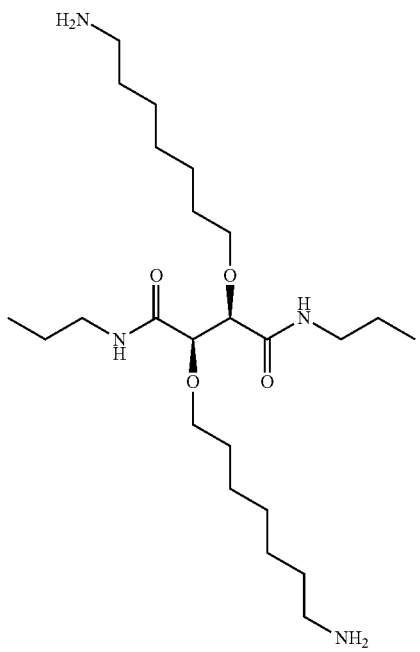

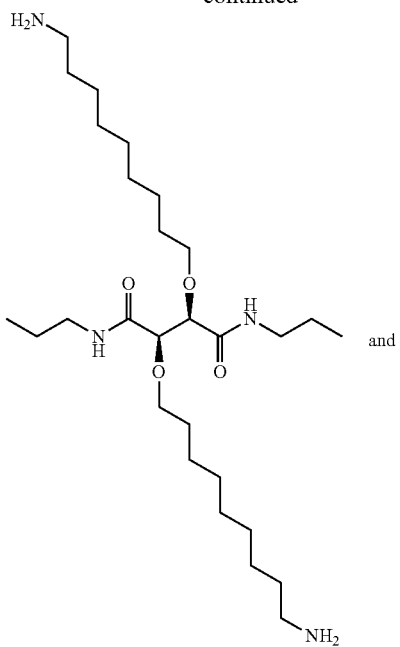
and

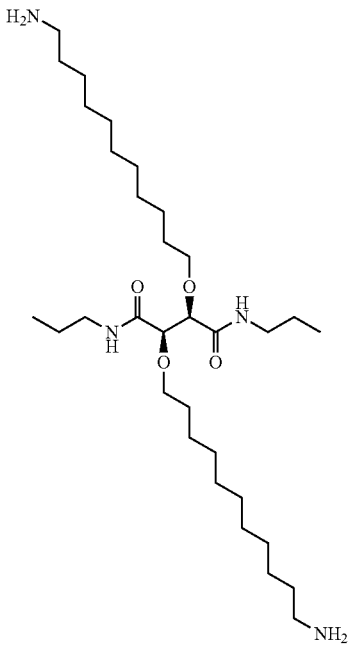 [SMILES: CCCNC(=O)[C@H](OCCCCCCCCCCCN)[C@@H](OCCCCCCCCCCCN)C(=O)NCCC]

and salts thereof.

In certain embodiments, a compound of the invention is selected from:

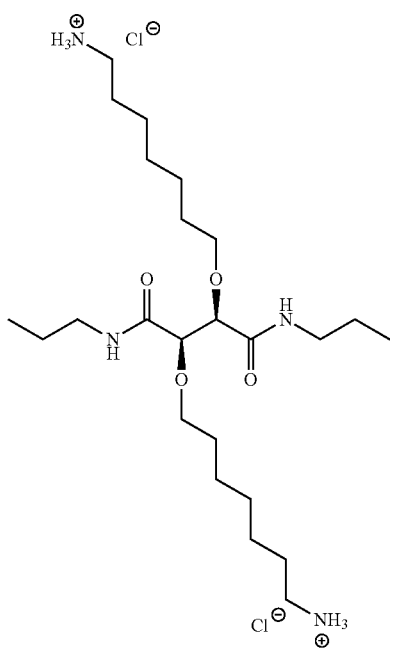

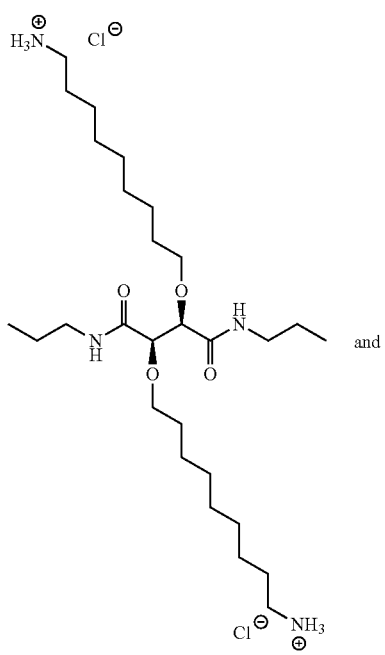

and

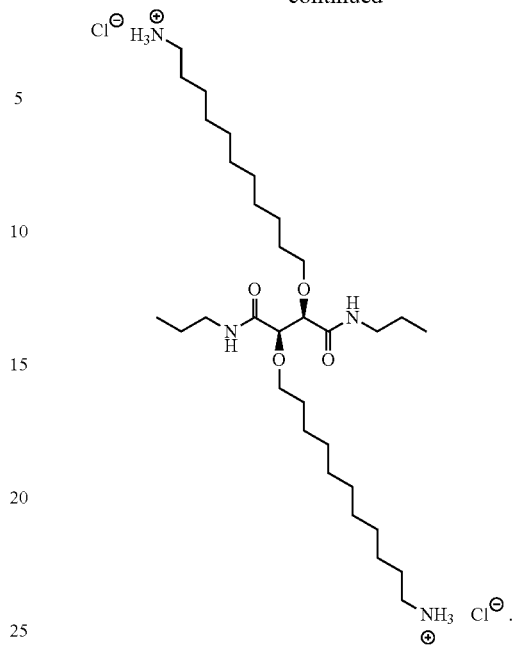

Variables "R¹" and "R²"

As described herein, certain embodiments of the invention provide compounds of formula I, wherein $R^1$ is a polyether or a $(C_1\text{-}C_6)$alkyl that is substituted with one or more $NR_aR_b$; and $R^2$ is a polyether or a $(C_1\text{-}C_6)$alkyl that is substituted with one or more $NR_aR_b$. Certain embodiments of the invention provide also compounds of formula II, wherein $R^1$ is a polyether or a $(C_1\text{-}C_6)$alkyl that is optionally substituted with one or more $NR_aR_b$; and $R^2$ is a polyether or a $(C_1\text{-}C_6)$alkyl that is optionally substituted with one or more $NR_aR_b$.

In certain embodiments, $R^1$ is a $(C_1\text{-}C_6)$alkyl that is optionally substituted with one or more $NR_aR_b$.

In certain embodiments, $R^1$ is a $(C_1\text{-}C_6)$alkyl that is substituted with one or more $NR_aR_b$.

In certain embodiments, $R^1$ is methyl, ethyl, propyl, isopropyl, butyl, isobutyl, or sec-butyl, optionally substituted with one or more $NR_aR_b$.

In certain embodiments, $R^1$ is methyl, ethyl, propyl, isopropyl, butyl, isobutyl, or sec-butyl.

In certain embodiments, $R^1$ is propyl.

In certain embodiments, $R^1$ is ethyl substituted with one or more $NR_aR_b$.

In certain embodiments, $R^1$ is a polyether. As used herein, the term polyether includes poly(alkylene oxides) having between about 2 and about 150 repeating units. Typically, the poly(alkylene oxides) have between about 50 and about 115 repeating units. The alkylene oxide units contain from 2 to 10 carbon atoms and may be straight chained or branched. Preferably, the alkylene oxide units contain from 2 to 10 carbon atoms. Poly(ethylene glycol) (PEG) is a specific example of a poly(alkylene oxide). Alkoxy-, amino-, carboxy-, and sulfo-terminated poly(alkylene oxides) are also examples, with methoxy-terminated poly(alkylene oxides) being a specific example.

In one embodiment the polyether has the following structure:

$$R_5\text{—}(R_6\text{—}O\text{—})_a\text{—}R_6\text{—}$$

wherein $R_5$ is a 1 to 20 carbon straight-chain or branched alkyl group, —OH, —OR$_7$, —NH$_2$, —NHR$_7$, —NHR$_7$R$_8$, —CO$_2$H, —SO$_3$H (sulfo), —CH$_2$—OH, —CH$_2$—OR$_7$, —CH$_2$—O—CH$_2$—R$_7$, —CH$_2$—NH$_2$, —CH$_2$—NHR$_7$, —CH$_2$—NR$_7$R$_8$, —CH$_2$CO$_2$H, —CH$_2$SO$_3$H, or —O—C(=O)—CH$_2$—CH$_2$—C(=O)—O—;

$R_6$ is a 1 to 10 carbon straight-chain or branched divalent alkylene group;

each $R_7$ and $R_8$ is independently a 1 to 6 carbon straight-chain or branched alkylene group; and a is an integer from 2 to 150, inclusive.

In certain embodiments, a is an integer from 20 to 140, inclusive. In certain embodiments, a is an integer from 50 to 130, inclusive. In certain embodiments, a is an integer from 75 to 130, inclusive. In certain embodiments, a is an integer from 100 to 130, inclusive. In certain embodiments, a is 113.

In another embodiment the polyether is methoxy terminated poly(ethylene glycol).

In certain embodiments, $R^2$ is a (C$_1$-C$_6$)alkyl that is optionally substituted with one or more NR$_a$R$_b$.

In certain embodiments, $R^2$ is a (C$_1$-C$_6$)alkyl that is substituted with one or more NR$_a$R$_b$.

In certain embodiments, $R^2$ is methyl, ethyl, propyl, isopropyl, butyl, isobutyl, or sec-butyl, optionally substituted with one or more NR$_a$R$_b$.

In certain embodiments, $R^2$ is methyl, ethyl, propyl, isopropyl, butyl, isobutyl, or sec-butyl.

In certain embodiments, $R^2$ is propyl.

In certain embodiments, $R^2$ is ethyl substituted with one or more NR$_a$R$_b$.

In certain embodiments, $R^2$ is a polyether as described herein.

Variable "X"

As described herein, in certain embodiments of compounds of formula I, each X is independently (C$_1$-C$_{20}$)alkyl, and in certain embodiments of compounds of formula II, each X is independently (C$_2$-C$_{20}$)alkyl. In certain embodiments of compounds of formulas I and II, each X is independently (C$_2$-C$_{20}$)alkyl. In certain embodiments of compounds of formulas I and II, each X is independently (C$_4$-C$_{14}$)alkyl. In certain embodiments of compounds of formulas I and II, each X is independently (C$_6$-C$_{12}$)alkyl. In certain embodiments of compounds of formulas I and II, each X is independently (C$_6$)alkyl. In certain embodiments of compounds of formulas I and II, each X is independently (C$_7$)alkyl. In certain embodiments of compounds of formulas I and II, each X is independently (C$_8$)alkyl. In certain embodiments of compounds of formulas I and II, each X is independently (C$_9$)alkyl. In certain embodiments of compounds of formulas I and II, each X is independently (C$_{10}$)alkyl. In certain embodiments of compounds of formulas I and II, each X is independently (C$_{11}$)alkyl. In certain embodiments of compounds of formulas I and II, each X is independently (C$_{12}$)alkyl. In certain embodiments of compounds of formulas I and II, each X is independently (C$_{13}$)alkyl. In certain embodiments of compounds of formulas I and II, each X is independently (C$_{14}$)alkyl.

Variable "W"

As described herein, in certain embodiments of compounds of formula I, or a salt thereof, and of compounds of formula II, or a salt thereof, each W is independently —NH—, —O— or —S—. In certain embodiments of compounds of formulas I and II, or salts thereof, each W is independently —NH—. In certain embodiments of compounds of formulas I and II, or salts thereof, each W is independently —O—. In certain embodiments of compounds of formulas I and II, or salts, thereof, each W is independently —S—.

Compositions and Kits

As described herein, compounds of the invention may be formulated as compositions. Accordingly, certain embodiments of the invention provide a pharmaceutical composition comprising a compound of formula I, or a pharmaceutically acceptable salt thereof, or a compound of formula II, or a pharmaceutically acceptable salt thereof, and a pharmaceutically acceptable carrier. In certain embodiments, the composition further comprises a second therapeutic agent.

As used herein, the term "therapeutic agent" includes agents that provide a therapeutically desirable effect when administered to an animal (e.g., a mammal, such as a human). The agent may be of natural or synthetic origin. For example, it may be a nucleic acid, a polypeptide, a protein, a peptide, or an organic compound, such as a small molecule. The term "small molecule" includes organic molecules having a molecular weight of less than about, e.g., 1000 amu. In one embodiment a small molecule can have a molecular weight of less than about 800 amu. In another embodiment a small molecule can have a molecular weight of less than about 500 amu.

For example, the term therapeutic agent includes, but is not limited to, antibiotic agents. Examples of antibiotic agents include, but are not limited to, 4-sulfanilamidosalicylic acid, acediasulfone, amfenac, amoxicillin, ampicillin, apalcillin, apicycline, aspoxicillin, aztreonam, bambermycin(s), biapenem, carbenicillin, carumonam, cefadroxil, cefamandole, cefatrizine, cefbuperazone, cefclidin, cefdinir, cefditoren, cefepime, cefetamet, cefixime, cefmenoxime, cefminox, cefodizime, cefonicid, cefoperazone, ceforanide, cefotaxime, cefotetan, cefotiam, cefozopran, cefpimizole, cefpiramide, cefpirome, cefprozil, cefroxadine, ceftazidime, cefteram, ceftibuten, ceftriaxone, cefuzonam, cephalexin, cephaloglycin, cephalosporin C, cephradine, ciprofloxacin, clinafloxacin, clindamycin, cyclacillin, enoxacin, epicillin, flomoxef, grepafloxacin, hetacillin, imipenem, lomefloxacin, lymecycline, meropenem, metronidazole, moxalactam, mupirocin, nadifloxacin, norfloxacin, panipenem, pazufloxacin, penicillin N, pipemidic acid, quinacillin, ritipenem, salazosulfadimidine, sparfloxacin, succisulfone, sulfachrysoidine, sulfaloxic acid, teicoplanin, temafloxacin, temocillin, ticarcillin, tigemonam, tinidazole, tosufloxacin, trovafloxacin, vancomycin, and the like.

In certain embodiments, the second therapeutic agent is an antibiotic agent. In certain embodiments, the second therapeutic agent is clindamycin, metronidazole or tinidazole. In certain embodiments, the antibiotic agent is metronidazole.

Certain embodiments provide a personal care product (e.g., a soap) comprising a compound of formula I, or a salt thereof, or a compound of formula II, or a salt thereof. For example, certain embodiments of the invention provide a soap comprising a fatty acid salt and a compound of formula I, or a salt thereof, or a compound of formula II, or a salt thereof.

As used herein, the term "soap" refers to composition comprising a fatty acid salt.

Certain embodiments of the invention provide a coating or paint comprising a compound of formula I, or a salt thereof, or a compound of formula II, or a salt thereof.

Certain embodiments of the invention provide composition comprising a compound of formula I, or a salt thereof, or a compound of formula II, or a salt thereof, and a therapeutic agent (i.e., a second therapeutic agent) or diagnostic agent.

As used herein, the term "diagnostic agent" refers to an agent that may be detected for diagnostic purposes. For example, in certain embodiments, the diagnostic agent may comprise fluorescent groups or chelating groups, which may be labeled with radionuclides.

Certain embodiments of the invention also provide a medical device comprising a compound of formula I, or a salt thereof, or a compound of formula II, or a salt thereof.

Certain embodiments of the invention provide a kit comprising a compound of formula I, or a pharmaceutically acceptable salt thereof, or a compound of formula II, or a pharmaceutically salt thereof; packaging material; and instructions for administering the compound, or a pharmaceutically acceptable salt thereof, to a mammal to treat a bacterial infection. In certain embodiments, the bacterial infection is bacterial vaginosis. In certain embodiments, the kit further comprises an antibiotic agent. In certain embodiments, the antibiotic agent is metronidazole.

Methods of Use

Certain embodiments of the invention provide a method for treating a bacterial infection in a mammal (e.g., a human) comprising administering to the mammal an effective amount of a compound of formula I, or a pharmaceutically acceptable salt thereof, or a compound of formula II, or a pharmaceutically acceptable salt thereof.

In certain embodiments, the method further comprises administering a second therapeutic agent (e.g., an agent as described herein) to the mammal. In certain embodiments, the second therapeutic agent is an antibiotic agent. In certain embodiments, the antibiotic agent is selected from the group consisting of 4-sulfanilamidosalicylic acid, acediasulfone, amfenac, amoxicillin, ampicillin, apalcillin, apicycline, aspoxicillin, aztreonam, bambermycin(s), biapenem, carbenicillin, carumonam, cefadroxil, cefamandole, cefatrizine, cefbuperazone, cefclidin, cefdinir, cefditoren, cefepime, cefetamet, cefixime, cefinenoxime, cefminox, cefodizime, cefonicid, cefoperazone, ceforanide, cefotaxime, cefotetan, cefotiam, cefozopran, cefpimizole, cefpiramide, cefpirome, cefprozil, cefroxadine, ceftazidime, cefteram, ceftibuten, ceftriaxone, cefuzonam, cephalexin, cephaloglycin, cephalosporin C, cephradine, ciprofloxacin, clinafloxacin, clindamycin, cyclacillin, enoxacin, epicillin, flomoxef, grepafloxacin, hetacillin, imipenem, lomefloxacin, lymecycline, meropenem, metronidazole, moxalactam, mupirocin, nadifloxacin, norfloxacin, panipenem, pazufloxacin, penicillin N, pipemidic acid, quinacillin, ritipenem, salazosulfadimidine, sparfloxacin, succisulfone, sulfachrysoidine, sulfaloxic acid, teicoplanin, temafloxacin, temocillin, ticarcillin, tigemonam, tinidazole, tosufloxacin, trovafloxacin and vancomycin. In certain embodiments, the antibiotic agent is metronidazole.

Certain embodiments of the invention provide a compound of formula I, or a pharmaceutically acceptable salt thereof, or a compound of formula II, or a pharmaceutically acceptable salt thereof, for use in medical treatment.

Certain embodiments of the invention provide a compound of formula I, or a pharmaceutically acceptable salt thereof, or a compound of formula II, or a pharmaceutically acceptable salt thereof, for the prophylactic or therapeutic treatment of a bacterial infection.

Certain embodiments of the invention provide a compound of formula I, or a pharmaceutically acceptable salt thereof, or a compound of formula II, or a pharmaceutically acceptable salt thereof, for the prophylactic or therapeutic treatment of a bacterial infection, in combination with antibiotic agent.

As used herein, the term "in combination with" refers to the simultaneous or sequential use of a compound described herein and an antibiotic agent, as well as compositions comprising a compound described herein and an antibiotic agent.

Certain embodiments of the invention provide a pharmaceutical composition as described herein for the prophylactic or therapeutic treatment of a bacterial infection.

Certain embodiments of the invention provide the use of a compound of formula I, or a pharmaceutically acceptable salt thereof, or a compound of formula II, or a pharmaceutically acceptable salt thereof, for the preparation of a medicament for treating a bacterial infection in a mammal (e.g., a human).

Certain embodiments of the invention provide the use of a compound of formula I, or a pharmaceutically acceptable salt thereof, or a compound of formula II, or a pharmaceutically acceptable salt thereof, for the preparation of a medicament for treating a bacterial infection in a mammal (e.g., a human), in combination with an antibiotic agent.

Certain embodiments of the invention provide the use of a pharmaceutical composition as described herein for the preparation of a medicament for treating a bacterial infection in a mammal.

In certain embodiments, the bacterial infection is a Gram-negative bacterial strain infection.

In certain embodiments, the Gram-negative bacterial strain is selected from the group consisting of *Escherichia coli, Caulobacter crescentus, Pseudomonas aeruginosa, Agrobacterium tumefaciens, Branhamella catarrhalis, Citrobacter diversus, Enterobacter aerogenes, Enterobacter cloacae, Enterobacter sakazakii, Enterobacter asburiae, Pantoea agglomerans, Klebsiella pneumoniae, Klebsiella oxytoca, Klebsiella rhinoscleromatis, Proteus mirabilis, Salmonella typhimurium, Salmonella enteriditis, Serratia marcescens, Shigella sonnei, Neisseria gonorrhoeae, Acinetobacter baumannii, Acinetobacter calcoaceticus, Acinetobacter lwoffi, Salmonella enteriditis, Fusobacterium nucleatum, Veillonella parvula, Bacteroides forsythus, Actinobacillus actinomycetemcomitans, Aggregatibacter actinomycetemcomitans, Porphyromonas gingivalis, Helicobacter pylori, Francisella tularensis, Yersinia pestis, Borrelia burgdorferi, Neisseria meningitides, Burkholderia cepacia, Brucella neotomae, Legionella pneumophila, Y. pseudotuberculosis, Salmonella enterica* serovar *typhimurium* and *Haemophilus influenzae.*

In certain embodiments, the bacterial infection is a Gram-negative bacterial strain infection and a compound of formula I is administered to the mammal.

In certain embodiments, the bacterial infection is a Gram-negative bacterial strain infection and a compound of formula II is administered to the mammal.

In certain embodiments, the bacterial infection is a Gram-positive bacterial strain infection.

In certain embodiments, the Gram-positive bacterial strain is selected from the group consisting of *Staphylococcus aureus, Staphylococcus epidermidis, Staphylococcus saprophyticus, Streptococcus pyogenes, Streptococcus faecalis, Enterococcus faecalis, Enterococcus faecium, Bacillus subtilis, Micrococcus luteus, Bacillus anthracis, Bacillus cereus, Clostridium difficile, Propionibacterium acnes, Streptococcus mutans, Actinomyces viscosus, Actinomyces naeslundii, Streptococcus sanguis, Streptococcus pneumoniae, Listeria monocytogenes* and *Streptococcus salivarius.*

In certain embodiments, the bacterial infection is a Gram-positive bacterial strain infection and a compound of formula I is administered to the mammal.

In certain embodiments, the bacterial infection is a Gram-positive bacterial strain infection and a compound of formula II is administered to the mammal.

In certain embodiments, the bacterial infection is a Gram-variable bacterial strain infection.

In certain embodiments, the Gram-variable strain is selected from the group consisting of *G. vaginalis* and *Mycobacterium tuberculosis*.

In certain embodiments, the bacterial infection is a Gram-variable bacterial strain infection and a compound of formula I is administered to the mammal.

In certain embodiments, the bacterial infection is a Gram-variable bacterial strain infection and a compound of formula II is administered to the mammal.

In certain embodiments, the Gram-variable bacterial strain is *Mycobacterium tuberculosis*.

In certain embodiments, the bacterial infection is tuberculosis.

In certain embodiments, the Gram-variable bacterial strain is *G. vaginalis*.

In certain embodiments, the bacterial infection is vaginosis.

In certain embodiments, the bacterial infection is caused by *Gardnerella vaginalis, Peptostreptococcus anaerobius, Mobiluncus curtisii*, and/or *Prevotella bivia*.

In certain embodiments, the bacterial infection is caused by *Gardnerella vaginalis*.

In certain embodiments, the antibiotic agent is metronidazole.

Certain embodiments of the invention provide a method for inhibiting a biofilm comprising contacting the biofilm with an effective amount of a compound as described herein, or a salt thereof. In certain embodiments, the biofilm is a *Gardnerella vaginalis* biofilm. In certain embodiments, a lactobacilli biofilm is not inhibited.

Certain Methods and Compositions for the Treatment of Specific Bacterial Infections (e.g., Bacterial Vaginosis)

As discussed herein, compounds and compositions described herein are useful for the treatment of bacterial infections that cause vaginosis (e.g., caused by *G. vaginalis, Peptostreptococcus anaerobius, Mobiluncus curtisii*, and/or *Prevotella bivia*). For example, compounds of formula (I) and (II), or pharmaceutically acceptable salts thereof, as well as compositions comprising these compounds, are useful for treating bacterial vaginosis (BV).

Compounds of Formula (I)

Thus, certain embodiments of the invention provide a method for treating bacterial vaginosis in a mammal (e.g., a human) comprising administering to the mammal an effective amount of a compound of formula (I):

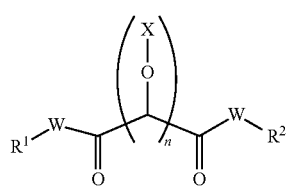

(I)

wherein:

$R^1$ is a polyether or a $(C_1$-$C_6)$alkyl that is substituted with one or more $NR_aR_b$;

$R^2$ is a polyether or a $(C_1$-$C_6)$alkyl that is substituted with one or more $NR_aR_b$;

each W is independently —NH—, —O— or —S—;

each X is independently $(C_1$-$C_{20})$alkyl or $(C_2$-$C_{20})$alkanoyl;

each $R_a$ is independently H or $(C_1$-$C_6)$alkyl;

each $R_b$ is independently H, $(C_1$-$C_6)$alkyl or —C(=NH)NH$_2$; and n is 1, 2, 3, 4, 5, 6, 7, or 8;

or a pharmaceutically acceptable salt thereof.

In certain embodiments, the method further comprises administering a second therapeutic agent. In certain embodiments, the second therapeutic agent is an antibiotic agent. In certain embodiments, the antibiotic agent is clindamycin, metronidazole or tinidazole. In certain embodiments, the antibiotic agent is metronidazole.

The compound of formula I, or a pharmaceutically acceptable salt thereof, and the antibiotic agent (e.g., metronidazole) may be administered either simultaneously or sequentially.

In certain embodiments, the compound of formula I, or a pharmaceutically acceptable salt thereof, is administered simultaneously with the antibiotic agent. In certain embodiments, a composition (e.g., a pharmaceutical composition) comprising the compound of formula I, or pharmaceutically acceptable salt thereof, and the antibiotic agent is administered. In certain embodiments, the compound of formula I, or pharmaceutically acceptable salt thereof, and the antibiotic agent are administered sequentially. In certain embodiments, the compound of formula I, or pharmaceutically acceptable salt thereof, is administered first and the antibiotic agent is administered second. In certain embodiments, the antibiotic agent is administered first and the compound of formula I is administered second.

Certain embodiments of the invention provide a compound of formula I, or a pharmaceutically acceptable salt thereof, for the prophylactic or therapeutic treatment of bacterial vaginosis.

Certain embodiments of the invention provide a compound of formula I, or a pharmaceutically acceptable salt thereof, for the prophylactic or therapeutic treatment of bacterial vaginosis, in combination with an antibiotic agent (e.g., metronidazole).

Certain embodiments of the invention provide the use of a compound of formula I, or a pharmaceutically acceptable salt thereof, for the preparation of a medicament for treating bacterial vaginosis in a mammal (e.g., a human).

Certain embodiments of the invention provide the use of a compound of formula I, or a pharmaceutically acceptable salt thereof, to prepare a medicament for treating bacterial vaginosis in a mammal (e.g. a human), in combination with an antibiotic agent (e.g., metronidazole).

In certain embodiments, the bacterial vaginosis is caused by *Gardnerella vaginalis, Peptostreptococcus anaerobius, Mobiluncus curtisii*, and/or *Prevotella bivia*.

In certain embodiments, the bacterial vaginosis is caused by *Gardnerella vaginalis*.

Certain embodiments of the invention also provide a method for treating a bacterial infection in a mammal (e.g., a human) comprising administering to the mammal an effective amount of a compound of formula (I):

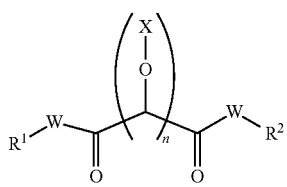
(I)

wherein:
R[1] is a polyether or a $(C_1-C_6)$alkyl that is substituted with one or more $NR_aR_b$;
R[2] is a polyether or a $(C_1-C_6)$alkyl that is substituted with one or more $NR_aR_b$;
each W is independently —NH—, —O— or —S—;
each X is independently $(C_1-C_{20})$alkyl or $(C_2-C_{20})$alkanoyl;
each $R_a$ is independently H or $(C_1-C_6)$alkyl;
each $R_b$ is independently H, $(C_1-C_6)$alkyl or —C(=NH)NH$_2$; and
n is 1, 2, 3, 4, 5, 6, 7, or 8;
or a pharmaceutically acceptable salt thereof,
wherein the bacterial infection is caused by *Gardnerella vaginalis*, *Peptostreptococcus anaerobius*, *Mobiluncus curtisii*, and/or *Prevotella bivia*.

In certain embodiments, the method further comprises administering a second therapeutic agent. In certain embodiments, the second therapeutic agent is an antibiotic agent. In certain embodiments, the antibiotic agent is clindamycin, metronidazole or tinidazole. In certain embodiments, the antibiotic agent is metronidazole.

Certain embodiments of the invention provide a compound of formula I, or a pharmaceutically acceptable salt thereof, for the prophylactic or therapeutic treatment of a bacterial infection, wherein the bacterial infection is caused by *Gardnerella vaginalis*, *Peptostreptococcus anaerobius*, *Mobiluncus curtisii*, and/or *Prevotella bivia*.

Certain embodiments of the invention provide a compound of formula I, or a pharmaceutically acceptable salt thereof, for the prophylactic or therapeutic treatment of a bacterial infection, in combination with an antibiotic agent (e.g., metronidazole), wherein the bacterial infection is caused by *Gardnerella vaginalis*, *Peptostreptococcus anaerobius*, *Mobiluncus curtisii*, and/or *Prevotella bivia*.

Certain embodiments of the invention provide the use of a compound of formula I, or a pharmaceutically acceptable salt thereof, for the preparation of a medicament for treating a bacterial infection in a mammal (e.g., a human), wherein the bacterial infection is caused by *Gardnerella vaginalis*, *Peptostreptococcus anaerobius*, *Mobiluncus curtisii*, and/or *Prevotella bivia*.

Certain embodiments of the invention provide the use of a compound of formula I, or a pharmaceutically acceptable salt thereof, for the preparation of a medicament for treating a bacterial infection in a mammal (e.g., a human), in combination with an antibiotic agent, wherein the bacterial infection is caused by *Gardnerella vaginalis*, *Peptostreptococcus anaerobius*, *Mobiluncus curtisii*, and/or *Prevotella bivia*.

In certain embodiments, the bacterial infection is caused by *Gardnerella vaginalis*.

Certain embodiments of the invention provide a pharmaceutical composition comprising a compound of formula I, or pharmaceutically acceptable salt thereof; an antibiotic agent; and a pharmaceutically acceptable carrier.

Certain embodiments of the invention provide a method for treating bacterial vaginosis in a mammal comprising administering to the mammal an effective amount of a pharmaceutical composition described herein.

Certain embodiments of the invention provide a pharmaceutical composition as described herein for the prophylactic or therapeutic treatment of bacterial vaginosis.

Certain embodiments of the invention provide the use of a pharmaceutical composition as described herein for the preparation of a medicament for treating bacterial vaginosis in a mammal (e.g. a human).

In certain embodiments, the bacterial vaginosis is caused by *Gardnerella vaginalis*, *Peptostreptococcus anaerobius*, *Mobiluncus curtisii*, and/or *Prevotella bivia*. In certain embodiments, the bacterial vaginosis is caused by *Gardnerella vaginalis*.

Certain embodiments of the invention provide a method for treating a bacterial infection in a mammal comprising administering to the mammal an effective amount of a pharmaceutical composition as described herein, wherein the bacterial infection is caused by *Gardnerella vaginalis*, *Peptostreptococcus anaerobius*, *Mobiluncus curtisii*, and/or *Prevotella bivia*.

Certain embodiments of the invention provide a pharmaceutical composition as described herein, for the prophylactic or therapeutic treatment of a bacterial infection, wherein the bacteria infection is caused by *Gardnerella vaginalis*, *Peptostreptococcus anaerobius*, *Mobiluncus curtisii*, and/or *Prevotella bivia*.

Certain embodiments of the invention provide the use of a pharmaceutical composition as described in herein, for the preparation of a medicament for treating a bacterial infection in a mammal, wherein the bacterial infection is caused by *Gardnerella vaginalis*, *Peptostreptococcus anaerobius*, *Mobiluncus curtisii*, and/or *Prevotella bivia*.

In certain embodiments, the bacterial infection is caused by *Gardnerella vaginalis*.

Certain embodiments of the invention provide a kit comprising a compound of formula I, or a pharmaceutically acceptable salt thereof, an antibiotic agent, packaging material, and instructions for administering the compound of formula I, or a pharmaceutically acceptable salt thereof, and the antibiotic agent to a mammal to treat a bacterial infection.

In certain embodiments, the bacterial infection is bacterial vaginosis.

In certain embodiments, the antibiotic agent is clindamycin, metronidazole or tinidazole. In certain embodiments, the antibiotic agent is metronidazole.

Certain embodiments of the invention provide a method for inhibiting a biofilm comprising contacting the biofilm with an effective amount of a compound of formula I, or a salt thereof. In certain embodiments, the biofilm is a *Gardnerella vaginalis* biofilm. In certain embodiments, a lactobacilli biofilm is not inhibited.

In certain embodiments, each $R_a$ is independently H. In certain embodiments, each $R_a$ is independently $(C_1-C_6)$alkyl.

In certain embodiments, each $R_b$ is independently H. In certain embodiments, each $R_b$ is independently $(C_1-C_6)$alkyl. In certain embodiments, each $R_b$ is independently —C(=NH)NH$_2$.

In certain embodiments, n is 2. In certain embodiments, n is 3. In certain embodiments, n is 4. In certain embodiments, n is 5.

In certain embodiments, variables R[1], R[2] and W are defined as any value described herein.

In certain embodiments, a compound of formula I is a compound of formula (Ia):

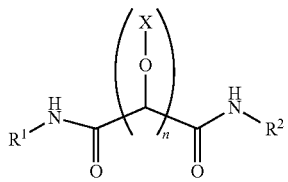

wherein:
R$^1$ is a polyether or a (C$_1$-C$_6$)alkyl that is substituted with one or more NR$_a$R$_b$;
R$^2$ is a polyether or a (C$_1$-C$_6$)alkyl that is substituted with one or more NR$_a$R$_b$;
each X is independently (C$_1$-C$_{20}$)alkyl or (C$_2$-C$_{20}$)alkanoyl;
each R$_a$ is independently H or (C$_1$-C$_6$)alkyl;
each R$_b$ is independently H, (C$_1$-C$_6$)alkyl or —C(=NH)NH$_2$; and
n is 1, 2, 3, 4, 5, 6, 7, or 8;
or a pharmaceutically acceptable salt thereof.

In certain embodiments, a compound of formula I is a compound of formula Ib:

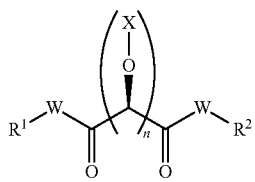

wherein:
R$^1$ is a polyether or a (C$_1$-C$_6$)alkyl that is substituted with one or more NR$_a$R$_b$;
R$^2$ is a polyether or a (C$_1$-C$_6$)alkyl that is substituted with one or more NR$_a$R$_b$;
each W is independently —NH—, —O— or —S—;
each X is independently (C$_1$-C$_{20}$)alkyl or (C$_2$-C$_{20}$)alkanoyl;
R$_a$ is each independently H or (C$_1$-C$_6$)alkyl;
R$_b$ is each independently H, (C$_1$-C$_6$)alkyl or —C(=NH)NH$_2$; and
n is 1, 2, 3, 4, 5, 6, 7, or 8;
or a pharmaceutically acceptable salt thereof.

In certain embodiments, a compound of formula I is a compound of formula Ib':

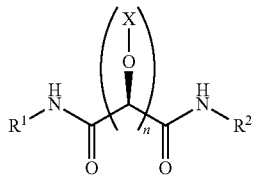

wherein:
R$^1$ is a polyether or a (C$_1$-C$_6$)alkyl that is substituted with one or more NR$_a$R$_b$;
R$^2$ is a polyether or a (C$_1$-C$_6$)alkyl that is substituted with one or more NR$_a$R$_b$;
each X is independently (C$_1$-C$_{20}$)alkyl or (C$_2$-C$_{20}$)alkanoyl;
R$_a$ is each independently H or (C$_1$-C$_6$)alkyl;
R$_b$ is each independently H, (C$_1$-C$_6$)alkyl or —C(=NH)NH$_2$; and
n is 1, 2, 3, 4, 5, 6, 7, or 8;
or a pharmaceutically acceptable salt thereof.

In certain embodiments, a compound of formula I is a compound of formula Ic:

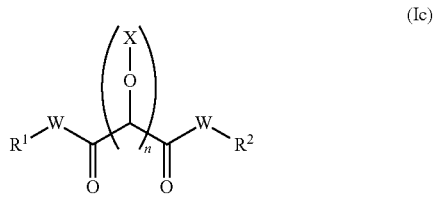

wherein:
R$^1$ is a polyether or a (C$_1$-C$_6$)alkyl that is substituted with one or more NR$_a$R$_b$;
R$^2$ is a polyether or a (C$_1$-C$_6$)alkyl that is substituted with one or more NR$_a$R$_b$;
each W is independently —NH—, —O— or —S—;
each R$_a$ is H; and
each R$_b$ is H;
or a pharmaceutically acceptable salt thereof.

In certain embodiments, a compound of formula I is a compound of formula Ic':

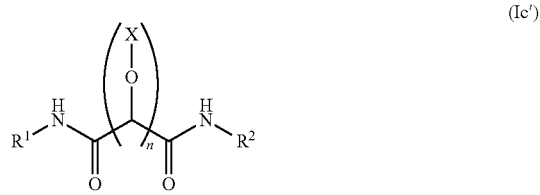

wherein:
R$^1$ is a polyether or a (C$_1$-C$_6$)alkyl that is substituted with one or more NR$_a$R$_b$;
R$^2$ is a polyether or a (C$_1$-C$_6$)alkyl that is substituted with one or more NR$_a$R$_b$;
each R$_a$ is H; and
each R$_b$ is H;
or a pharmaceutically acceptable salt thereof.

In certain embodiments, a compound of formula I is a compound of formula Id:

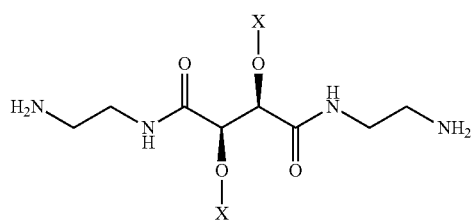

(Id)

or a salt thereof.

In certain embodiments of compounds of formula I, each X is independently $(C_1-C_{20})$alkyl. In certain embodiments, each X is independently $(C_2-C_{20})$alkyl. In certain embodiments, each X is independently $(C_4-C_{14})$alkyl. In certain embodiments, each X is independently $(C_6-C_{12})$alkyl. In certain embodiments, each X is independently $(C_6)$alkyl. In certain embodiments, each X is independently $(C_7)$alkyl. In certain embodiments, each X is independently $(C_8)$alkyl. In certain embodiments, each X is independently $(C_9)$alkyl. In certain embodiments, each X is independently $(C_{10})$alkyl. In certain embodiments, each X is independently $(C_{11})$alkyl. In certain embodiments, each X is independently $(C_{12})$alkyl. In certain embodiments, each X is independently $(C_{13})$alkyl. In certain embodiments, each X is independently $(C_{14})$alkyl.

In certain embodiments, a compound of formula (I) is selected from:

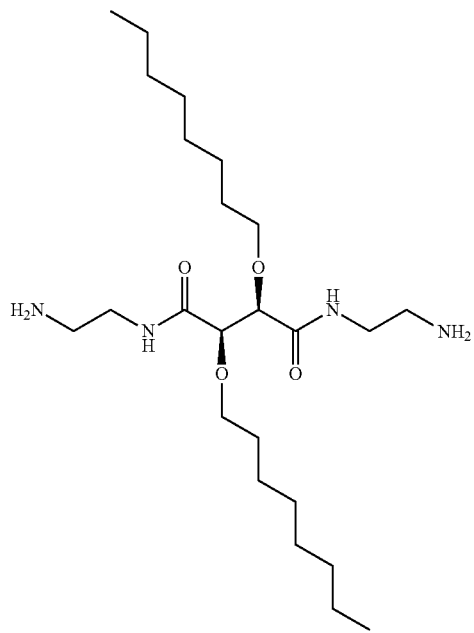

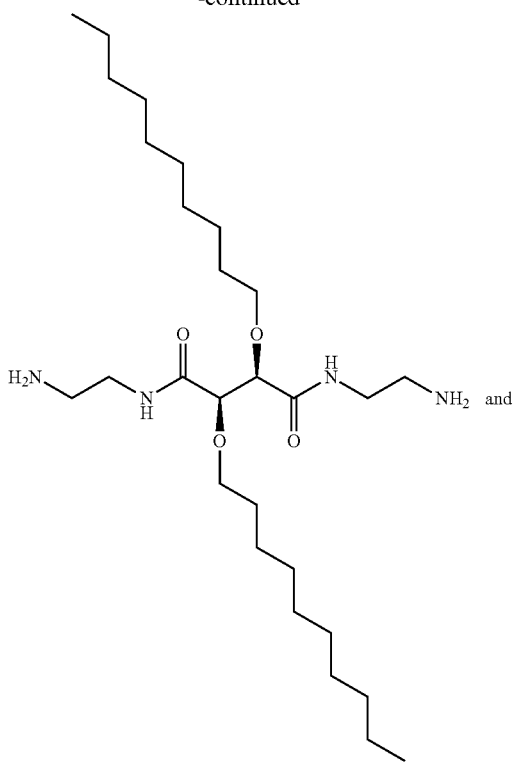

and

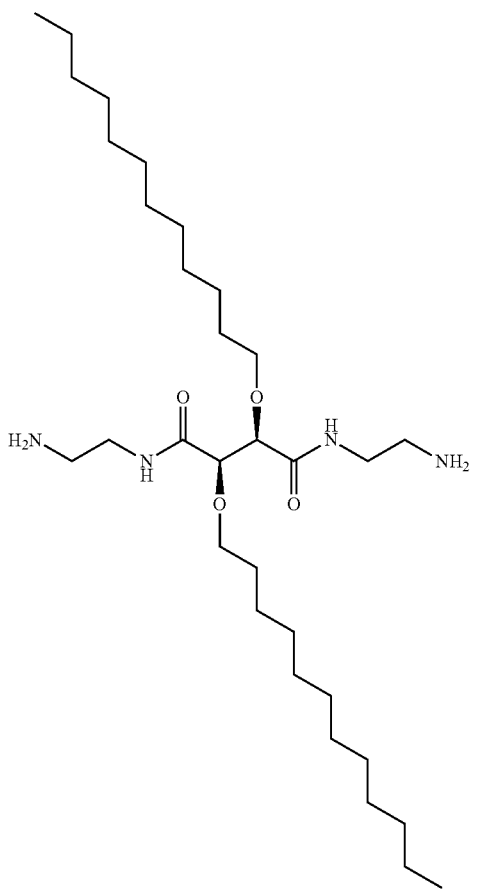 [SMILES: CCCCCCCCCCCCO[C@@H](C(=O)NCCN)[C@@H](OCCCCCCCCCCCC)C(=O)NCCN]

and pharmaceutically acceptable salts thereof.

In certain embodiments, a compound of formula (I) is:
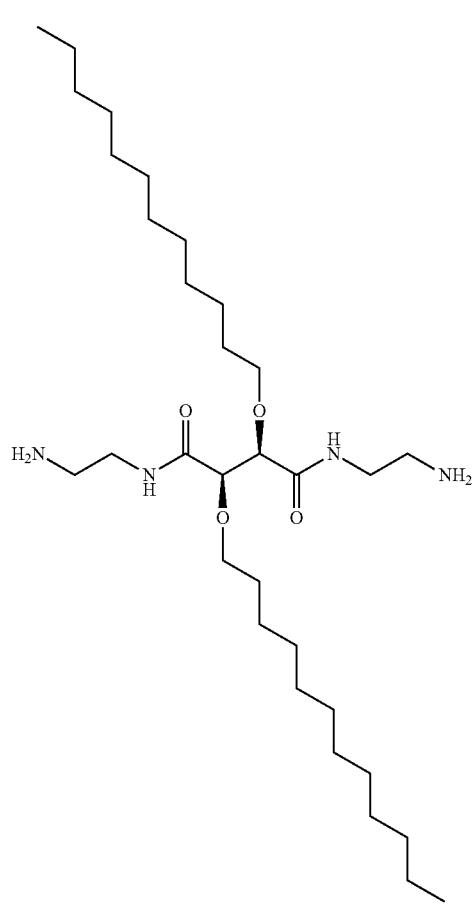
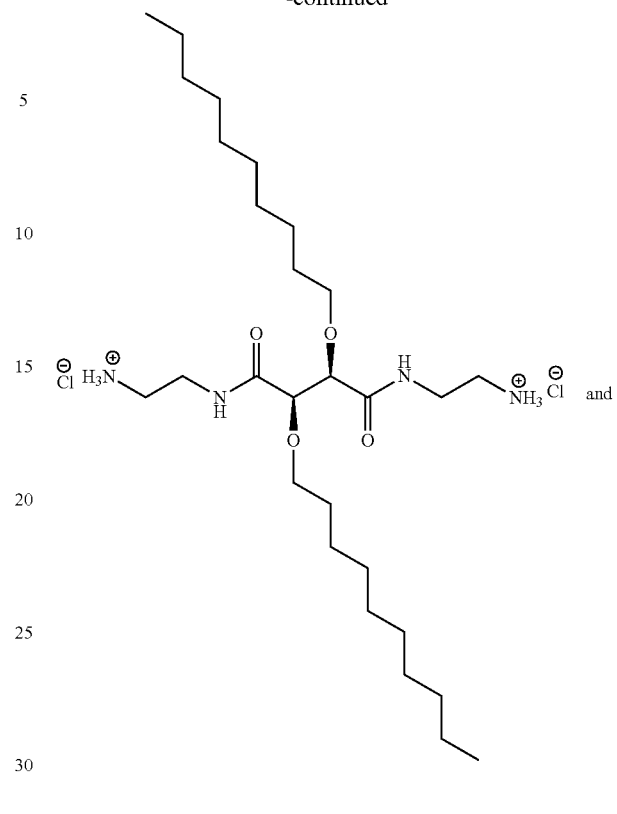
or a pharmaceutically acceptable salt thereof.
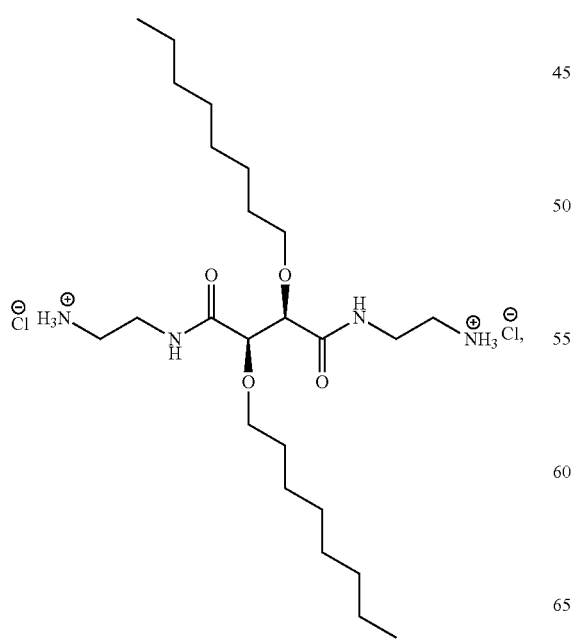

In certain embodiments, a compound of formula I is

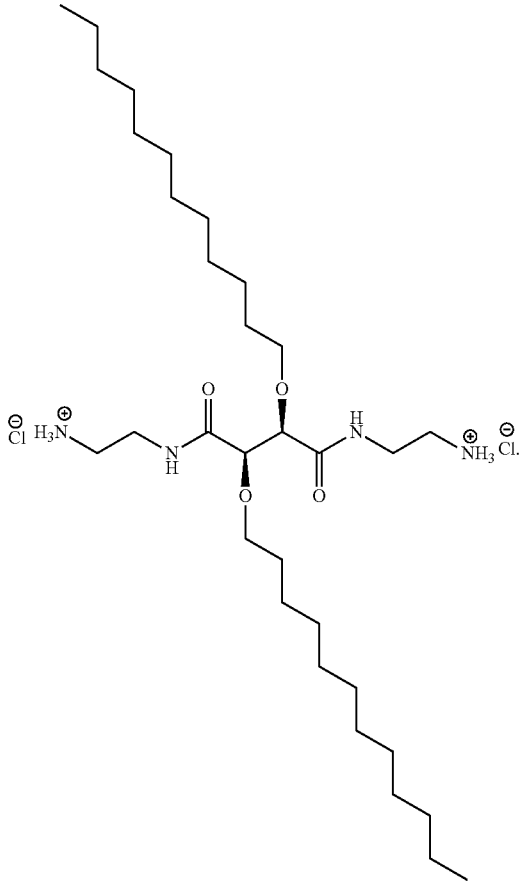

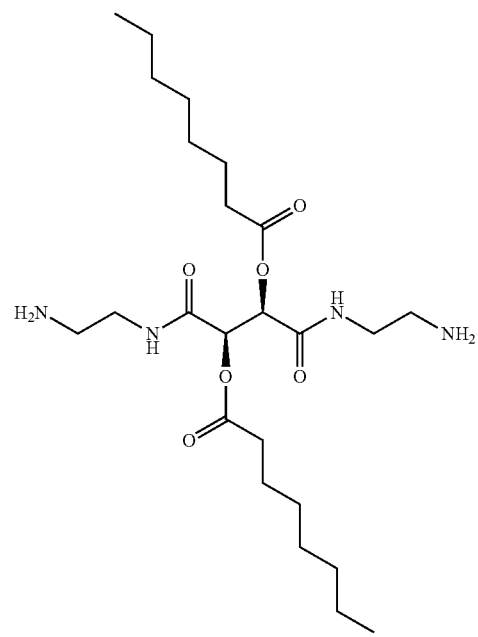

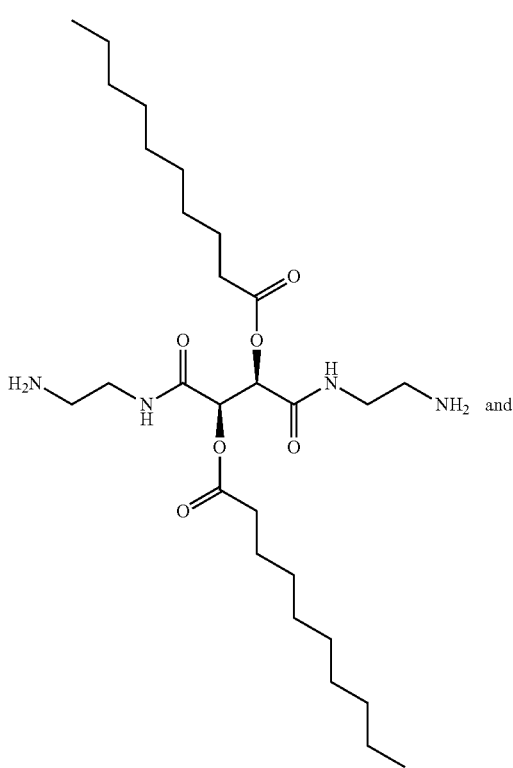

In certain embodiments of compounds of formula I, each X is independently $(C_2-C_{20})$alkanoyl. In certain embodiments, each X is independently $(C_4-C_{14})$alkanoyl. In certain embodiments, each X is independently $(C_6-C_{12})$alkanoyl. In certain embodiments, each X is independently $(C_8-C_{12})$alkanoyl. In certain embodiments, each X is independently $(C_6)$alkanoyl. In certain embodiments, each X is independently $(C_7)$alkanoyl. In certain embodiments, each X is independently $(C_8)$alkanoyl. In certain embodiments, each X is independently $(C_9)$alkanoyl. In certain embodiments, each X is independently $(C_{10})$alkanoyl. In certain embodiments, each X is independently $(C_{11})$alkanoyl. In certain embodiments, each X is independently $(C_{12})$alkanoyl. In certain embodiments, each X is independently $(C_{13})$alkanoyl. In certain embodiments, each X is independently $(C_{14})$alkanoyl.

In certain embodiments, a compound of formula (I) is selected from:

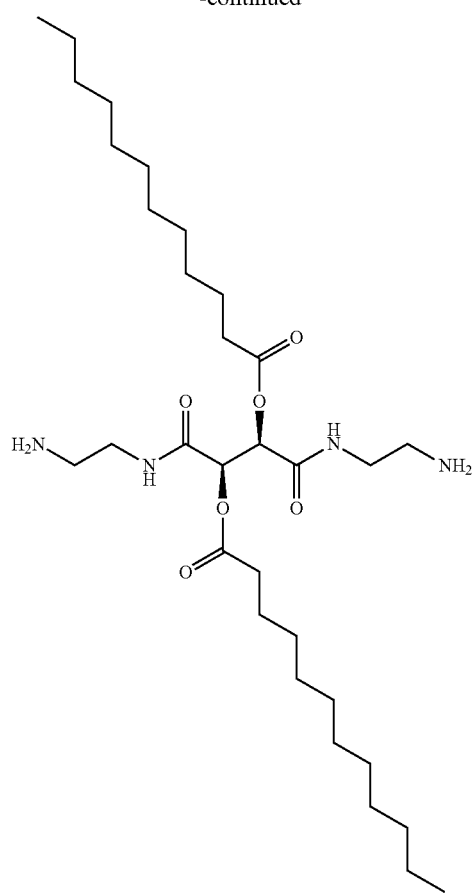
and pharmaceutically acceptable salts thereof.
In certain embodiments, a compound of formula (I) is selected from:
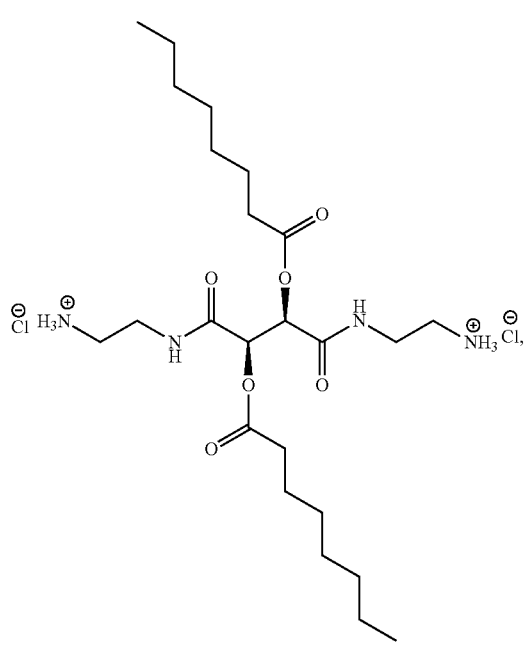
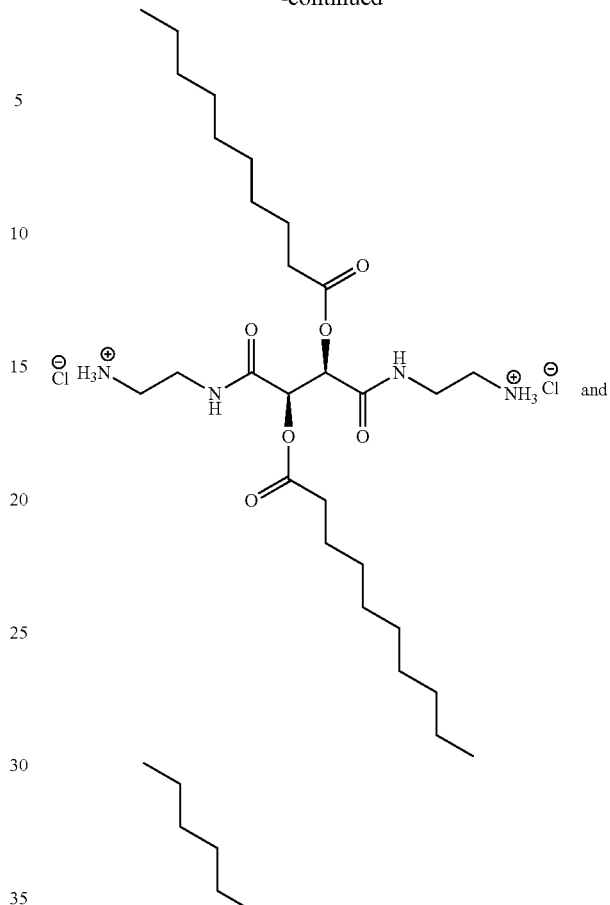
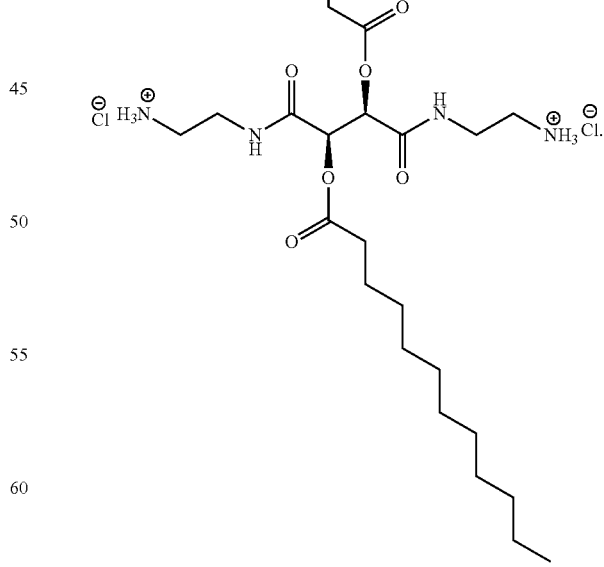
Compounds of Formula (II)
Certain embodiments of the invention also provide a method for treating bacterial vaginosis in a mammal (e.g., a human) comprising administering to the mammal an effective amount of a compound of formula (II):

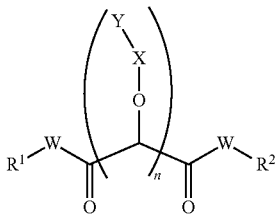

wherein:
R¹ is a polyether or a (C₁-C₆)alkyl that is optionally substituted with one or more NR$_a$R$_b$;
R² is a polyether or a (C₁-C₆)alkyl that is optionally substituted with one or more NR$_a$R$_b$;
each W is independently —NH—, —O— or —S—;
each X is independently (C₂-C₂₀)alkyl or (C₂-C₂₀)alkanoyl;
R$_a$ and R$_b$ are each independently H or (C₁-C₆)alkyl;
each Y is independently —NH₂, —N⁺(R$^c$)₃Z⁻, —NH—C(=NH)—NH₂ or —NH—BOC;
each R$^c$ is independently (C₁-C₆)alkyl;
Z is a counter ion; and
n is 1, 2, 3, 4, 5, 6, 7, or 8;
or a pharmaceutically acceptable salt thereof.

In certain embodiments, the method further comprises administering a second therapeutic agent. In certain embodiments, the second therapeutic agent is an antibiotic agent. In certain embodiments, the antibiotic agent is clindamycin, metronidazole or tinidazole. In certain embodiments, the antibiotic agent is metronidazole.

The compound of formula II, or a pharmaceutically acceptable salt thereof, and the antibiotic agent (e.g., metronidazole) may be administered either simultaneously or sequentially. In certain embodiments, the compound of formula II, or a pharmaceutically acceptable salt thereof, is administered simultaneously with the antibiotic agent. In certain embodiments, a composition (e.g., a pharmaceutical composition) comprising the compound of formula II, or pharmaceutically acceptable salt thereof, and the antibiotic agent is administered. In certain embodiments, the compound of formula II, or pharmaceutically acceptable salt thereof, and the antibiotic agent are administered sequentially. In certain embodiments, the compound of formula II, or pharmaceutically acceptable salt thereof, is administered first and the antibiotic agent is administered second. In certain embodiments, the antibiotic agent is administered first and the compound of formula II is administered second.

Certain embodiments of the invention provide a compound of formula II, or a pharmaceutically acceptable salt thereof, for the prophylactic or therapeutic treatment of bacterial vaginosis.

Certain embodiments of the invention provide a compound of formula II, or a pharmaceutically acceptable salt thereof, for the prophylactic or therapeutic treatment of bacterial vaginosis, in combination with an antibiotic agent.

Certain embodiments of the invention provide the use of a compound of formula II, or a pharmaceutically acceptable salt thereof, for the preparation of a medicament for treating bacterial vaginosis in a mammal (e.g., a human).

Certain embodiments of the invention provide the use of a compound of formula II, or a pharmaceutically acceptable salt thereof, for the preparation of a medicament for treating bacterial vaginosis in a mammal (e.g., a human), in combination with an antibiotic agent.

In certain embodiments, the bacterial vaginosis is caused by Gardnerella vaginalis, Peptostreptococcus anaerobius, Mobiluncus curtisii, and/or Prevotella bivia.

In certain embodiments, the bacterial vaginosis is caused by Gardnerella vaginalis.

In certain embodiments, the antibiotic agent is metronidazole.

Certain embodiments of the invention also provide a method for treating a bacterial infection in a mammal (e.g., a human) comprising administering to the mammal an effective amount of a compound of formula (II):

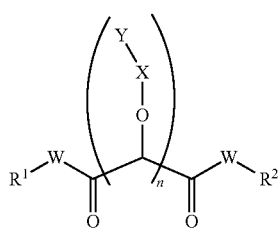

wherein:
R¹ is a polyether or a (C₁-C₆)alkyl that is optionally substituted with one or more NR$_a$R$_b$;
R² is a polyether or a (C₁-C₆)alkyl that is optionally substituted with one or more NR$_a$R$_b$;
each W is independently —NH—, —O— or —S—;
each X is independently (C₂-C₂₀)alkyl or (C₂-C₂₀)alkanoyl;
R$_a$ and R$_b$ are each independently H or (C₁-C₆)alkyl;
each Y is independently —NH₂, —N⁺(R$^c$)₃Z⁻, —NH—C(=NH)—NH₂ or —NH—BOC;
each R$^c$ is independently (C₁-C₆)alkyl;
Z is a counter ion; and
n is 1, 2, 3, 4, 5, 6, 7, or 8;
or a pharmaceutically acceptable salt thereof,
wherein the bacterial infection is caused by Gardnerella vaginalis, Peptostreptococcus anaerobius, Mobiluncus curtisii, and/or Prevotella bivia.

In certain embodiments, the method further comprises administering a second therapeutic agent. In certain embodiments, the second therapeutic agent is an antibiotic agent. In certain embodiments, the antibiotic agent is clindamycin, metronidazole or tinidazole. In certain embodiments, the antibiotic agent is metronidazole.

Certain embodiments of the invention provide a compound of formula II, or a pharmaceutically acceptable salt thereof, for the prophylactic or therapeutic treatment of a bacterial infection, wherein the bacterial infection is caused by Gardnerella vaginalis, Peptostreptococcus anaerobius, Mobiluncus curtisii, and/or Prevotella bivia.

Certain embodiments of the invention provide a compound of formula II, or a pharmaceutically acceptable salt thereof, for the prophylactic or therapeutic treatment of a bacterial infection, in combination with an antibiotic agent, wherein the bacterial infection is caused by Gardnerella vaginalis, Peptostreptococcus anaerobius, Mobiluncus curtisii, and/or Prevotella bivia.

Certain embodiments of the invention provide the use of a compound of formula II, or a pharmaceutically acceptable salt thereof, for the preparation of a medicament for treating a bacterial infection in a mammal (e.g., a human), wherein the bacterial infection is caused by *Gardnerella vaginalis, Peptostreptococcus anaerobius, Mobiluncus curtisii*, and/or *Prevotella bivia*.

Certain embodiments of the invention provide the use of a compound of formula II, or a pharmaceutically acceptable salt thereof, for the preparation of a medicament for treating a bacterial infection in a mammal (e.g., a human), in combination with an antibiotic agent, wherein the bacterial infection is caused by *Gardnerella vaginalis, Peptostreptococcus anaerobius, Mobiluncus curtisii*, and/or *Prevotella bivia*.

In certain embodiments, the bacterial infection is caused by *Gardnerella vaginalis*.

In certain embodiments, the antibiotic agent is metronidazole.

Certain embodiments of the invention provide a pharmaceutical composition comprising a compound of formula II, or pharmaceutically acceptable salt thereof, an antibiotic agent, and a pharmaceutically acceptable carrier.

In certain embodiments, the antibiotic agent is metronidazole.

Certain embodiments of the invention provide a method for treating bacterial vaginosis in a mammal comprising administering to the mammal an effective amount of a pharmaceutical composition described herein.

Certain embodiments of the invention provide a pharmaceutical composition described herein for the prophylactic or therapeutic treatment of a bacterial vaginosis.

Certain embodiments of the invention provide a pharmaceutical composition described herein for the preparation of a medicament for treating bacterial vaginosis in a mammal.

In certain embodiments, the bacterial vaginosis is caused by *Gardnerella vaginalis, Peptostreptococcus anaerobius, Mobiluncus curtisii*, and/or *Prevotella bivia*.

In certain embodiments, the bacterial vaginosis is caused by *Gardnerella vaginalis*.

Certain embodiments of the invention provide a method for treating a bacterial infection in a mammal comprising administering to the mammal an effective amount of a pharmaceutical composition described herein, wherein the bacterial infection is caused by *Gardnerella vaginalis, Peptostreptococcus anaerobius, Mobiluncus curtisii*, and/or *Prevotella bivia*.

Certain embodiments of the invention provide a pharmaceutical composition as described herein, for the prophylactic or therapeutic treatment of a bacterial infection, wherein the bacteria infection is caused by *Gardnerella vaginalis, Peptostreptococcus anaerobius, Mobiluncus curtisii*, and/or *Prevotella bivia*.

Certain embodiments of the invention provide the use of a pharmaceutical composition as described herein, for the preparation of a medicament for treating a bacterial infection in a mammal, wherein the bacterial infection is caused by *Gardnerella vaginalis, Peptostreptococcus anaerobius, Mobiluncus curtisii*, and/or *Prevotella bivia*.

In certain embodiments, the bacterial infection is caused by *Gardnerella vaginalis*.

Certain embodiments of the invention provide a kit comprising a compound of formula II, or a pharmaceutically acceptable salt thereof, an antibiotic agent, packaging material, and instructions for administering the compound of formula II, or a pharmaceutically acceptable salt thereof, and the antibiotic agent to a mammal to treat a bacterial infection.

In certain embodiments, the antibiotic agent is clindamycin, metronidazole or tinidazole. In certain embodiments, the antibiotic agent is metronidazole.

In certain embodiments, the bacterial infection is bacterial vaginosis.

Certain embodiments of the invention provide a method for inhibiting a biofilm comprising contacting the biofilm with an effective amount of a compound of formula II, or a salt thereof. In certain embodiments, the biofilm is a *Gardnerella vaginalis* biofilm. In certain embodiments, a lactobacilli biofilm is not inhibited.

In certain embodiments, each Y is independently —NH$_2$.

In certain embodiments, each Y is independently —N$^+$(R$^c$)$_3$Z$^-$.

In certain embodiments, each Y is independently —NH—C(=NH)—NH$_2$.

In certain embodiments, each Y is independently —NH—BOC.

In certain embodiments, each R$_a$ is independently H. In certain embodiments, each R$_a$ is independently (C$_1$-C$_6$)alkyl.

In certain embodiments, each R$_b$ is independently H. In certain embodiments, each R$_b$ is independently (C$_1$-C$_6$)alkyl.

In certain embodiments, n is 2. In certain embodiments, n is 3. In certain embodiments, n is 4. In certain embodiments, n is 5.

In certain embodiments, variables R$^1$, R$^2$, R$^c$, W and Z are defined as any value described herein.

In certain embodiments, a compound of formula II is a compound of formula IIa:

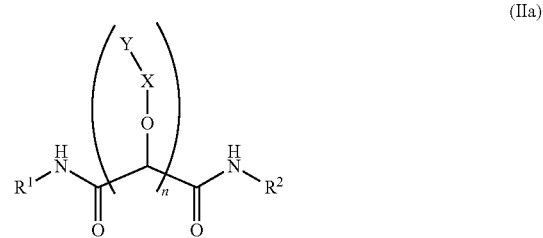

(IIa)

wherein:

R$^1$ is a polyether or a (C$_1$-C$_6$)alkyl that is optionally substituted with one or more NR$_a$R$_b$;

R$^2$ is a polyether or a (C$_1$-C$_6$)alkyl that is optionally substituted with one or more NR$_a$R$_b$;

each X is independently (C$_2$-C$_{20}$)alkyl or (C$_2$-C$_{20}$)alkanoyl;

R$_a$ and R$_b$ are each independently H or (C$_1$-C$_6$)alkyl;

each Y is independently —NH$_2$, —N$^+$(R$^c$)$_3$Z$^-$, —NH—C(=NH)—NH$_2$ or —NH—BOC;

each R$^c$ is independently (C$_1$-C$_6$)alkyl;

Z is a counter ion; and n is 1, 2, 3, 4, 5, 6, 7, or 8;

or a pharmaceutically acceptable salt thereof.

In certain embodiments, a compound of formula II is a compound of formula IIb:

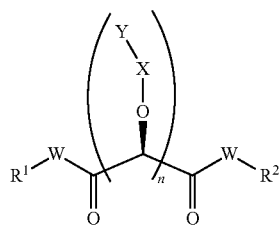
(IIb)

wherein:

$R^1$ is a polyether or a $(C_1\text{-}C_6)$alkyl that is optionally substituted with one or more $NR_aR_b$;

$R^2$ is a polyether or a $(C_1\text{-}C_6)$alkyl that is optionally substituted with one or more $NR_aR_b$;

each W is independently —NH—, —O— or —S—;

each X is independently $(C_2\text{-}C_{20})$alkyl or $(C_2\text{-}C_{20})$alkanoyl;

$R_a$ and $R_b$ are each independently H or $(C_1\text{-}C_6)$alkyl;

each Y is independently —NH$_2$, —N$^+$(R$^c$)$_3$Z$^-$, —NH—C(=NH)—NH$_2$ or —NH—BOC;

each $R^c$ is independently $(C_1\text{-}C_6)$alkyl;

Z is a counter ion; and n is 1, 2, 3, 4, 5, 6, 7, or 8;

or a pharmaceutically acceptable salt thereof.

In certain embodiments, a compound of formula II is a compound of formula IIb':

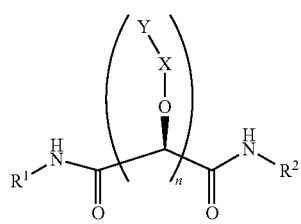
(IIb')

wherein:

$R^1$ is a polyether or a $(C_1\text{-}C_6)$alkyl that is optionally substituted with one or more $NR_aR_b$;

$R^2$ is a polyether or a $(C_1\text{-}C_6)$alkyl that is optionally substituted with one or more $NR_aR_b$;

each X is independently $(C_2\text{-}C_{20})$alkyl or $(C_2\text{-}C_{20})$alkanoyl;

$R_a$ and $R_b$ are each independently H or $(C_1\text{-}C_6)$alkyl;

each Y is independently —NH$_2$, —N$^+$(R$^c$)$_3$Z$^-$, —NH—C(=NH)—NH$_2$ or —NH—BOC;

each $R^c$ is independently $(C_1\text{-}C_6)$alkyl;

Z is a counter ion; and n is 1, 2, 3, 4, 5, 6, 7, or 8;

or a pharmaceutically acceptable salt thereof.

In certain embodiments, a compound of formula II is a compound of formula IIc:

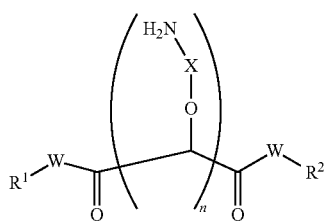
(IIc)

wherein:

each W is independently —NH—, —O— or —S—;

$R^1$ is a polyether or a $(C_1\text{-}C_6)$alkyl; and $R^2$ is a polyether or a $(C_1\text{-}C_6)$alkyl;

or a salt thereof.

In certain embodiments, a compound of formula II is a compound of formula IIc':

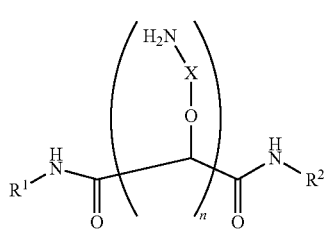
(IIc')

wherein:

$R^1$ is a polyether or a $(C_1\text{-}C_6)$alkyl; and $R^2$ is a polyether or a $(C_1\text{-}C_6)$alkyl;

or a pharmaceutically acceptable salt thereof.

In certain embodiments, a compound of formula II is a compound of formula IIc":

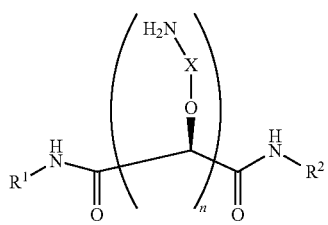
(IIc")

wherein:

$R^1$ is a polyether or a $(C_1\text{-}C_6)$alkyl; and $R^2$ is a polyether or a $(C_1\text{-}C_6)$alkyl;

or a pharmaceutically acceptable salt thereof.

In certain embodiments, a compound of formula II is a compound of formula IId:

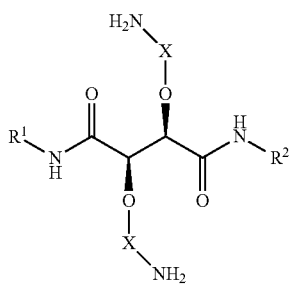

(IId)

or a pharmaceutically acceptable salt thereof.

In certain embodiments of compounds of formula II, each X is independently $(C_1-C_{20})$alkyl. In certain embodiments, each X is independently $(C_2-C_{20})$alkyl. In certain embodiments, each X is independently $(C_4-C_{14})$alkyl. In certain embodiments, each X is independently $(C_6-C_{12})$alkyl. In certain embodiments, each X is independently $(C_8-C_{12})$alkyl. In certain embodiments, each X is independently $(C_6)$alkyl. In certain embodiments, each X is independently $(C_7)$alkyl. In certain embodiments, each X is independently $(C_8)$alkyl. In certain embodiments, each X is independently $(C_9)$alkyl. In certain embodiments, each X is independently $(C_{10})$alkyl. In certain embodiments, each X is independently $(C_{11})$alkyl. In certain embodiments, each X is independently $(C_{12})$alkyl. In certain embodiments, each X is independently $(C_{13})$alkyl. In certain embodiments, each X is independently $(C_{14})$alkyl.

In certain embodiments, a compound of formula II is selected from:

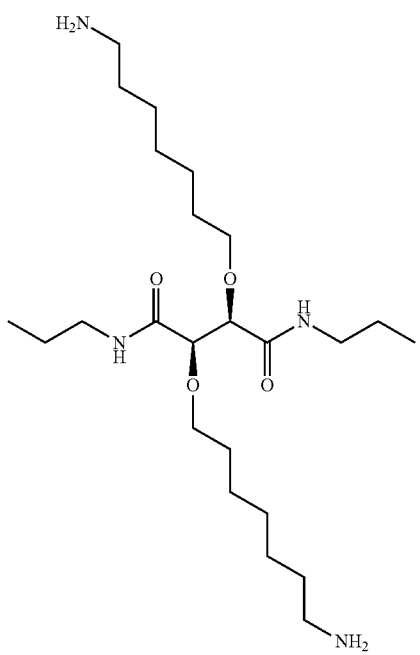

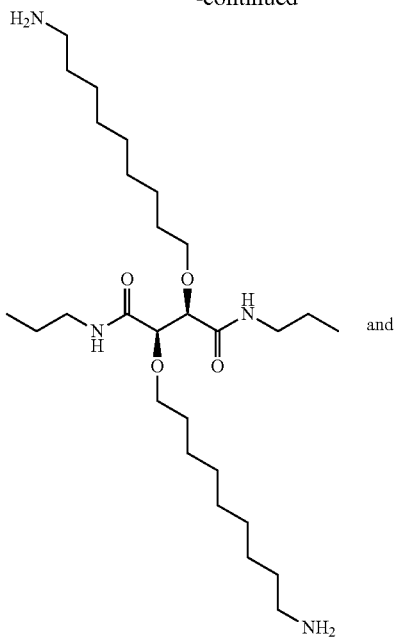

and

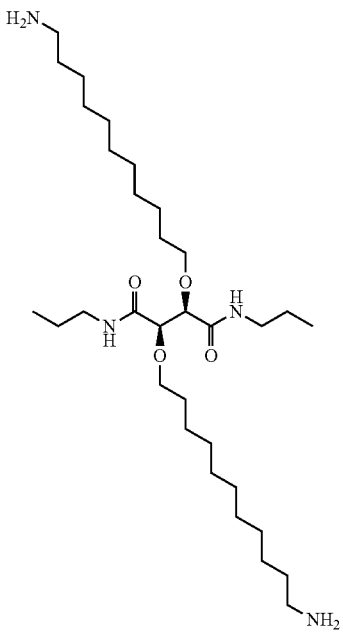 [SMILES: CCCNC(=O)[C@H](OCCCCCCCCCCCN)[C@@H](OCCCCCCCCCCCN)C(=O)NCCC]

and pharmaceutically acceptable salts thereof.

In certain embodiments, a compound of formula II is selected from:

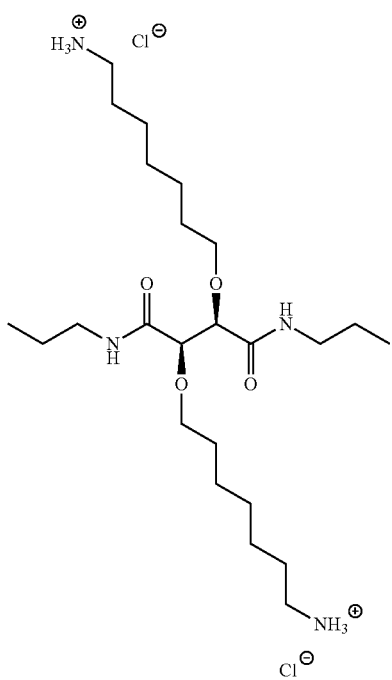

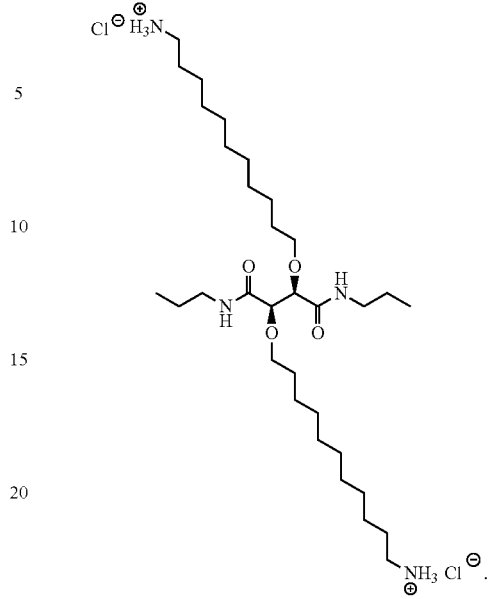

In certain embodiments of compounds of formula II, each X is independently $(C_2-C_{20})$alkanoyl. In certain embodiments, each X is independently $(C_4-C_{14})$alkanoyl. In certain embodiments, each X is independently $(C_6-C_{12})$alkanoyl. In certain embodiments, each X is independently $(C_8-C_{12})$alkanoyl. In certain embodiments, each X is independently $(C_6)$alkanoyl. In certain embodiments, each X is independently $(C_7)$alkanoyl. In certain embodiments, each X is independently $(C_8)$alkanoyl. In certain embodiments, each X is independently $(C_9)$alkanoyl. In certain embodiments, each X is independently $(C_{10})$alkanoyl. In certain embodiments, each X is independently $(C_{11})$alkanoyl. In certain embodiments, each X is independently $(C_{12})$alkanoyl. In certain embodiments, each X is independently $(C_{13})$alkanoyl. In certain embodiments, each X is independently $(C_{14})$alkanoyl.

In certain embodiments, a compound of formula II is selected from:

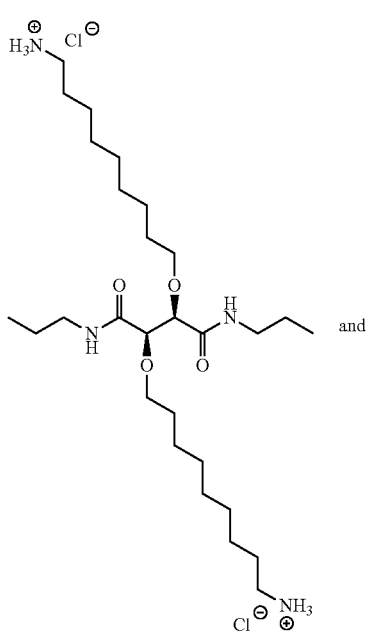 and

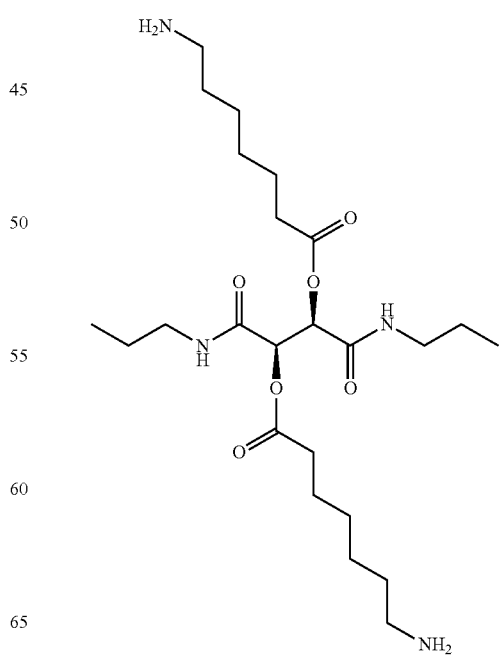

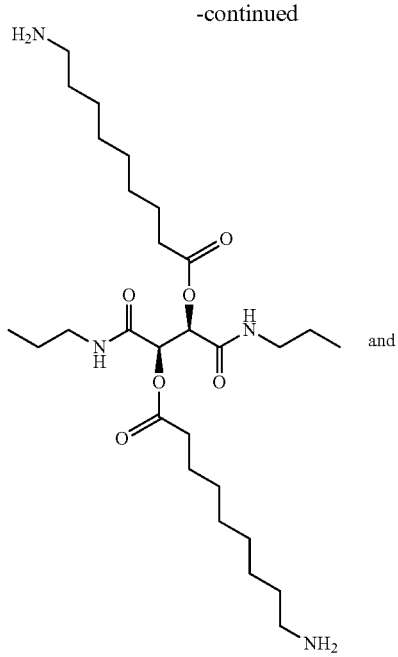
and
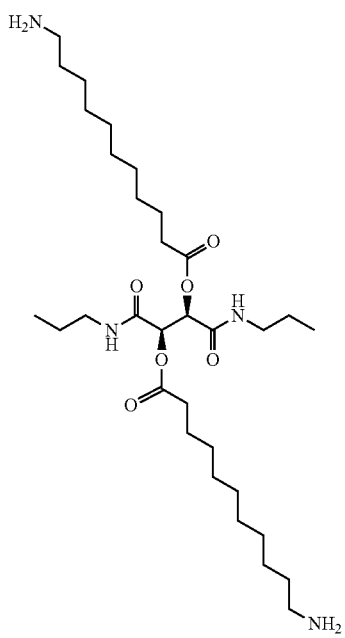 [SMILES: CCCNC(=O)[C@H](OC(=O)CCCCCCCCCCN)[C@@H](OC(=O)CCCCCCCCCCN)C(=O)NCCC]
and pharmaceutically acceptable salts thereof.
In certain embodiments, a compound of formula II is selected from:
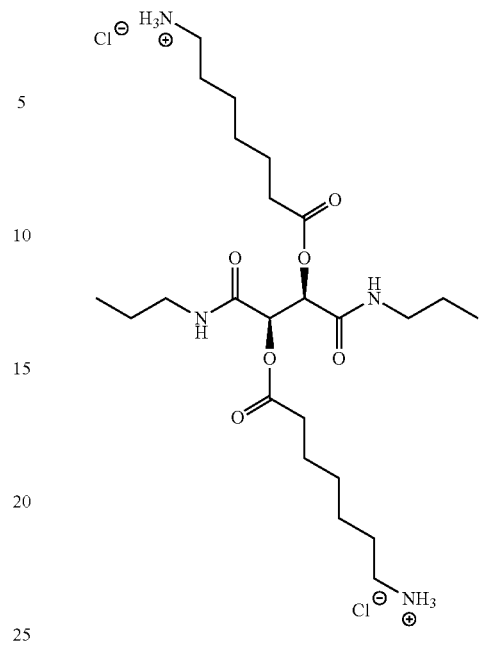
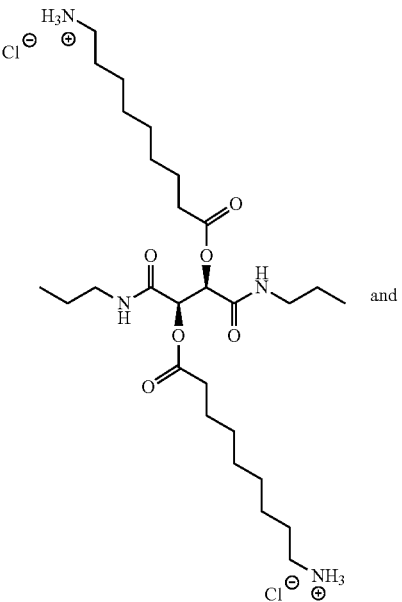
and -continued

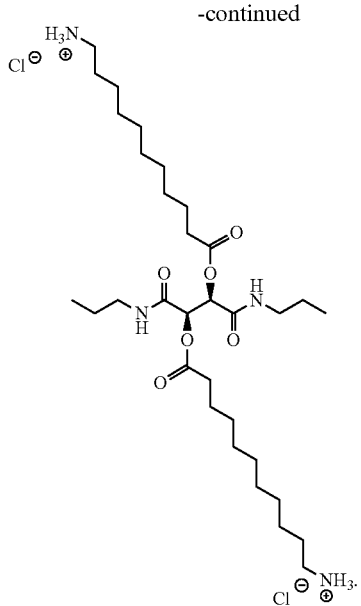

Certain Definitions

The following definitions are used, unless otherwise described: halo is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to. An alkanoyl is an alkyl-(C=O)—.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

Specific values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl.

As used herein the term "Boc" refers to —C(=O)OC$(CH_3)_3$.

As used herein the term "salt" includes base addition, acid addition and quaternary salts. Compounds of the invention which are acidic can form salts, including pharmaceutically acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris(hydroxymethyl)amino-methane, L-arginine, L-lysine, N-ethyl piperidine, dibenzylamine and the like. Those compounds which are basic can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic, p-toluenesulphonic, benzoic, benzenesulfonic, glutamic, lactic, and mandelic acids and the like. For a review on suitable salts, see Handbook of Pharmaceutical Salts: Properties, Selection, and Use by Stahl and Wermuth (Wiley-VCH, Weinheim, Germany, 2002).

In cases where compounds are sufficiently basic or acidic, a salt of a compound of formula I or II can be useful as an intermediate for isolating or purifying a compound of formula I or II. Additionally, administration of a compound of the invention as a pharmaceutically acceptable acid or base salt may be appropriate. Pharmaceutically acceptable salts may be obtained using standard procedures well known in the art.

The terms "treat" and "treatment" refer to both therapeutic treatment and prophylactic or preventative measures, wherein the object is to prevent or slow down (lessen) an undesired physiological change or disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

Administration of Compounds of Formula I or II

As described herein, a compound of formula I, or a pharmaceutically acceptable salt thereof, or a compound of formula II, or a pharmaceutically acceptable salt thereof, can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I or II to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I or II can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Generally, compounds of formula I, as well as synthetic intermediates that can be used for preparing compounds of formula I, can be prepared as illustrated in Scheme 1 and Example 1. The antibiotic properties of a compound may be determined using pharmacological models which are well known to the art, or using assays described in the Examples below.

The invention will now be illustrated by the following non-limiting Examples.

Example 1

Using antimicrobials to combat infectious diseases has been a common practice since the 1940s. However, the emergence of multidrug-resistant bacteria due to overuse and misuse of antimicrobial agents has become a severe threat to public health. Compared to conventional antibiotics which target a specific biochemical process (e.g., DNA synthesis, protein synthesis) or molecule (e.g., enzyme), naturally occurring antimicrobial peptides (AMPs), as part of innate immune defense, have received substantial interest owing to their broad-spectrum activities, minimum cytotoxicity against host cells, and unique cellular membrane targeting mechanism. The lack of a specific cellular target reduces the likelihood of developing resistance from a genetic mutation(s), and thus, AMPs hold great potential for the treatment of microbial infections as antibiotics alternatives.

Despite diverse primary peptide sequences and secondary structures displayed by AMPs, two characteristics they share in common are cationic residues and hydrophobic domains, resulting in their amphiphilic topology. Recent literature suggests that the biological activities of AMPs mainly depend on their physicochemical properties rather than specific amino acid sequences. The cationic charges are important to promote the electrostatic interaction with the negatively charged bacterial membranes. Subsequently, the hydrophobic residues insert themselves into the hydrophobic core of the membranes, which leads to membrane disintegration and lysis, leakage of the cytoplasm, and eventually cell death. However, intrinsic drawbacks associated with AMPs, including low metabolic stability, high manufacture cost, and formulation difficulties, have precluded their success in preclinical and clinical settings.

Inspired by natural AMPs, a variety of structurally diverse synthetic mimics with key physicochemical properties (i.e., cationic charges and amphiphilicity) have been designed, synthesized, and investigated, such as peptidomimetics, polymers (e.g., cationic derivatives of polyacrylate, poly (norbornene), poly(arylamide)), and oligomers. Although these synthetic analogues are relatively facile and inexpensive to prepare in large quantity, it still remains challenging to have potent antimicrobial activity while retaining high selectivity towards microbes (i.e., minimum toxicity towards mammalian cells).

The facially amphiphilic conformations of the AMPs are believed to be an important factor in their selective toxicity to bacterial cells over mammalian cells. Therefore, as described herein, cationic amphiphiles (CAms) with a similar spatial arrangement were generated. Two series of bis-cationic compounds, ether- and ester-linked CAms, were synthesized with a tartaric acid sugar backbone and flexible spacers between the cationic charge moieties and backbone, which allow the hydrophilic ammonium moieties and hydrophobic alkyl arms to be positioned on opposite sides of the backbone. The hydrocarbon arms were conjugated to backbone via ether or ester linkages, exploring the impact of side chain orientation on their physicochemical and biological properties, which has not been fully established. It was hypothesized that the variation of linkage flexibility may affect the conformation of the CAms, leading to alternation in membrane-CAm interactions. While increasing hydrophobicity may result in increased antimicrobial potency, it has been reported that hemolytic and cytotoxic activities may also increase. Thus, the hydrophobicity of CAms was also systematically tuned through varying the length of the hydrocarbon arms to achieve potent bacterial membrane-lysing activity while mitigating adverse effects.

The CAms were found to readily self-assemble into different nanostructures in aqueous solutions and their antimicrobial activity was evaluated against a panel of microbes including both Gram-positive and Gram-negative bacteria. Certain compounds displayed broad-spectrum activity and negligible cytotoxicity. Additionally, the membrane-lysing mechanism of the CAms was examined via microscopies and a simulation of the molecular dynamics was performed to further understanding at the molecular level.

Materials and Methods 1.1. Materials

All reagents and solvents were purchased from Sigma-Aldrich (Milwaukee, Wis.) and were used as received unless otherwise mentioned. Di-tert-butyl L-tartrate and di-2-bocaminoethyltartramide were prepared as previously published (D. S. Abdelhamid, Y. Zhang, D. R. Lewis, P. V. Moghe, W. J. Welsh and K. E. Uhrich, *Biomaterials*, 2015, 53, 32-39; A. Faig, T. D. Arthur, P. O. Fitzgerald, M. Chikindas, E. Mintzer and K. E. Uhrich, *Langmuir*, 2015, 31, 11875-11885). Anhydrous dimethylformamide (DMF) was dried over 4 Å molecular sieve at least overnight prior use. 1 N hydrochloric acid (HCl) was purchased from Fisher Scientific (Fair Lawn, N.J.). N-Boc-ethylenediamine was purchased from Alfa Aesar (Ward Hill, Mass.). 1-(3-dimethylaminopropyl)-2-ethylcarbodiimide hydrochloride (ED-C.HCl) was purchased from AK Scientific (Union City, Calif.). Silicon wafers were purchased from Ted Pella, Inc (Redding, Calif.). For antimicrobial assays, Gram-positive *Staphylococcus aureus* ATCC 13565, *Listeria monocytogenes* Scott A, Gram-negative *Escherichia coli* O157:H7, *Salmonella enterica* serovar *typhimurium*, *Pseudomonas aeruginosa* ATCC 15442, and were received from the American Tissue Culture Collection (ATCC, Manassass, Va., USA). For cell experiments, reagents include human buffy coats purchased from the Blood Center of New Jersey (East Orange, N.J.) and New York Blood Center (Long Island City, N.Y.), penicillin/streptomycin were purchased from Lonza (Basel, Switzerland), Dulbecco's modified eagle medium (DMEM) and Vybrant® MTT ((3-(4,5-dimethylthiazol-2-yl)-2,5-diphenyltetrazolium bromide) cell proliferation assay kit were purchased from ThermoFisher Scientific (Waltham, Mass.).

1.2. Characterization

Proton ($^1$H) and carbon ($^{13}$C) nuclear magnetic resonance (NMR) were recorded on a Varian 400 or 500 MHz spectrophotometer. Samples (~2-10 mg/mL) were dissolved in deuterated chloroform (CDCl$_3$) or CD$_3$OD with trimethylsilane (TMS) or deuterated solvent (CD$_3$OD) as an internal reference. Fourier transform infrared (FT-IR) spectra were acquired using a Thermo Scientific Nicolet iS10 spectrophotometer by solvent-casting onto sodium chloride (NaCl) plates; each spectrum was an average of 32 scans. Molecular weights were determined by a ThermoQuest Finnigan LCQ-DUO system (Thermo Scientific, Waltham, Mass.) equipped with an electrospray ionization (ESI) source, mass spectrometer (MS) detector, a syringe pump and the Xcalibur data system. Samples were dissolved in spectrophotometric grade methanol (MeOH) at a concentration of 10 μg/mL.

1.3. Synthesis of Ether-Linked Cationic Amphiphiles 1.3.1. Synthesis of Alkylated Di-Tert-Butyl L-Tartrate (2).

The alkylation of di-tert-butyl L-tartrate with 1-bromooctane to prepare 2a is presented as an example. Following a modified literature procedure, di-tert-butyl L-tartrate (600 mg, 2.29 mmol) was dissolved in 20 mL anhydrous DMF under argon and the solution was then cooled to 0° C. using an ice bath. Sodium hydride (NaH, 192 mg, 4.80 mmol) was added and the reaction stirred for 20 min. 1-Bromododecane (0.88 mL, 5.03 mmol) was added dropwise and the reaction mixture was allowed to stir overnight and warm to room temperature. The reaction was quenched with 20 mL saturated ammonium chloride ($NH_4Cl$) solution and extracted with ethyl acetate (3×20 mL). Organic layers were combined, washed with brine (1×60 mL), and dried over magnesium sulfate ($MgSO_4$) before solvent was removed in vacuo. 2a was purified on silica gel via column chromatography using a hexane:ethyl acetate gradient (100:0 to 98:2).

2a. Yield: 353 mg, 48% (colorless oil). $^1$H-NMR (500 MHz, $CDCl_3$): 4.16 (s, 2H), 3.72 (m, 2H), 3.30 (m, 2H), 1.57 (m, 4H), 1.49 (s, 18H), 1.25 (br, 20H), 0.86 (t, 6H). $^{13}$C-NMR (500 MHz, $CDCl_3$): 169.17, 81.92, 80.67, 72.68, 32.04, 29.68, 29.43, 28.36, 26.24, 22.86, 14.29. IR ($cm^{-1}$, thin film from $CHCl_3$): 1748 (C=O, ester), 1109 (C—O). ESI-MS m/z: 509.2 $[M+Na]^+$.

2b. Yield: 435 mg, 60% (colorless oil). $^1$H-NMR (500 MHz, $CDCl_3$): δ 4.15 (s, 2H), 3.72 (m, 2H), 3.29 (m, 2H), 1.57 (m, 4H), 1.49 (t, 18H), 1.24 (br, 28H), 0.87 (t, 6H). $^{13}$C-NMR (400 MHz, $CDCl_3$): δ 169.12, 81.87, 80.65, 72.65, 32.09, 29.85, 29.76, 29.71, 29.51, 28.33, 26.23, 22.87, 14.29. IR ($cm^{-1}$, thin film from $CHCl_3$): 1755 (C=O, ester), 1116 (C—O). ESI-MS m/z: 565.3 $[M+Na]^+$.

2c. Yield: 275 mg, 60% (colorless oil). $^1$H-NMR (400 MHz, $CDCl_3$): δ 4.16 (s, 2H), 3.72 (m, 2H), 3.30 (m, 2H), 1.60 (br, 4H), 1.49 (s, 18H), 1.24 (b, 36H), 0.88 (t, 6H). $^{13}$C-NMR (500 MHz, $CDCl_3$): δ 169.18, 81.93, 80.69, 72.68, 32.15, 29.87, 29.57, 28.37, 26.25, 22.91, 14.34. IR ($cm^{-1}$, thin film from $CHCl_3$): 1751 (C=O, ester), 1112 (C—O). ESI-MS m/z: 621.4 $[M+Na]^+$.

1.3.2. Synthesis of Alkylated L-Tartaric Acid (3).

The deprotection of 2 to afford 3 is presented using 3a as an example. Following a modified literature procedure, 2a (397 mg, 0.82 mmol) was dissolved in 13 mL anhydrous dichloromethane (DCM) under argon and the solution was cooled to 0° C. using an ice bath. Trifluoroacetic acid (TFA, 2.5 mL, 32.64 mmol) was added dropwise via a syringe and the reaction mixture was allowed to stir overnight and warm to room temperature. The crude mixture was concentrated in vacuo to remove solvent and TFA and then precipitated in chilled hexane. The pure product was isolated via vacuum filtration.

3a. Yield: 296 mg, 97% (white solid). $^1$H-NMR (400 MHz, CDCl3): 4.39 (s, 2H), 3.73 (m, 2H), 3.49 (m, 2H), 1.60 (m, 4H), 1.26 (br, 20H), 0.88 (t, 6H). $^{13}$C-NMR (500 MHz, $CDCl_3$): 173.13, 79.65, 73.68, 32.00, 29.50, 29.47, 29.39, 25.94, 22.84, 14.28. IR ($cm^{-1}$, thin film from $CHCl_3$): 3350-3600 (COOH), 1731 (C=O), 1100 (C—O). ESI-MS m/z: 373.3 $[M–H]^-$.

3b. Yield: 205 mg, 97% (white solid). $^1$H-NMR (400 MHz, $CDCl_3$): δ 4.38 (s, 2H), 3.71 (m, 2H), 3.50 (m, 2H), 1.60 (m, 4H), 1.26 (br, 28H), 0.88 (t, 6H). $^{13}$C-NMR (400 MHz, $CDCl_3$): δ 172.09, 79.63, 73.81, 32.11, 29.77, 29.74, 29.56, 29.53, 25.96, 22.90, 14.33. IR ($cm^{-1}$, thin film from $CHCl_3$): 3300-3600 (COOH), 1735 (C=O), 1097 (C—O). ESI-MS m/z: 429.3 $[M–H]^-$.

3c. Yield: 200 mg, 89% (white solid). $^1$H-NMR (400 MHz, $CDCl_3$): 4.38 (s, 2H), 3.69 (m, 2H), 3.53 (m, 2H), 1.60 (m, 4H), 1.25 (br, 36H), 0.88 (t, 6H). $^{13}$C-NMR (500 MHz, $CDCl_3$): 172.49, 79.40, 73.64, 34.20, 31.90, 29.63, 29.61, 29.57, 29.49, 29.35, 29.33, 29.27, 25.72, 22.67, 14.10. IR ($cm^{-1}$, thin film from $CHCl_3$): 3100-3600 (COOH), 1744 (C=O), 1109 (C—O). ESI-MS m/z: 485.7 $[M–1]^-$.

1.3.3. Synthesis of N-Boc Alkylated Tartaric Acid (4).

The conjugation of N-Boc ethylendiamine to 3 was used to prepare 4 is presented using 4a as an example. Following a previously published procedure, 3a (296 mg, 0.79 mmol), EDC-HCl (637 mg, 3.32 mmol), and 4-dimethylaminopyridine (DMAP, 193 mg, 1.58 mmol) were dissolved in 7 mL anhydrous DCM under argon. Upon complete dissolution, N-Boc-ethylenediamine (0.31 mL, 1.98 mmol) was added via syringe and the reaction stirred overnight at room temperature. The reaction mixture was washed with 10% potassium bisulfate ($KHSO_4$, 2×15 mL) and brine (1×15 mL). The crude mixture was then dried over $MgSO_4$, filtered, and concentrated in vacuo. The crude product was then precipitated in chilled hexane and isolated via vacuum filtration.

4a. Yield: 316 mg, 61% (white powder). $^1$H-NMR (400 MHz, $CDCl_3$): δ 7.03 (s, 2H), 4.95 (s, 2H), 4.23 (s, 2H), 3.52 (m, 8H), 3.28 (m, 4H), 1.55 (m, 4H), 1.44 (s, 18H), 1.26 (br, 20H), 0.88 (t, 6H). $^{13}$C-NMR (500 MHz, $CDCl_3$): δ 171.11, 156.35, 81.44, 73.53, 40.73, 39.88, 32.03, 29.91, 29.58. 29.46, 28.60, 26.19, 22.84, 14.30. IR ($cm^{-1}$, thin film from $CHCl_3$): 3373 (NH), 1690 (C=O, carbamide), 1654 (C=O, amide). ESI-MS m/z: 681.2 $[M+Na]^+$.

4b. Yield: 300 mg, 68% (white powder). $^1$H-NMR (400 MHz, $CDCl_3$): δ 7.05 (s, 2H), 4.97 (s, 2H), 4.22 (s, 2H), 3.52 (m, 8H), 3.28 (m, 4H), 1.54 (m, 4H), 1.43 (s, 18H), 1.25 (br, 28H), 0.87 (t, 6H). $^{13}$C-NMR (500 MHz, $CDCl_3$): δ 170.96, 156.45, 81.44, 79.75, 73.53, 40.73, 39.87, 32.11, 29.91, 29.52, 29.66, 29.81, 29.91, 28.61, 26.20, 22.89, 14.33. IR ($cm^{-1}$, thin film from $CHCl_3$): 3349 (NH), 1702 (C=O, carbamide), 1677 (C=O, amide). ESI-MS m/z: 738.1 $[M+Na]^+$.

4c. Yield: 300 mg, 70% (white powder). $^1$H-NMR (400 MHz, $CDCl_3$): δ 7.04 (s, 2H), 4.96 (s, 2H), 4.22 (s, 2H), 3.52 (m, 8H), 3.28 (m, 4H), 1.54 (m, 4H), 1.44 (s, 36H), 1.25 (br, 28H), 0.87 (t, 6H). $^{13}$C-NMR (500 MHz, $CDCl_3$): $^{13}$C-NMR (400 MHz, $CDCl_3$): 170.94, 98.92, 81.46, 77.97, 73.51, 32.12, 29.91, 29.85, 29.63, 29.55, 28.60, 26.20, 22.89, 14.31. IR ($cm^{-1}$, thin film from $CHCl_3$): 3340 (NH), 1693 (C=O, carbamide), 1655 (C=O, amide). ESI-MS m/z: 793.7 $[M+Na]^+$.

1.3.4. Synthesis of Ether-Linked Cationic Amphiphiles (CAm, 5).

The deprotection of 4a to afford 5a is presented as an example. Briefly, 4a (305 mg, 0.463 mmol) was dissolved in 4.7 mL HCl (4M in dioxane, 18.52 mmol) and then cooled to 0° C. under argon using an ice bath. The reaction mixture was allowed to stir overnight and warmed to room temperature before being stopped. The crude product was concentrated in vacuo and re-dissolved in minimal methanol (1 mL), followed by precipitation into 50 mL centrifuge tubes containing chilled diethyl ether (45 mL). 5a was then isolated via centrifugation (Hettich EBA 12, Beverly, Mass.; 3500 rpm, 3×5 min) and decanting the supernatant.

5a. Yield: 255 mg, quantitative yield (off-white solid). $^1$H-NMR (400 MHz, CD$_3$OD): δ 8.40 (br, 2H), 4.03 (s, 2H), 3.64 (m, 4H), 3.47 (m, 4H), 3.10 (m, 4H), 1.62 (m, 4H), 1.31 (br, 20H), 0.90 (t, 6H). $^{13}$C-NMR (400 MHz, CD$_3$OD): δ 172.49, 82.77, 72.34, 36.56, 31.88, 29.56, 29.42, 29.29, 25.96, 22.56, 13.26. IR (cm$^{-1}$, thin film from CHCl$_3$): 3419 (NH), 1644 (C=O, amide). ESI-MS m/z: 460.5 [M+H]$^+$.

5b. Yield: 188 mg, 92% (off-white solid). $^1$H-NMR (400 MHz, CD$_3$OD): 8.40 (br. 2H), 4.01 (s, 2H), 3.64 (m, 4H), 3.45 (m, 4H), 3.10 (t, 4H), 1.62 (m, 4H), 1.30 (s, 28H), 0.90 (t, 6H). $^{13}$C-NMR (400 MHz, CDCl$_3$): 172.47, 82.84, 72.31, 39.93, 36.55, 31.91, 29.65, 29.61, 29.57, 29.47, 29.33, 25.98, 22.57, 13.27. IR (cm$^{-1}$, thin film from CHCl$_3$) 3424 (NH), 1648 (C=O, amide). ESI-MS m/z: 515.4 [M+H]$^+$.

5c. Yield: 220 mg, quantitative yield (off-white solid). $^1$H-NMR (500 MHz, CDCl$_3$): δ 8.42 (br, 2H), 4.00 (s, 2H), 3.66 (m, 4H), 3.46 (m, 4H), (s, 4H), 1.63 (m, 4H), 1.29 (s, 38H), 0.90 (t, 6H). $^{13}$C-NMR (500 MHz, CDCl$_3$): δ 172.47, 82.91, 72.29, 29.65, 29.62, 29.57, 29.49, 29.33, 25.99, 22.56, 13.27. IR (cm$^{-1}$, thin film from CHCl$_3$) 3424 (NH), 1656 (C=O, ester). ESI-MS m/z: 571.9 [M+1]$^+$.

1.4. Synthesis of Ester-Linked Cationic Amphiphiles 1.4.1. Synthesis of Acylated Di-2-Bocaminoethyltartramide (7).

The acylation of di-2-bocaminoethyltartramide to prepare 7 is presented using 7a as an example. Following a published procedure (A. Faig, T. D. Arthur, P. O. Fitzgerald, M. Chikindas, E. Mintzer and K. E. Uhrich, *Langmuir*, 2015, 31, 11875-11885), octanoic acid (146 mg, 1.01 mmol), di-2-bocaminoethyltartramide (200 mg, 0.46 mmol), and DMAP (23 mg, 0.19 mmol) were dissolved in 16 mL anhydrous DCM and 7 mL anhydrous DMF under nitrogen. EDC-HCl (370 mg, 1.93 mmol) was added, and the reaction was stirred overnight at room temperature. The reaction mixture was concentrated in vacuo, and then reconstituted in DCM, washed with aqueous solutions of 10% KHSO$_4$ (3×40 mL), saturated sodium bicarbonate (NaHCO$_3$, 3×40 mL) solution, and brine (1×50 mL). The combined organic layer was dried over MgSO$_4$, concentrated in vacuo, and then triturated in 100 mL hexanes for 4 h and the pure product was isolated via vacuum filtration.

7a. Yield: 280 mg, 89% (white solid). $^1$H-NMR (MHz, CDCl$_3$): δ 6.97 (s, 2H), 5.57 (s, 2H), 5.13 (s, 2H), 3.28 (m, 8H), 2.46 (m, 4H), 1.62 (m, 4H), 1.45 (s, 18H), 1.29 (br, 16H), 0.88 (t, 6H). $^{13}$C-NMR (MHz, CDCl$_3$): δ 172.32, 167.01, 79.96, 72.42, 41.23, 39.94, 34.04, 31.88, 29.25, 28.60, 24.89, 22.81, 14.27. IR (cm$^{-1}$, thin film from CHCl$_3$): 3454 (NH), 1793 (C=O, ester), 1751 (C=O, carbamide), 1694 (C=O, amide). ESI-MS m/z: 709.5 [M+Na]$^+$.

7b. Yield: 290 mg, 85% (white solid). $^1$H-NMR (MHz, CDCl$_3$): δ 7.04 (s, 2H), 5.58 (s, 2H), 5.17 (s, 2H), 3.29 (m, 8H), 2.44 (m, 4H), 1.63 (m, 4H), 1.45 (s, 18H), 1.26 (br, 24H), 0.88 (t, 6H). $^{13}$C-NMR (MHz, CDCl$_3$): δ 172.33, 167.04, 79.96, 72.41, 41.23, 39.95, 34.04, 32.07, 29.66, 29.49, 29.31, 28.61, 24.89, 22.88, 14.31. IR (cm$^{-1}$, thin film from CHCl$_3$): 3454 (NH), 1794 (C=O, ester), 1752 (C=O, carbamide), 1694 (C=O, amide). ESI-MS m/z: 765.5 [M+Na]$^+$.

7c. Yield: 350 mg, 95% (white solid). $^1$H-NMR (MHz, CDCl$_3$): δ 6.96 (s, 2H), 5.56 (s, 2H), 5.12 (s, 2H), 3.28 (m, 8H), 2.43 (m, 4H), 1.63 (m, 4H), 1.45 (s, 18H), 1.26 (br, 32H), 0.89 (t, 6H). $^{13}$C-NMR (MHz, CDCl$_3$): δ 172.32, 167.02, 79.95, 72.44, 39.94, 34.05, 32.12, 29.84, 29.72, 29.54, 29.32, 28.61, 24.90, 22.90, 14.33. IR (cm$^{-1}$, thin film from CHCl$_3$): 3454 (NH), 1794 (C=O, ester), 1752 (C=O, carbamide), 1694 (C=O, amide). ESI-MS m/z: 821.5 [M+Na]$^+$.

1.4.2. Synthesis of Ester-Linked CAM (8).

The deprotection of 7 to afford 8 is presented using 8a as an example. The deprotection was carried out in a similar manner as were the ether-linked CAms, using 7a (275 mg, 0.40 mmol) and HCl (4M in dioxane, 16 mmol, 4 mL). If necessary, additional anhydrous dioxane (0.5-1 mL) was added to improve stirring.

8a. Yield: 210 mg, 94% (off-white solid). $^1$H-NMR (MHz, CD$_3$OD): δ 8.62 (s, 2H), 5.57 (s, 2H), 3.50 (m, 4H), 3.07 (m, 4H), 2.50 (m, 4H), 1.62 (m, 4H), 1.33 (br, 16H), 0.91 (t, 6H). $^{13}$C-NMR (MHz, CD$_3$OD): δ 172.90, 168.96, 72.42, 39.44, 36.93, 33.35, 31.68, 28.93, 28.93, 24.59, 22.50, 13.22. IR (cm$^{-1}$, KBr): 3452 (NH), 1740 (C=O, ester), 1656 (C=O, amide). ESI-MS m/z: 487.4 [M+H]$^+$.

8b. Yield: 230 mg, 93% (white solid). $^1$H-NMR (MHz, CD$_3$OD): δ 8.62 (s, 2H), 5.57 (s, 2H), 3.49 (m, 4H), 3.07 (m, 4H), 2.49 (m, 4H), 1.62 (m, 4H), 1.32 (br, 24H), 0.90 (t, 6H). $^{13}$C-NMR (MHz, CD$_3$OD): δ 172.89, 168.96, 72.43, 39.45, 36.95, 33.37, 31.87, 29.42, 29.28, 29.26, 28.99, 24.60, 22.55, 13.25. IR (cm$^{-1}$, KBr): 3447 (NH), 1744 (C=O, ester), 1666 (C=O, amide). ESI-MS m/z: 543.3 [M+H]$^+$.

3c. Yield: 250 mg, 94% (white solid). $^1$H-NMR (MHz, CD$_3$OD): δ 8.62 (s, 2H), 5.56 (s, 2H), 3.51 (m, 4H), 3.08 (m, 4H), 2.47 (m, 4H), 1.62 (m, 4H), 1.29 (br, 32H), 0.90 (t, 6H). $^{13}$C-NMR (MHz, CD$_3$OD): δ 172.88, 168.95, 72.44, 39.46, 36.93, 33.39, 31.90, 29.60, 29.47, 29.30, 29.00, 24.62, 22.55, 13.25. IR (cm$^{-1}$, KBr): 3448 (NH), 1742 (C=O, ester), 1654 (C=O, amide). ESI-MS m/z: 599.5 [M+H]$^+$.

1.5. Dynamic Light Scattering (DLS) and Zeta Potential Measurements

DLS and zeta potential analyses were performed using a NanoZS90 instrument (Malvern Instruments, Southboro, Mass.). Samples were dissolved in HPLC grade water at 1 mg/mL and filtered using 0.45 m PTFE syringe filters before each measurement. Each sample was run at a 90° scattering angle in triplicate with 30 measurements per run at 25° C. All results were presented as mean±standard deviation around the mean.

1.6. Broth Microdilution Assay

From the frozen stock (−80° C.), bacteria were inoculated into brain-hear infusion (BHI) agar (Becton Dickinson, Franklin Lakes, N.J.) and propagated under aerobic conditions at 37° C. for 24 h. After the incubation, one colony of each bacterial strain was transferred to BHI broth (Becton Dickinson, Franklin Lakes, N.J.) and sub-cultured at least twice into BHI before being used in experiments.

The minimal inhibitory concentration (MIC) of CAms were identified using a broth microdilution assay modified from previous studies. Briefly, the stock solutions of CAMs were first prepared by dissolving in double-distilled water (ddH$_2$O) and then diluted in BHI broth at pre-determined concentrations. Further serial 2-fold dilutions were performed in a 96-well microplate (Becton Dickinson, Franklin Lakes, N.J.) with BHI broth. The inoculum concentration was adjusted to 5×10$^6$ CFU/mL with ultraviolet-visible (UV-vis) spectroscopy at 600 nm. An equal volume (100 μL) of bacterial suspension was added to each microplate well with a final volume of 200 μL. Plates were incubated at 37° C. for 24 h under aerobic conditions. The lowest CAm concentration that yielded no visible growth was recorded as the MIC. Cetyltrimethylammonium bromide (CTAB), a cationic amphiphile, served as a positive control that could mimic the proposed bactericidal mechanism of the newly synthesized tartaric acid-based compounds.

1.7. Scanning Electron Microscopy (SEM)

Bacteria were grown to the mid-exponential growth phase. Silicon wafers were submerged in the bacterial solutions in the presence or absence of CAMs at their respective MICs and incubated for 1 h. 0.25% glucose was added to facilitate attachment. The bacteria on wafers were fixed in 2.5% glutaraldehyde for 1 h at room temperature, washed three times with PBS, and postfixed 1% osmium tetroxide. The samples were then dehydrated in a graded series of ethanol solutions (50%, 70%, 80%, 95%, 100%), dried with graded hexamethyldisilazane (50%, 100%), and left to air dry for two days. After drying, the wafers were mounted on stub and sputter-coated with 20 nm gold prior to inspection under microscope (Zeiss Sigma Field Emission SEM, Carl Zeiss, Ontario, Calif.) at 5 kV.

1.8. Transmission Electron Microscopy (TEM)

Bacteria were grown as described above for SEM sample preparation. In brief, bacteria were incubated in the presence or absence of CAMs at their respective MICs for 1 h. After centrifugation at 500×g for 10 min, the resulting pellet was fixed in 2.5% glutaraldehyde, washed three times with PBS, and postfixed with 1% osmium tetroxide. The samples were then dehydrated with graded ethanol series (50%, 70%, 80%, 95%, 100%) and embedded in epoxy resin (Dr. Spurr's kit, Electron Microscopy Sciences, Hatfield, Pa.). Ultrathin sections of the cells were stained with 1% uranyl acetate. The microscopy was performed with JEOL 1200EX electron microscope (JEOL USA, Inc., Peabody, Mass.) at 80 kV.

1.9. Hemolytic Activity

Human red blood cells (RBCs) were isolated from 7 mL human blood samples by centrifuging at 400×g for 10 min (Allegra 21 centrifugation, Beckman Coulter, Brea, Calif.) to remove the plasma and buffy coat. The remaining packed RBCs were then washed with 15 mL sterile PBS five times until no traces of plasma were seen. The supernatant was removed by pipetting.

CAm stock solutions were prepared by dissolving CAms in ddH$_2$O prior to use; the samples were gently agitated at 37° C. for 5 min until completely dissolved. To examine the hemolysis properties of CAms, RBCs were suspended with PBS (5% hematocrit). Then 100 µL of the suspended RBCs was mixed with 400 µL freshly prepared CAM stock solutions with final concentrations of 7.8, 15.6, 31.2, 62.5, 125, and 250 µg/mL. Additionally, ddH$_2$O water and PBS (400 µL) were incubated with 100 µL RBC suspension, which served as positive and negative controls, respectively. All the mixtures were shook gently and incubated at 37° C. for 1 h. The mixtures were centrifuged at 400×g (Labenet Spectrafuge 16M microcentrifuge, Labnet International, Inc., Edison, N.J.) for 10 min. The supernatant was then transferred to a cuvette and the absorbance (Abs) was measured at 541 nm using an Infinite M200 PRO plate reader (Tecan Group Ltd., Männedorf, Switzerland). The following formula is used to calculate the percent of hemolysis of RBCs:

$$\text{Hemolysis \%} = \frac{\text{Abs}_{sample} - \text{Abs}_{PBS}}{\text{Abs}_{ddH2O} - \text{Abs}_{PBS}} * 100$$

1.10. Human Foreskin Fibroblast (HFF) Cells Culture and MTT Assay

HFFs were cultured in DMEM supplemented with 10% fetal bovine serum, 1% penicillin/streptomycin and plated at a concentration of 10,000 cells/well in 96-well plate. Plates were incubated at 37° C. and 5% CO$_2$ for 24 h to allow cell attachment prior to use.

CAMs were tested for cytotoxicity against HFFs using a tetrazolium-based colorimetric assay (MTT). CAMs were first dissolved in ddH$_2$O and then diluted in cell medium (DMEM supplemented with 1% penicillin/streptomycin) to reach concentrations of 15.6, 3.9, and 0.95 µg/mL. 100 µL cell media containing CAMs were then added to allocated wells in a 96-well plate. Cells treated with only 1% Triton X-100 and cell medium were used as positive and negative controls, respectively. After 24 h incubation, the medium was removed and replaced with fresh medium. 20 µL of MTT reagent (12 mM in PBS) was then added to each well and further incubated for 4 h at 37° C. Formazan crystals were subsequently dissolved in 100 µL acidified SDS solution at 37° C. for 4 h. The Abs was then recorded with an Infinite M200 PRO plate reader (Tecan Group Ltd., Männedorf, Switzerland) at 570 nm. The following is used to calculate the percent of cell viability of HFFs:

$$\text{Cell viability \%} = \frac{\text{Abs}_{sample} - \text{Abs}_{Triton\ X-100}}{\text{Abs}_{Triton\ X-100} - \text{Abs}_{Medium}} * 100$$

1.11. Statistical Analysis

The data are expressed as mean±standard deviation

Scheme 1. Synthesis of ether-linked CAm (5) and ester-linked CAm (8).

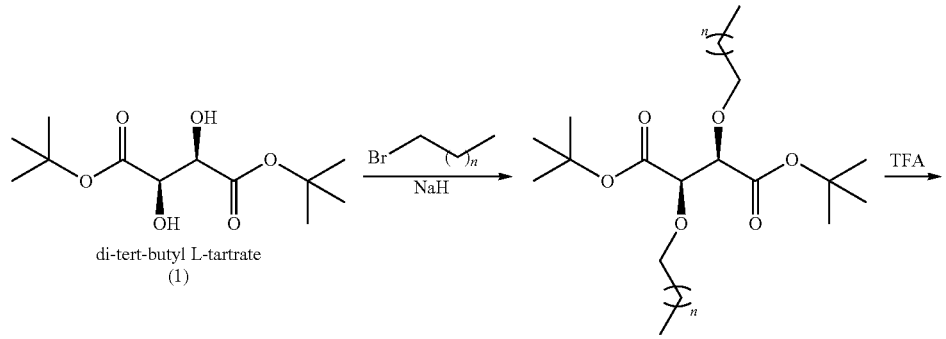

-continued
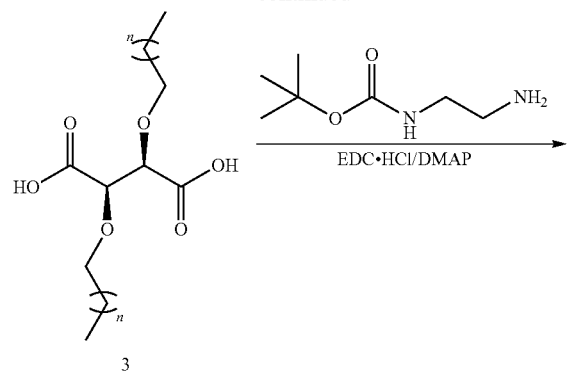
3
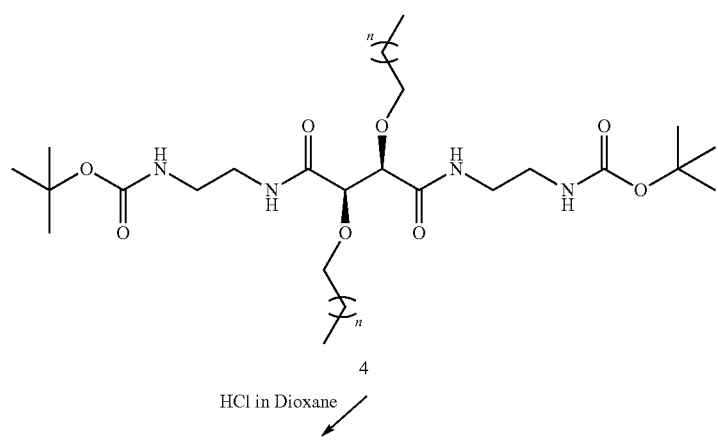
4
HCl in Dioxane
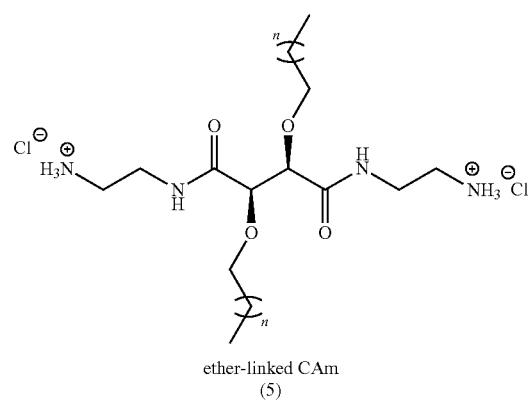
ether-linked CAm
(5)
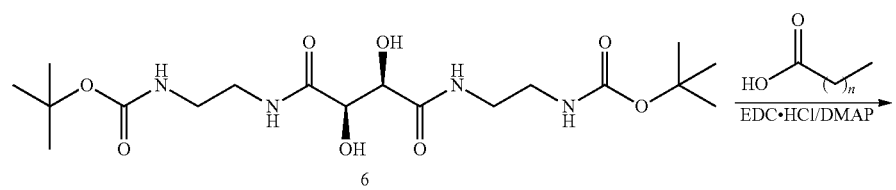
6

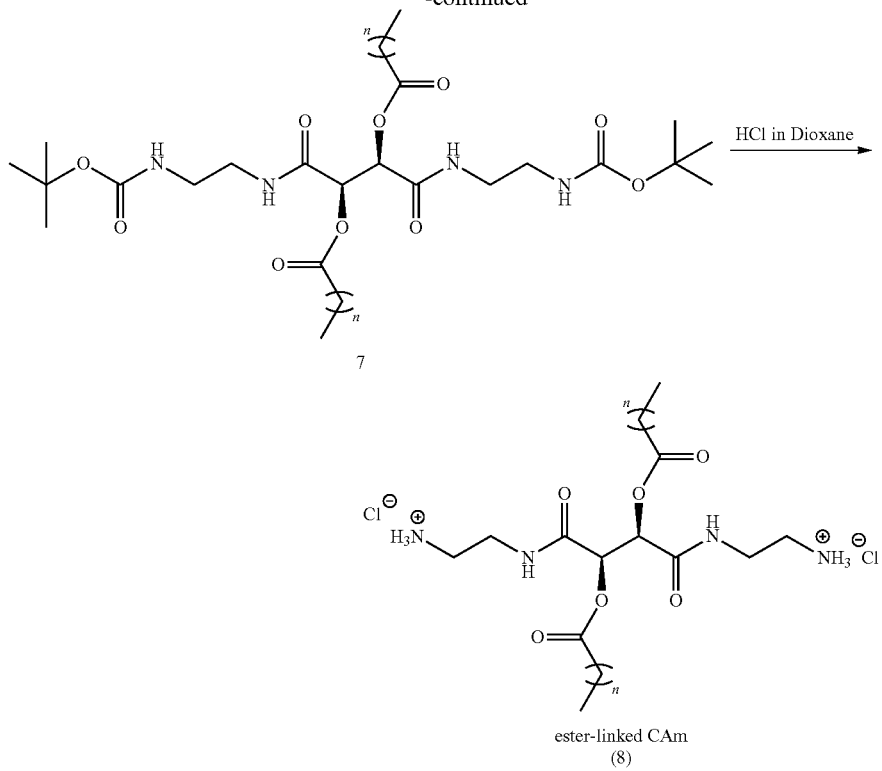

ester-linked CAm
(8)

n = 6 in (5a) and (8a)
n = 8 in (5b) and (8b)
n = 10 in (5c) and (8c)

2. Results and Discussion

2.1. Synthesis and Characterization of CAms

To explore the impact of molecular conformation and hydrophobicity, two series of CAms with ester and ether linkages were designed and synthesized with varying hydrophobicity (Scheme 1).

Briefly, the ether-linked CAms were first synthesized by alkylating di-tert-butyl L-tartrate (1) with bromoalkane through a nucleophilic substation reaction and TFA was subsequently used to deprotect the tert-butyl groups. N-Boc-ethylenediamine was then incorporated to the resulting diacid (3) via carbodiimide coupling to generate CAm precursors (4). Following successful conjugation, 4 was deprotected using HCl in dioxane to afford the final product (5) as chloride salts. The successful synthesis of all intermediates and CAms was confirmed by NMR, FT-IR spectroscopies, and mass spectrometry.

Similarly, a series of CAms with ester linkages between the hydrophobic arms and tartaric acid backbone were synthesized with analogous molecular weights, cationic net charge, and hydrophobicity (i.e., carbon numbers). Instead of alkylation, carbodiimide coupling was carried out with di-2-bocaminoethyltartramide and alkanoic acid followed by acid-catalyzed deprotection to afford 8. The chemical structures of all amphiphiles and intermediates were confirmed as above.

2.2. Antimicrobial Activity

CAms were evaluated against five selected pathogenic microorganisms, including Gram-positive bacteria (i.e., *S. aureus* and *L. monocytogenes*) and Gram-negative bacteria (i.e., *E. coli*, *S. typhimurium*, and *P. aeruginosa*), using a turbidity-based microdilution method. MICs were taken as the lowest concentrations that inhibited the visible bacterial growth. As shown in Table 1, CAms showed antimicrobial activity against a panel of Gram-positive and Gram-negative bacteria, similar to the broad-spectrum properties of AMPs. In addition, the CAms were found to be more active against Gram-positive bacteria than Gram-negative bacteria, with MICs 2-4 fold lower. The higher MIC values for the Gram-negative bacteria could be attributed to the presence of an additional lipopolysaccharide layer, which forms a hydrophilic barrier that could prevent penetration of the highly hydrophobic CAms.

In comparing the antibacterial activity of the amphiphiles, it became apparent that hydrophobicity, which was investigated by varying alkyl chain length, significantly modulated their potency. Interestingly, compared to 5c and 8c with the most hydrophobic domains, which didn't show appreciable antimicrobial activity at even the highest concentration (250 µg/mL) tested, CAms with shorter alkyl length demonstrated remarkably enhanced antimicrobial efficiency. Intriguingly, 5b and 8b with intermediate tail length demonstrated superior antimicrobial activity with MICs as low as 0.95 and 3.9 µg/mL for Gram-positive and Gram-negative bacteria respectively, which is among the lowest MIC reported in literature. Given that a sufficient degree of hydrophobicity in the tails is usually required to promote intercalation and disruption of the bacterial membranes, the result indicated that a "sweet spot" in hydrophobicity was attained and conferred optimal bioactivity. It is worth noting that the MICs of all CAms besides 5c and 8c are below their respective CMCs, suggesting that it is the monomeric CAms rather than the corresponding self-assembly structure that posses the activity. It is plausible that the stable nanostructures formed by 5c or 8c largely limit the interaction between the individual molecules and bacteria, which dramatically diminish their affinity to bacterial membranes. It has also been reported that increased supramolecular order compromised the antimicrobial activity of multidomain peptides.

Notably, CAms with ether linkages (5) exhibited greater antimicrobial efficacy than ester-linked counterparts (8). The discrepancy in antimicrobial activity between the two series may stem from the presence of the carbonyl functionality in the hydrophobic domains of 8, which limits the rotational flexibility of alkyl tails and thus potentially leads to a more rigid molecular conformation/folding. It is speculated that the flexible conformation increases the propensity of the hydrophobic chains to embed into and disintegrate the hydrophobic regions of the lipid membranes, which was studied further via molecular simulation.

ity. The CAms 5a and 8a with a side-chain length of 8 carbons demonstrated sufficient high $HC_{50}$ (47 and 139 µg/mL) but only with moderate selectivity (i.e., 2-12 fold). Notably, antimicrobial agents 5b and 8b preferentially interacted with bacterial cells and exhibited the highest selectivity, indicating their promise as AMP mimics. 5b showed slightly better performance compared to its ester analog 8b, with S.I. as high as 68 for Gram-positive bacteria and 17 for Gram-negative bacteria, as opposed to 43 and 11, which is highly desirable for practical infection treatment.

To further examine the cytocompatibility of CAms 5b and 8b, cytotoxicity was determined after co-incubation with human fibroblasts cells for a prolonged time (24 h), followed by measurement of cell viability with the MTT assay. The results revealed that 5b and 8b did not produce pronounced

TABLE 1

MIC values and hemolytic concentrations of CAms.

| | MIC (µg/mL) | | | | | | | |
|---|---|---|---|---|---|---|---|---|
| | S. aureus | L. monocytogenes | E. coli | S. typhimurium | P. aeruginosa | $HC_{50}{}^a$ | S.I.$^b$ | |
| CAms | (G+) | (G+) | (G−) | (G−) | (G−) | (µg/mL) | G+ | G− |
| 5a | 3.9 | 3.9 | 15.6 | 7.8 | 3.9 | 47 | 12 | 3 |
| 5b | 0.95 | 0.95 | 3.9 | 3.9 | 3.9 | 65 | 68 | 17 |
| 5c | 3.9 | 125 | >250 | >250 | >250 | >250 | >64 | n.a. |
| 8a | 31.2 | 31.2 | 62.5 | 62.5 | 31.2 | 139 | 4 | 2 |
| 8b | 1.9 | 1.9 | 3.9 | 3.9 | 3.9 | 81 | 43 | 11 |
| 8c | 15.6 | >250 | >250 | >250 | >250 | >250 | >16 | n.a. |

$^a$Concentration required to induce 50% leakage of hemoglobin from hRBCs.
$^b$Selectivity index (S.I.) was determined as $HC_{50}$/MIC using S. aureus and E. coli as representatives for S.I. of G+ and G− calculation respectively.

Taken together, antimicrobials 5b and 8b displayed broad-spectrum and potent antimicrobial activity. Hydrophobicity is necessary but not sufficient to dictate CAm's biological activity as molecular conformation and assembling state also impact their behavior.

2.3. Cell Compatibility

Figure 1B:
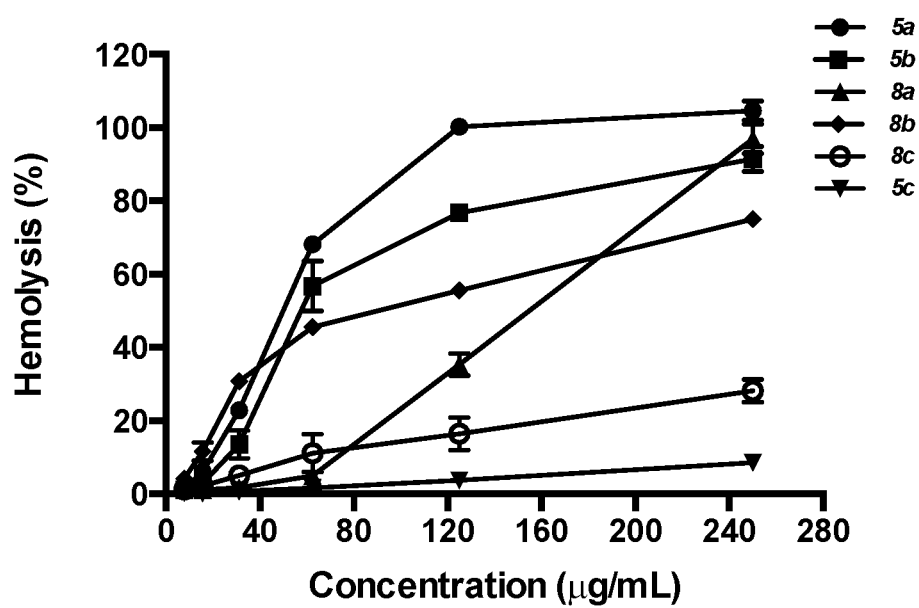

Hemolytic activity is an important factor to be considered for antimicrobial therapy development and often designated as the concentration that leads to 50% lysis of red blood cells. A hemolysis assay was conducted by incubating hRBC with CAms at various concentrations and the leakage of hemoglobin was quantified by UV spectroscopy. In general, all CAms induced negligible hemolysis at their respective MICs (FIG. 1B) even though ether series displayed even higher selectivity (i.e., S.I.) towards bacterial cells over mammalian cells. The difference in membrane composition between bacteria and mammalian cells may account for the specificity and selectivity, which is further confirmed through the molecular simulation. The primary phospholipids in the outer leaflet of mammalian cell membranes were zwitterionic phosphatidylcholine (PC).

Figure 1C:
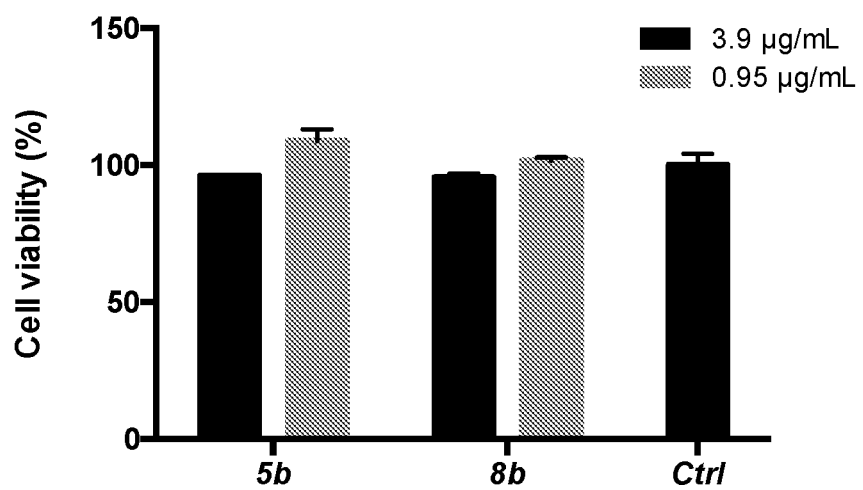
Figure 3A:
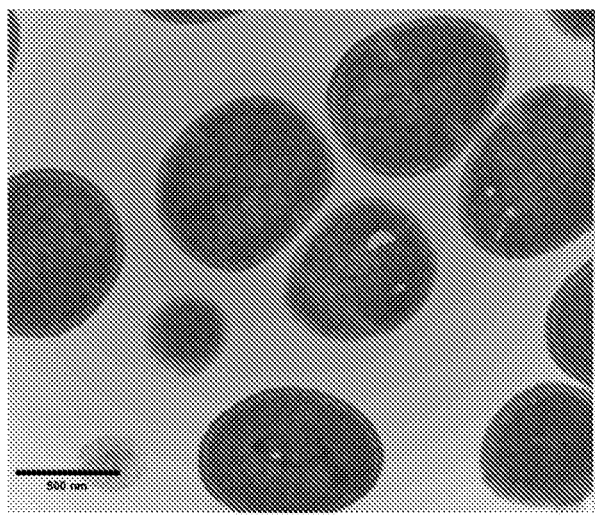
FIGS. 3A-D.
Figure 3B:
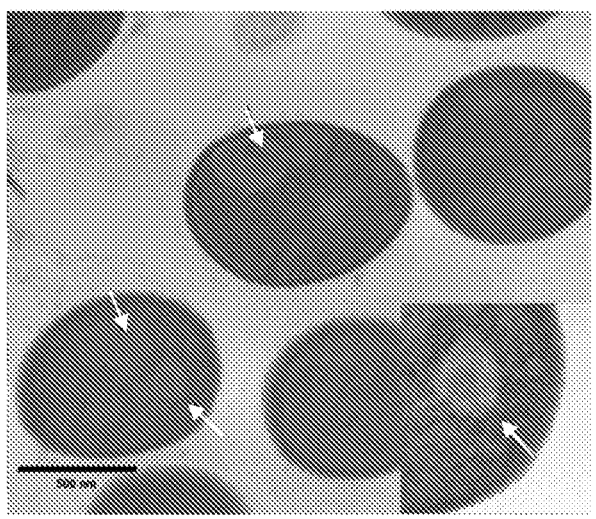
Figure 3C:
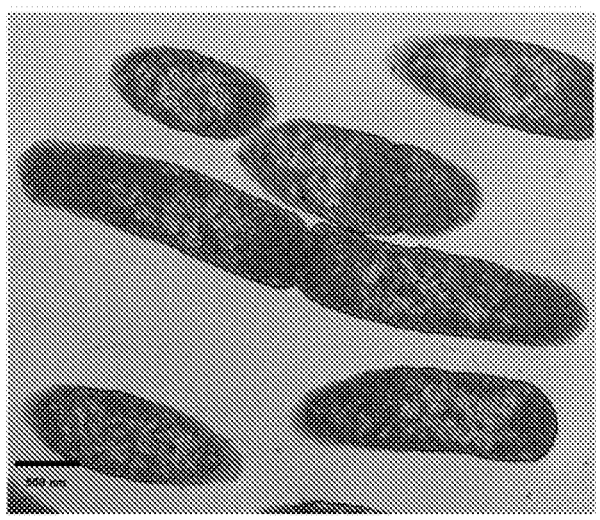
Figure 3D:
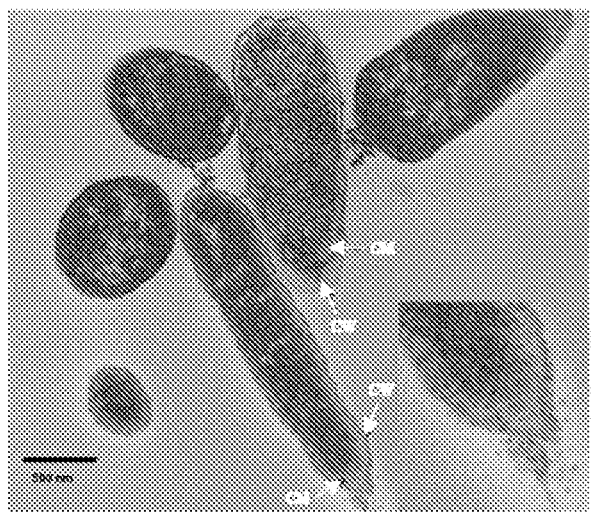

Surprisingly, no linear dependence on hydrophobicity was observed for $HC_{50}$ of the Cams, considering that increased hydrophobicity has been correlated to stronger hemolytic activity. On the contrary, interesting similarities in relation to the measured MICs were observed for the results (Table 1). For example, while 5c and 8c induced the least hemolytic reaction ($HC_{50}$>250 µg/mL), they have also been shown to be weak antimicrobials, implying low membrane activity overall. The trend again suggests that the molecular conformation and self-assembling state play an important role in CAm-membrane interaction in addition to the hydrophobic-cytotoxicity to cells at concentrations sufficiently high to inhibit bacterial growth, indicating their minimum cytotoxicity (FIG. 1C).

Antimicrobial 5b, which exerts the most potent antimicrobial activity while having the highest selectivity, was further studied to validate its mode of action.

2.4. Mechanism of Action

Several models for the interaction of AMPs with the membranes, such as "barrel stave", "toroidal pore", "carpet model", and detergent model were postulated. Nevertheless, the bacterial membrane is severely damaged in the end, which can lead to the death of the cells. The bacterial cell membrane is responsible for many essential functions: transport, osmoregulation and respiration processes, biosynthesis and cross-linking of peptidoglycan, and synthesis of lipids. It is doubtless that for all these functions, membrane integrity is necessary, and its disturbance can directly or indirectly cause metabolic dysfunction and cell death, besides pore formation. To verify the proposed membrane-targeting mechanism of cationic amphiphiles, S. aureus and E. coli were selected for Gram-positive and Gram-negative bacterial strains, respectively; they were treated with antimicrobial 5b at MIC levels. Significant morphological and ultrastructural alternations in comparison to the control (untreated bacterial cells) were observed with SEM and TEM.

Control cells (FIGS. 2 A and C) in SEM images appeared intact with smooth and well-defined surface whereas treated cells showed severe membrane disruption and deformation. Open holes, deep craters, and protruding bubbles (FIG. 2 B) were observed with S. aureus treated with 5b, which likely led to subsequent loss of cytoplasm contents from the bacterial cells. Furthermore, burst cells and cellular debris of *S. aureus* as a result of complete lysis were also seen. Similarly, for treated *E. coli* cells (FIG. 2 D), there were blisters and bumps formed on the surface, indicating the disruption and alternation of cell membranes.

IC50 values of the CAms were also determined using the results from FIG. 2 and are shown below in Table 2.

TABLE 2

S.I. is defined as IC50/MIC (*S. aureus* and *E. coli* are used as representatives for G+ and G− for calculation respectively).

| CAMs | IC$_{50}$ (μg/mL) | S.I. G+ | S.I. G− |
|---|---|---|---|
| 5a | 11 | 2.8 | 0.7 |
| 5b | 5.6 | 5.9 | 1.4 |
| 8a | 55.6 | 1.8 | 0.9 |
| 8b | 13.9 | 7.3 | 1.7 |

TEM was then used to examine the ultrastructural changes in bacteria induced by CAms (FIGS. 3A-D). Prior to treatment, *S. aureus* showed regular round, proliferating cells with intact and smooth surface. In addition, the intracellular DNA region displayed a heterogeneous electron density. However, upon treatment with 5b, the bacteria demonstrated profound internal damage besides cell membranes with increased roughness. Multiple spherical void structures were observed as well as cytoplasm with a more uniform electron density. Initially, *E. coli* displayed normal rod shape and undamaged structure of cell membranes. In contrast, treated *E. coli* experienced extensive ultrastructural damage and showed strong evidence of membrane disruption and rupture. Periplasmic space was expanded and had an irregular course, suggesting increased membrane permeability. The polar regions of the cells were especially susceptible to the CAm treatment and experienced fragmentation; this can be potentially explained by the preferential interaction of the cationic amphiphiles with negatively charged cardiolipin microdomains, which are mostly located at the poles.

From the combined evidence of SEM and TEM, it can be inferred that CAms possess antimicrobial activity with cell membrane disruption being the mode of action. The results provided evidence of membrane disrupting mechanism.

Example 2

Figure 4A:
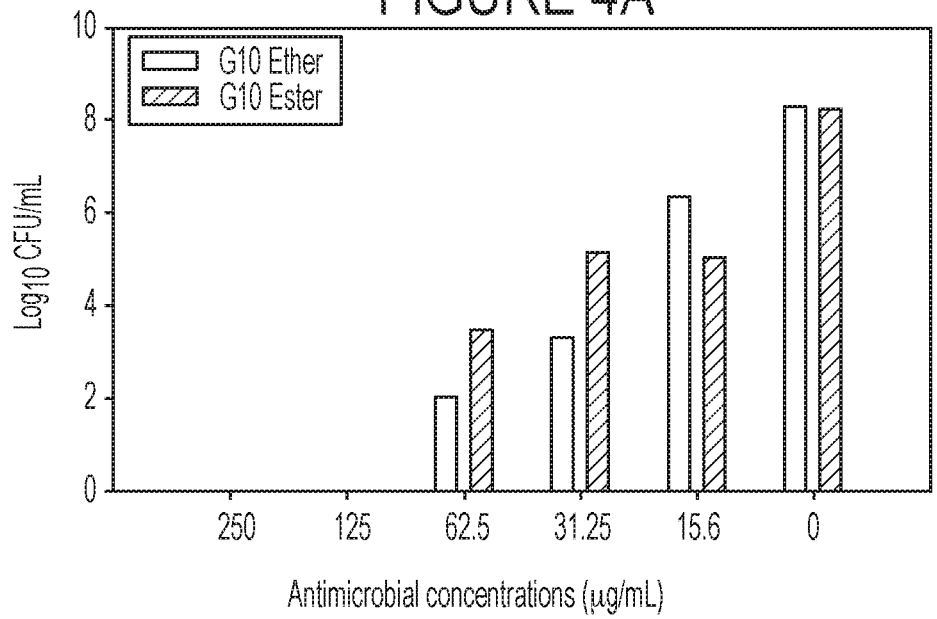
FIGS. 4A-B. G-10 ether (5b) and G-10 ester (8b) inhibition of *G. vaginalis* (FIG. 4A) and *L. monocytogenes* (FIG. 4B) in pre-formed biofilms. The minimal biofilm bactericidal concentration (MBC-B) was defined as the minimum concentration of antibacterial agent that causes ≥3 log reduction in viable cell numbers compared to the positive control.
Figure 4B:
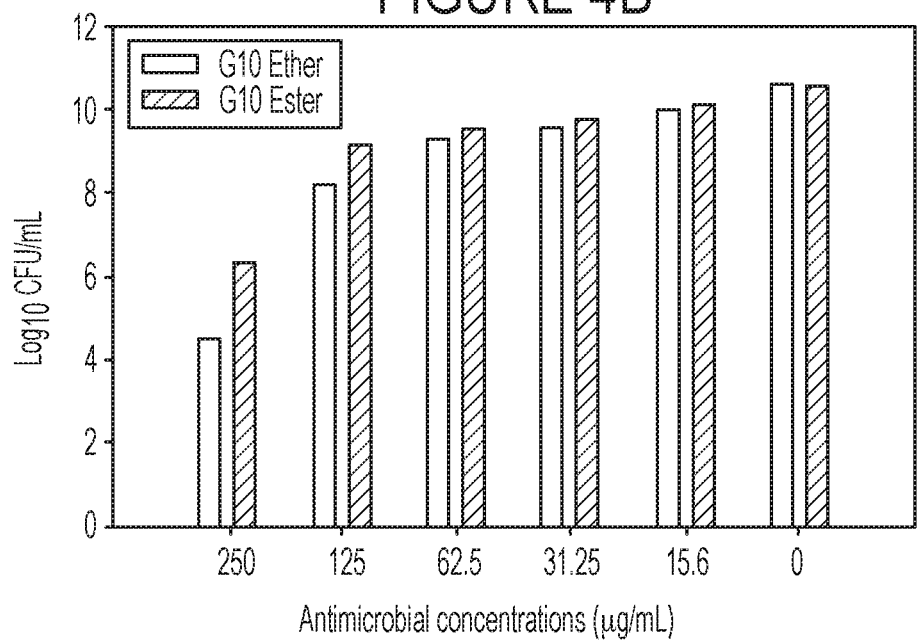
Figure 5:
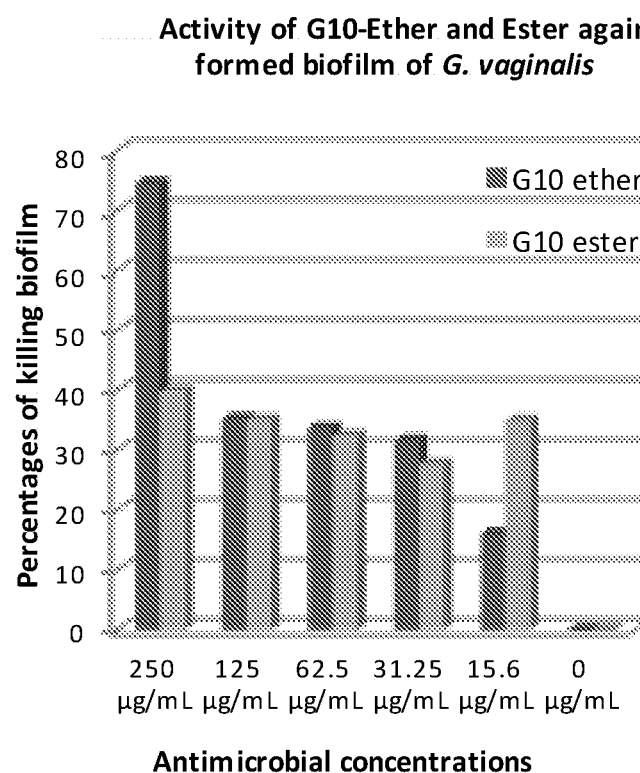
FIG. 5. Biofilm removal (%) of *G. vaginalis* for G-10 ether (5b) and G-10 ester (8b).

As shown in the experiments discussed in Example 1, as well as in the experiments described below, the compounds of the invention are efficacious towards both platonic cells and biofilms, including compound 5b. Specifically, compounds 5b and 8b were tested for their ability to inhibit *G. vaginalis* (FIG. 4A) and *L. monocytogenes* (FIG. 4B) in pre-formed biofilms (see, FIG. 1A and Example 1 for synthesis of 5b and 8b). The minimal biofilm bactericidal concentration (MBC-B), defined as the minimum concentration of antibacterial agent that causes ≥3 log reduction in viable cell numbers compared to the positive control, was established for each compound. The MBC-B values of both 5b and 8b were approximately 31.25 μg/mL for *G. vaginalis* and approximately 250 μg/mL for *L. monocytogenes*, respectively. In contrast, the MBC-B of metronidazole and clindamycin (the commonly prescribed antibiotics) were 500 g/mL and 20000 μg/mL, respectively, for biofilm-associated *G. vaginalis*. Additionally, the G-10 ether (5b) was more efficient in removal up to 70% of biofilm structures of the tested pathogen *G. vaginalis* when used at 250 μg/mL concentration against pre-formed biofilms (FIG. 5).

Methods

The minimum biofilm bactericidal concentrations (MBC-Bs) of the cationic amphiphiles against pre-formed biofilms of *L. monocytogenes* and *G. vaginalis* were identified. The biofilms of the two targeted microorganisms were grown in 96-well plates according to established methodology for Gram-positive and Gram-variable bacteria (Tabak et al., FEMS microbiology letters. 2009; 301(1):69-76). To identify the reduction in the number of biofilm-associated viable cells treated with different concentrations of cationic amphiphiles, the spot plate method was used (Turovskiy et al., Infectious diseases in obstetrics and gynecology. 2012; 2012:284762, 9 pages). In brief, biofilms were washed, disrupted, diluted $10^1$-$10^8$ times with fresh medium and the samples plated on suitable solid medium. Bacterial cells were counted and MBC-B determined as the minimum concentration of compound which produces ≥3 $\log_{10}$ reduction in the number of viable cells (Turovskiy et al., Infectious diseases in obstetrics and gynecology. 2012; 2012: 284762, 9 pages).

Example 3

Ether and Ester Cationic Amphiphiles Control Biofilm Formation by Bacterial Vaginosis Pathogens Abstract Bacterial resistance and recurrence of bacterial vaginosis (BV), a polymicrobial infection, justify the need for novel antimicrobials to counteract microbial resistance to conventional antibiotics. As described herein, two series of cationic amphiphiles (CAms), which are classified as supramolecular nanostructures with membrane-lytic properties, were designed with hydrophilic head groups and non-polar domains. The combination of CAms with commonly prescribed antibiotics is suggested as a promising strategy for targeting microorganisms that are resistant to conventional antibiotics. Activity of the CAms against *Gardnerella vaginalis*, a BV representative pathogen, ranged from 1.1-24.4 μM. Interestingly, the tested healthy *Lactobacillus* species, especially *L. plantarum*, were significantly more tolerant to CAms compared to the selected pathogens. In addition, CAms prevented biofilm formation at concentrations which did not influence the normal growth ability of *G. vaginalis*. Furthermore, the minimum biofilm bactericidal activity (MBC-Bs) of CAms against *G. vaginalis* ranged between 58.8-425.6 μM while much higher concentrations (≥850 μM) were required to produce ≥3 log reduction in the number of biofilm-associated lactobacilli. The conventional antibiotic metronidazole strongly synergized with all tested CAms against planktonic cells and biofilms of *G. vaginalis*. The synergism between CAms and the tested conventional antibiotic may be considered a new, effective, and beneficial method of controlling biofilm-associated BV infection.

Introduction

Bacterial vaginosis (BV) is a non-inflammatory, polymicrobial infection in women of reproductive age (Forsum et al., 2005. Acta Pathol Micro Im Sci 113:81-90). Generally, the infection occurs due to a decrease in protective lactobacilli species, leading to the overgrowth of pathogenic, anaerobic bacteria which are naturally present in low concentrations within the vaginal lumen (Machado et al., 2016. Front Microbiol 6:1528). The mechanism by which the loss of lactobacilli occurs is not yet clear (Spiegel, C. A. 1991. Clin Microbiol Rev 4:485-502), however the decrease in the commensal lactobacilli population causes an increase in pH due to the reduction of lactic acid production and an increase in fatty acid production by anaerobic bacteria, making the vaginal environment more suitable for opportunistic pathogen growth and unfavorable for lactobacilli growth (Kumar et al., 2011. J Pharm Bioallied Sci 3: 496-503). BV affects between 10%-30% of women in developed nations (Allsworth J E, Peipert J F. 2007. Obstet Gynecol 109:114-20), making it three to four times more common than urinary tract infections and three times more prominent than *Trichomonas vaginalis* infection (Goldenberg et al., 1997. Clin Perinatol 24:23-41). While often asymptomatic, BV can lead to serious complications including, but not limited to, abortion or premature birth in pregnant women, pelvic inflammatory disease, endometriosis, and infertility (Machado et al., 2016. Front Microbiol 6:1528). During early pregnancy, the cost of screening for and treating women for BV is quite high; total costs can amount to over $490,000 (Muller et al., 1999. J Reprod Med 44:807-814), not including recurrences. This calls for a safe, effective, and economically conscious treatment of the disease. Although no single bacteria can be considered as the sole causative agent of BV, *Gardnerella vaginalis*, an opportunistic anaerobic pathogen, is the predominant bacterial species isolated from BV infections; *G. vaginalis* forms a thick biofilm and produces toxins as effective virulence factors, increasing bacterial resistance to conventional antibiotics (Machado A, Cerca N. 2015. J Infect Dis 212:1856-1861). The bacterium has been detected in over 98% of BV cases and often exhibits a symbiotic relationship with other anaerobes (Aroutcheva et al., 2001. Clin Infect Dis 33:1022-1027).

Current treatment of bacterial vaginosis includes conventional antibiotics, most often 400-600 mg of metronidazole taken orally (Centers for Disease Control and Prevention (CDC). 2015. *Sexually Transmitted Diseases Treatment Guidelines*, Center for Surveillance, Epidemiology, and Laboratory Services, U.S. Department of Health and Human Services. Atlanta, Ga.). Metronidazole is readily taken up by anaerobic bacteria through passive diffusion where it is activated within the cytoplasm and then reduced to its active form by electron transport, causing inhibition of DNA synthesis (Lofmark et al., 2010. Clin Infect Dis 50:S16-S23). Despite its initial effectiveness against the unwanted bacteria, the antibiotic tends to damage the protective vaginal lactobacilli and fails to fully eradicate the pathogenic biofilm (Machado et al., 2016. Front Microbiol 6:1528). Pathogenic polymicrobial biofilms are especially difficult to eradicate; such biofilms occur in infections like BV while carrying *G. vaginalis* as a predominant BV-associated pathogen (Hardy et al., 2015. PloS One 10: e0136658).

Antibiotic resistance is an impending issue concerning the overuse of antibiotics; *Gardnerella* strains are becoming increasingly resistant to metronidazole (Nagaraja P. 2008. Indian J Med Microbiol 26:155-7). This leads to ineffective treatment of the infection and often a recurring infection: approximately 80% of treated women will have another episode of BV within one year of treatment (Eschenbach D A. 2007. Clin Infect Dis 44:220-221, Filho et al., 2010. HU Revista. 36: 223-230). Therefore, resistance to antibiotics calls for alternative treatments, which leads to an interest in antimicrobial peptides. Antimicrobial peptides (AMPs) are proteinaceous substances with low molecular weights and broad spectrum antimicrobial activity against bacteria, fungi, and viruses (Izadpanah A, Gallo R L. 2005. J Am Acad Dermatol 52:381-390). AMP mimicking cationic amphiphilic (CAms) compounds (either bola-like or gemini-like) effectively target the lipopolysaccharide (LPS) layer of the cell membrane of Gram-negative microorganisms; at the same time, eukaryotic cells have a high cholesterol level and low anionic charge, making them out of the target range of most AMPs (Bahar A, Ren D. 2013. Pharmaceuticals 6:1543-1575). AMPs form pores in the cell membrane or disable the proton motive force, as discussed by Wimley and Hristova (Wimley W C, Hristova K. 2011. J Membrane Biol 239:27-34). By targeting the LPS layer of the cell membrane, the cationic AMPs interact with the negatively charged membranes of the bacteria and biofilm surfaces via electrostatic bonding, killing both active and dormant or slowing growth cells; the hydrophobic domain also interacts with and disrupts the hydrophobic membrane resulting in cell death (Laverty et al., 2011. Int J Mol Sci 12:6566-6596).

As described herein, two series of cationic amphiphiles (CAms), which are classified as supramolecular nanostructures with membrane-lytic properties, were designed with hydrophilic head and non-polar domains as AMP mimics. In this study, the antimicrobial and anti-biofilm activity of CAms G8 and G10 ether and ester (Zhang et al., 2017. Nanomedicine: NBM 13:343-352) will be determined against *G. vaginalis* and *Lactobacillus* species by establishing the minimum inhibitory concentration (MIC), minimum biofilm inhibitory concentration (MIC-B) and minimum biofilm bactericidal concentration (MBC-B) of each antimicrobial. The nature of antimicrobial interactions between the CAms and metronidazole against planktonic and biofilm cells will be investigated as well.

Materials and Methods

Synthesis of Gn Formulations

Figure 6:
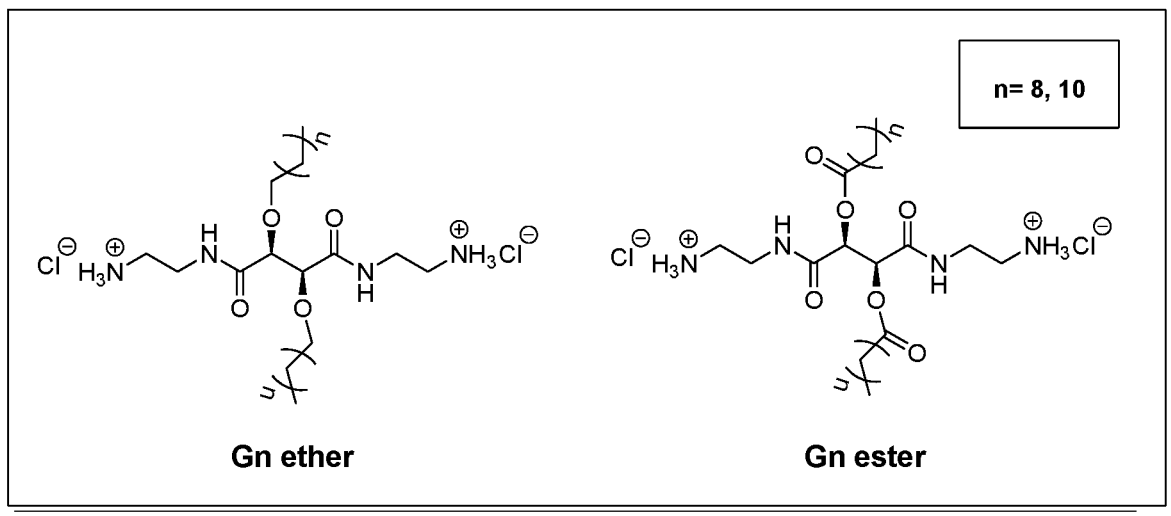
FIG. 6. Structures of the tested CAms showing differences in liker type (ether/ester) and length (n=8,10).

Ether-linked and ester-linked cationic gemini amphiphiles (Gn, where G stands for gemini while n denotes the total carbon number of each hydrophobic arm) with various hydrophobic chain lengths (FIG. 6) were synthesized in high yields following procedures described by Zhang et al. (Zhang et al., 2017. Nanomedicine: NBM 13:343-352; see also, Example 1).

Bacterial Strains and Growth Conditions

*G. vaginalis* ATCC 14019 strain was grown overnight in Brain Heart Infusion broth (Difco, Sparks, Md.) supplemented with 3% horse serum (sBHI) (JRH Biosciences, KS), while BHI supplemented with 1% glucose (BHIG) was used for biofilm formation assays. Each experiment using *G. vaginalis* was performed anaerobically (10% hydrogen, 5% carbon dioxide, and 85% nitrogen) within anaerobic glove boxes (Coy Laboratory Products, Inc., Grass Lake, Mich., USA). Three species of vaginal *Lactobacillus* were used in this study to evaluate the possible harmful effects of CAms on beneficial bacteria: *Lactobacillus plantarum* ATCC 39268, *Lactobacillus rhamnosus* 160 (provided by Dr. Aroutcheva, Rush University Medical Center) and *Lactobacillus gasseri* ATCC 33323; all were grown for 18-24 h in DeMan, Rogosa and Sharpe broth (MRS Difco B D, Franklin Lakes, N.J., USA) under aerobic conditions at 37° C. For lactobacilli biofilm formation, MRS broth supplemented with 1% glucose and 2% sucrose (Fisher Scientific, Waltham, Mass., USA) was utilized.

The antimicrobial activity of CAms was also tested against *Peptostreptococcus anaerobius* ATCC 27337, *Mobiluncus curtisii* ATCC 35241 and *Prevotella bivia* ATCC 29303, all of which, in addition to *G. vaginalis*, are the most commonly isolated anaerobes from BV-infected women. These anaerobes were maintained within the anaerobic chamber and transferred daily into fresh sBHI.

Stock Solution Preparation of CAms Compounds

To prepare a stock solution, the CAm compounds were dissolved in ddH$_2$O and incubated at 37° C. with shaking at 250 rpm for 10 min. Then, the solution was serially diluted twofold with sBHI broth to determine the MIC and with BHIG broth to identify the MIC-B/MBC-B against planktonic and biofilm cells, respectively.

Minimum Inhibitory Concentrations (MIC) of CAms

According to Clinical and Laboratory Standards Institute (CLSI 2010), the MIC is defined as the lowest concentration of antimicrobial compound producing no visible growth or complete inhibition of bacterial growth during 24 h. To determine MIC values, the broth microdilution assay was performed according to Algburi et al. (Algburi et al., 2015. Path Dis 73(5)) with minor modifications. Briefly, the overnight-grown cells were diluted with their suitable culture medium to approach ~$10^6$ CFU/ml. The number of bacterial cells was identified using spot plate method (Turovskiy et al., 2012. Infect Dis Obstet Gynecol 2012:284762). The CAms were serially diluted twofold with sBHI into a non-tissue culture 96-well microplate plate (Falcon, Corning Incorporated, Corning, N.Y., USA) resulting in a final volume of 100 µl for each well. Aliquots of 100 µl of the diluted cell suspension (~$10^6$ CFU/ml) were added to each well of a microplate that was treated with different concentrations of CAms. To avoid culture medium evaporation, 75 µl of mineral oil (Sigma-Aldrich, St. Louis, Mo.) was added to each treated well. The microplate was then transferred to the plate reader (Model 550, Bio-Rad Laboratories, Hercules, Calif., USA) and incubated at 37° C. for 24-36 h. The kinetic reading was statistically analyzed, and the MIC and sub-MIC of each CAm compound were determined.

Minimum Biofilm Inhibition Concentration (MIC-B)

The MIC-$B_{50}$ of an antimicrobial is defined as the lowest concentration of the antimicrobial that inhibits 50% of treated biofilm compared to the untreated one (control), while MIC-$B_{90}$ was defined as the minimum biofilm inhibitory concentration that inhibits 90% (Sandoe et al., 2006. J Antimicrob Chemother 57:767-770). G. vaginalis cells were grown overnight in sBHI broth anaerobically at 37° C. The overnight culture was diluted in BHIG broth 1:100 (v:v) to achieve ~$10^6$ CFU/ml for the biofilm inhibition assay. The CAms were diluted twofold with BHIG into a 96-well tissue culture microplate (Falcon, Corning Incorporated, Corning, N.Y., USA) with a final volume of 100 µl in each well. Aliquots of 100 µl of diluted cell suspensions at $10^6$ CFU/ml were added separately to different concentrations of CAms in a 96-well tissue culture microplate. The microplate was incubated for 48 h at 37° C. under anaerobic conditions. After incubation, the number of non-adherent bacterial cells was counted using a spot plate method and compared with the number of cells of the non-treated control. Then, the intact biofilm was stained with 0.1% crystal violet.

Biofilm Staining Using Crystal Violet (CV)

This method was performed as described by Borucki et al. with minor modifications (Borucki et al., 2003. Appl Environ Microbiol 69:7336-7342). Briefly, after counting the non-adherent cells, the biofilm was fixed at 60° C. for 60 min. in an inverted position using an incubator (New Brunswick Scientific Co., Inc., NJ, USA). In each well, 125 µl of 0.1% crystal violet was added and left at room temperature for 20 min. Each well was then rinsed three to four times with 200 µl of dd$H_2O$ and left for 15 min. to dry at room temperature. To solubilize the biofilm-stained CV, 200 µl of 95% ethanol in water was added and the microplate was incubated at 4° C. for 30 min. One hundred microliter samples of solubilized CV were transferred to a new flat-bottomed 96-well microplate. The absorbance of each sample was measured using a plate reader at 595 nm (Model 550, Bio-Rad Laboratories, Hercules, Calif., USA).

Minimum Biofilm Bactericidal Concentration (MBC-B)

Minimum Biofilm Bactericidal Concentration (MBC-B) is defined as the minimum concentration of antibacterial agent that caused ≥3 log reduction in the number of viable cells as compared to the positive control (Aaron et al., 2002. J Clin Microbiol 40:4172-4179). This assay was performed according to Algburi et al. (Algburi et al., 2015. Path Dis 73(5)) with minor modifications: the overnight-grown G. vaginalis was diluted to approximately $10^7$ CFU/ml. For the biofilm formation assay, aliquots of 200 µl were added into a 96-well tissue culture microplate, sealed by amplification tape (Nalge Nunc International, Rochester, N.Y., USA) and incubated for 24-36 h at 37° C. After incubation, the planktonic cells were removed by gently washing the biofilm twice with 200 µl of fresh broth. The biofilm was then treated with 200 µl of a predetermined concentration of the tested compound. The microplate was incubated for 24 h at 37° C. under anaerobic conditions. After incubation, the antimicrobials (supernatant) were discarded and the biofilm was washed twice with fresh BHIG broth. The biofilm was then disrupted by vigorous pipetting, in order to determine the number of biofilm-associated cells using the spot plate method.

Checkerboard Assay for Antimicrobial Combinations

To evaluate the potential effectiveness of the antimicrobial combinations on planktonic and biofilm cells, a checkerboard assay was performed following Algburi et al. (Algburi et al., 2015. Path Dis 73(5)) with minor modifications. For planktonic cells, the overnight grown G. vaginalis was diluted to approximately $10^6$ CFU/ml. Each antimicrobial agent was diluted twofold with sBHI broth into two separate 96-well non-tissue culture microplates. From each dilution of antimicrobial B, 50 µl was added horizontally over 50 µl of antimicrobial A. Then, 100 µl of bacterial suspension ($10^6$ CFU/ml) was separately added to the predetermined concentration of antimicrobial combinations. The MIC of each combination was determined after 24 h of incubation.

For biofilm formation, the overnight culture of G. vaginalis was diluted to approximately $10^7$ CFU/ml and 200 µl was transferred into a 96-well tissue culture microplate and incubated anaerobically at 37° C. for 24-36 h. Following biofilm formation and removal of non-adherent cells by washing the biofilm twice with BHIG, each antimicrobial was diluted twofold separately with BHIG broth into two 96-white deep-well microplates. From each dilution of antimicrobial B, 125 µL was added horizontally over 125 µL of antimicrobial A (see FIG. 1 of Algburi et al., 2015. Path Dis 73(5)). From each combination, 200 µL samples were added to the biofilm in sequence, and the microplate was incubated for 24 h at 37° C. under anaerobic conditions. The spot plate method was utilized for counting the number of CFU/ml and evaluating the bactericidal activity (MBC-B) of each antimicrobial combination against biofilm-associated G. vaginalis. Isobolograms were used to analyze the nature of antimicrobial interaction, which is classified as synergistic, antagonistic or additive activity against the planktonic and biofilm cells.

Checkerboard Assay, Data Analysis

Isobolograms were used to compare the MIC and MBC-B values of each antimicrobial alone with its MIC and MBC-B values in combination with other antimicrobials. The point on the axis (X) refers to MIC or MBC-B values of the first antimicrobial with the coordinates (0, x), and the point on the axis (Y) represents the MIC or MBC-B values of the second antimicrobial with the coordinates (y, 0) when they used alone. The two MIC or MBCs-B values are connected by a dashed line (Turovskiy Y, Chikindas M L. 2011

Probiotics Antimicrob Proteins 3:144-149). The MICs or MBCs-B of each antimicrobial combination are plotted as dots on the graph. Results are expressed according to the locations of these dots from the line that connects MICs or MBCs-B of the first and second antimicrobials. When MICs or MBCs-B values are located under the line, the two combining antimicrobials are synergized, but antagonized against the tested microorganism when these dots of interaction are above. An additive effect is observed when these dots are located on the line.

Scanning Electron Microscopy (SEM)

SEM was used to visualize the anti-biofilm activity of AMP mimics. As in the biofilm formation assay, G. vaginalis cells were diluted to $10^7$ CFU/ml before 2 ml was transferred to each well of a 6-wells tissue culture plate (Falcon, B D, Franklin Lakes, N.J., USA), which was then incubated for 24 h at 37° C. with a glass slide in each well (12 mm, Fisher Scientific, Waltham, Mass.). After incubation, the biofilms that formed on the glass slides were washed twice with fresh BHIG to remove the non-adherent bacteria. Then, antimicrobial(s) in BHIG were added, and the plate was incubated again for 24 h. Each well was washed twice with BHIG and fixed with 2.5% of glutaraldehyde at room temperature for one hour. The biofilms were dehydrated with a graded series of ethanol solutions (50%, 70%, 80%, 95%, 100%) followed by drying with graded hexamethyldisilazane (50%, 100%) in ethanol. Before mounting on stubs and sputter-coated with 20 nm gold, the samples were further air-dried for an additional 2 days. SEM images were taken with the Zeiss Sigma Field Emission SEM (Carl Zeiss, Ontario, Calif.) at 5 kV.

Statistical Analysis

Each experiment was repeated at least three times, in duplicate. The error bars in the provided figures represent the standard deviation of each experiment's data. All calculations were performed in Microsoft Excel and then the statistical analysis was re-shaped with SigmaPlot 11.0 (Systat Software Inc., Chicago, Ill., USA). The Student's t-test ($P \leq 0.01$ and $P \leq 0.05$) was also calculated with SigmaPlot.

Results

CAms Effectively Inhibit Planktonic Cells of BV-Associated Pathogens but not Lactobacilli The antimicrobial potential of CAms against planktonic G. vaginalis was determined and compared to their activity on healthy vaginal lactobacilli. The results illustrated that G10 compounds were more active as compared to G8 ether and ester (Table 1). The MICs of CAms against G. vaginalis were lower than their MICs against two lactobacilli with significant differences (p<0.05) for G10 compounds. However, no significant difference was detected between the susceptibility of G. vaginalis and L. gasseri to both compounds (Table 1).

TABLE 1

MICs of CAms (μM) with varying linker type (ether/ester), length (G8/G10) against G. vaginalis in comparison to healthy Lactobacillus species.

| Microorganisms | G8 ether | G8 ester | P value G8 G. vaginalis vs lactobacilli | G10 ether | G10 ester | P value G10 G. vaginalis vs lactobacilli |
|---|---|---|---|---|---|---|
| G. vaginalis | 2.5 | 24.4 | | 1.1 | 2.3 | |
| L. rhamnosus | 28.4 | 111.6 | P > 0.05 (0.15958) | 13.3 | 12.7 | P < 0.05 (0.00175) |
| L. plantarum | 11 | 223 | P ≤ 0.05 (0.04975) | 25.7 | 33.3 | P < 0.05 (0.00931) |
| L. gasseri | 11.1 | 55.9 | P > 0.05 (0.25285) | 4.4 | 12.7 | P > 0.05 (0.12197) |

Since G. vaginalis is not the sole bacterial cause of BV, CAms were evaluated against the most common isolated BV-associated pathogens: M. curtisii, Pep. anaerobius, and P. bivia. Pep. anaerobius was more susceptible to CAms as compared to M curtisii and P. bivia and again, G10 ether and ester were more active against selected pathogens than G8 compounds (Table 2). The results showed that MICs of G10 CAms against three tested pathogens were significantly lower than their MICs against L. plantarum and L. rhamnosus (P<0.01), while no significant differences were identified when G8 compounds were used against the pathogens.

TABLE 2

MICs of CAms (μM) against vaginal pathogens other than G. vaginalis.

| CAms | P. bivia | M. curtisii | Pep. anaerobius |
|---|---|---|---|
| G8 ether | 28.4 | 28.4 | 3.6 |
| G8 ester | 111.6 | 93.1 | 13.9 |
| G10 ether | 6.6 | 5.4 | 1.6 |
| G10 ester | 6.3 | 6.3 | 3.1 |

MICs and Sub-MICs of CAms Inhibit G. vaginalis Biofilm Formation

Figure 7A:
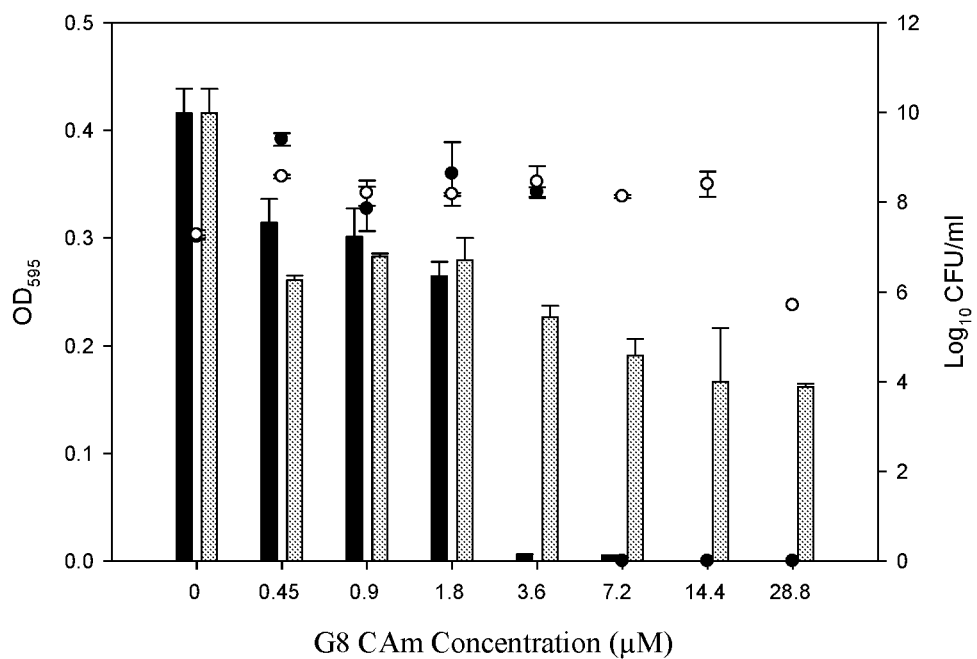
FIGS. 7A-B. Minimum biofilm inhibitory concentration (MIC-B) of (FIG. 7A) G8 compounds and (FIG. 7B) G10 compounds (μM) against *G. vaginalis* biofilm. Biofilm formation (■) and bacterial growth (●) after treatment with G8/G10 ether. Biofilm formation (▨) and bacterial growth (○) after treatment with G8/G10 ester.
Figure 7B:
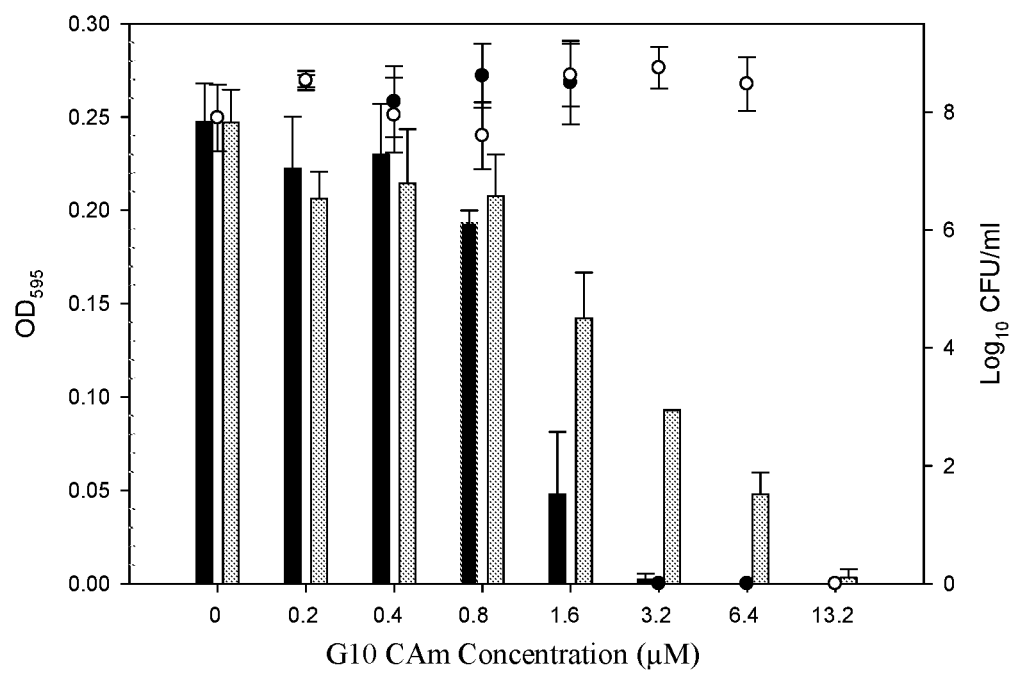

The anti-biofilm activity of CAms was evaluated in vitro against BV-associated G. vaginalis using 96-well tissue culture microplate (FIGS. 7A-B). The MIC-B value of G8 (FIG. 7A) and G10 (FIG. 7B) ethers were within their MIC ranges: 3.6 μM of G8 ether was required to inhibit >90% of biofilm formation, 1.6 μM of G10 ether and 3.2 μM of G10 ester prevented >50% of biofilm formation compared to the untreated control. G8 ester showed a 50% biofilm inhibition when the sub-MIC concentration of 7.2 μM was used. Interestingly, MIC-$B_{50}$ or MIC-$B_{90}$ of the CAms did not influence the growth of bacterial cells.

Figure 8A:
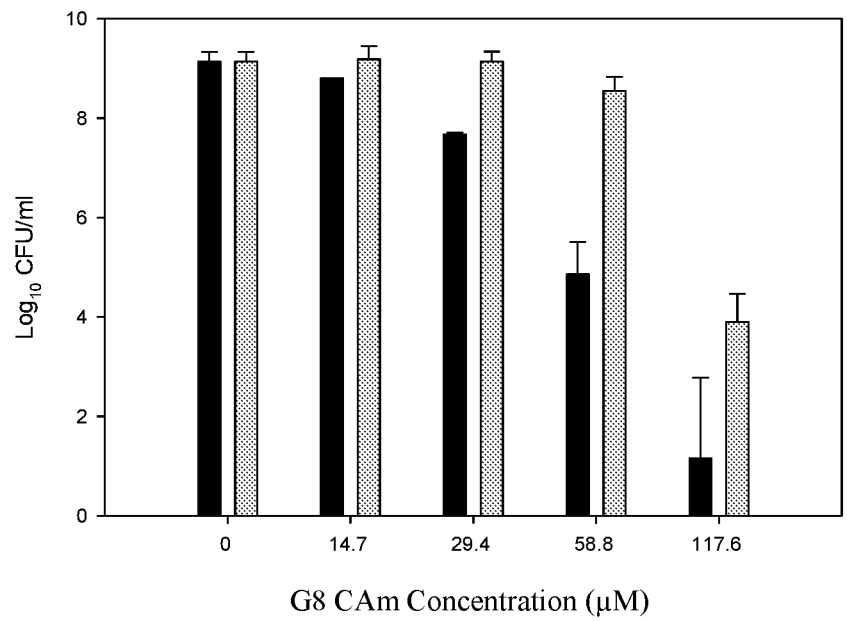
FIGS. 8A-B. Minimum biofilm bactericidal concentration (MIC-B) of (FIG. 8A) G8 compounds (μM) and (FIG. 8B) G10 compounds against preformed biofilm of *G. vaginalis*. $Log_{10}$ CFU/ml of biofilm cells (■) after treatment with G8/G10 ether. $Log_{10}$ CFU/ml of biofilm cells (▨) after treatment with G8/G10 ester.
Figure 8B:
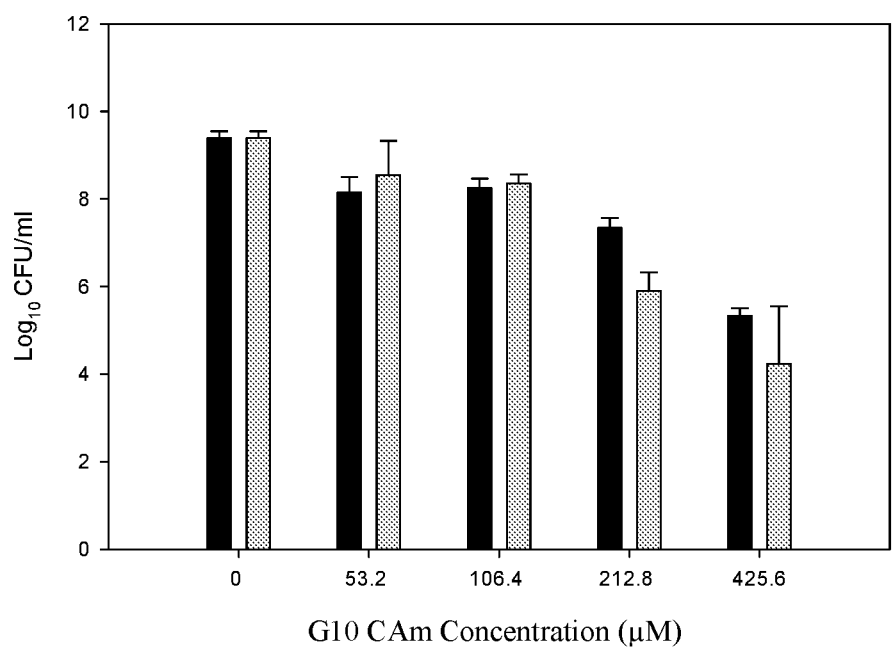
Figure 9A:
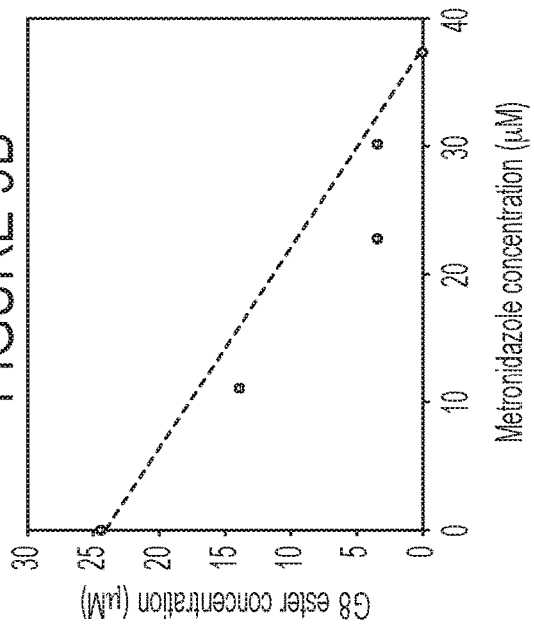
FIGS. 9A-D. Combination of metronidazole with CAms against planktonic cells of *G. vaginalis*. Combination of metronidazole with G8 ether (FIG. 9A), with G8 ester (FIG. 9B), with G10 ether (FIG. 9C) and with G10 ester (FIG. 9D).
Figure 9B:
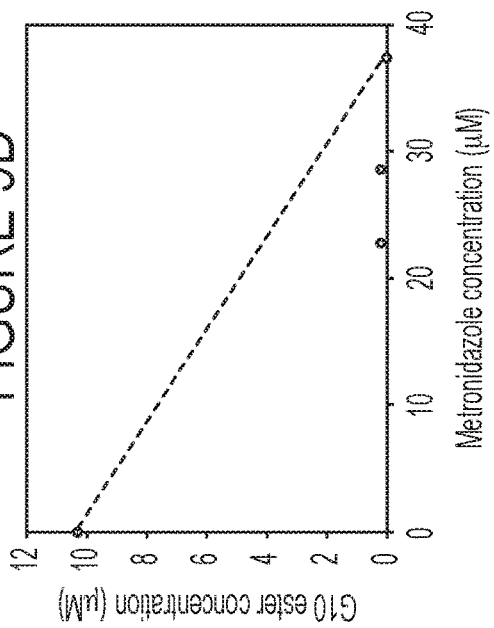
Figure 9C:
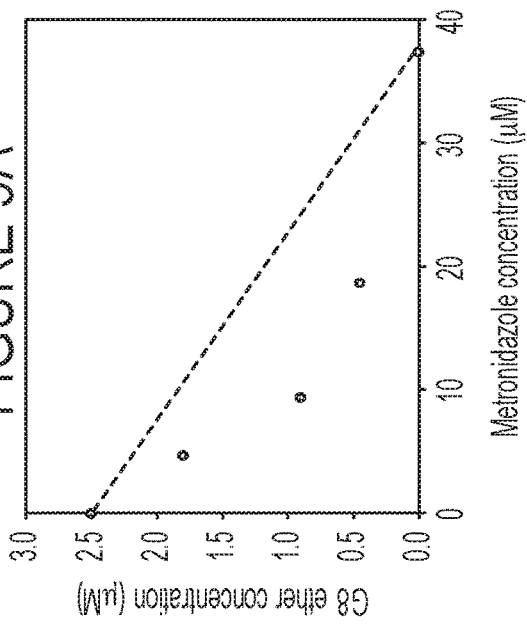
Figure 9D:
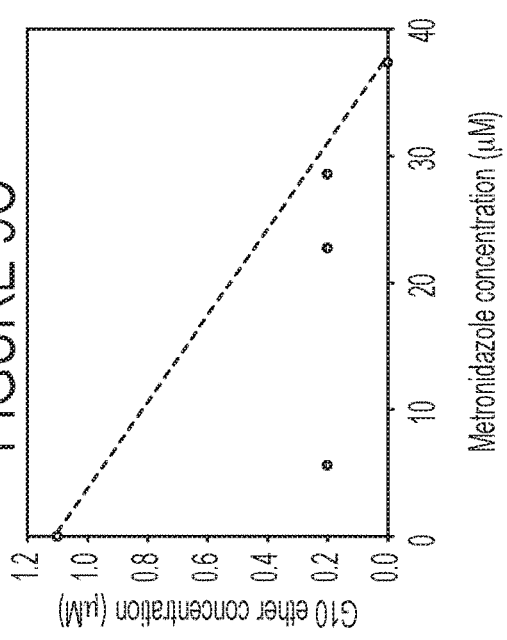

Lactobacilli Biofilms are Tolerant to CAm Concentrations which are Bactericidal for G. vaginalis Biofilms Despite being less active against planktonic G. vaginalis cells, G8 compounds were more active than G10 compounds when tested against the pre-formed biofilms (FIGS. 8A-B). Specifically, G10 ether and ester have an MBC-B of 425.6 μM against biofilm-associated G. vaginalis (FIG. 8B). At the same time, only 58.8 μM of G8 ether and 117.6 μM of G8 ester were sufficient to produce >3 log reduction in the number of the biofilm-associated pathogen (FIG. 8A). The CAms' effectiveness on biofilms of the studied *Lactobacillus* species was evaluated and compared to the bactericidal activity on *G. vaginalis* biofilm. Data showed that the MBC-Bs of CAms against the *G. vaginalis* biofilm were less than their MBC-Bs against all of the tested *Lactobacillus* species with significant differences (P<0.01, Table 3).

TABLE 3

Minimum biofilm bactericidal concentrations (MBC-B) of CAms (μM) against cells of *G. vaginalis* in comparison to *Lactobacillus* species.

| Microorganisms | G8 ether | G8 ester | G10 ether | G10 ester | P value *G. vaginalis* vs *lactobacilli* |
|---|---|---|---|---|---|
| *G. vaginalis* | 58.8 | 117.6 | 425.6 | 425.6 | |
| *L. rhamnosus* | 940 | >890 | >850 | >810 | P < 0.01 |
| *L. plantarum* | 940 | >890 | >850 | >810 | P < 0.01 |
| *L. gasseri* | 940 | >890 | >850 | 810 | P < 0.01 |

CAms Synergized with Metronidazole Against Planktonic Cells and Biofilms of *G. vaginalis*

According to our results (FIGS. 9A-D and 10A-D), the CAms' ethers and esters synergized with metronidazole against planktonic cells and biofilms of *G. vaginalis*. It was noticed that metronidazole inhibited the growth of planktonic cells of *G. vaginalis* at an MIC of 37.4 μM, which was much lower than the concentration that inhibited the growth of vaginal lactobacilli (>1168.5 μM). The MIC of G8 ether, in combination with metronidazole, decreased more than fivefold from when it was used alone (0.45 μM in combination instead of 2.5 μM when it was used alone). Regarding biofilm inhibition, the MBC-B of G8 ether, in combination with metronidazole, decreased more than three-fold from when it was used alone (11.1 μM in combination instead of 40.4 μM when it was used alone). Overall, when used in combination with the tested CAms, metronidazole's MIC against planktonic cells was more than seven-fold lower and its MIC against biofilms of *G. vaginalis* was about three-fold lower than the corresponding values for metronidazole alone (4.7 μM and 11.1 μM in combination instead of 37.4 μM and 40.4 μM for planktonic cells and biofilms, respectively). The MIC of G8 ester in combination with metronidazole decreased more than seven-fold from when it was used alone (3.4 μM in combination instead of 24.4 μM when was used alone). For *G. vaginalis* biofilm, the MBC-B of G8 ester in combination with metronidazole decreased more than three-fold from when it was used alone (26.9 μM in combination instead of 92.7 μM when was used alone). When G10 compounds were used in combination with metronidazole, the MIC of G10 decreased more than five-fold from when it was used alone (0.2 μM in combination instead of 1.1 μM when was used alone). In the same regards, the MBC-B of G10 ether, in combination with metronidazole, decreased more than 13-fold from when it was used alone (25.7 μM in combination instead of 340 μM when was used alone). Furthermore, the MIC of G10 ester in combination with metronidazole decreased fifty-fold from when it was used alone (0.2 μM in combination instead of 10 μM when was used alone). Lastly, for *G. vaginalis* biofilm, the MBC-B of G10 ester, in combination with metronidazole, decreased more than ten-fold from when it was used alone (6.3 μM in combination instead of 67.7 μM when was used alone).

Mechanism of CAMs Action Against *G. vaginalis* Biofilms

Figure 11A:
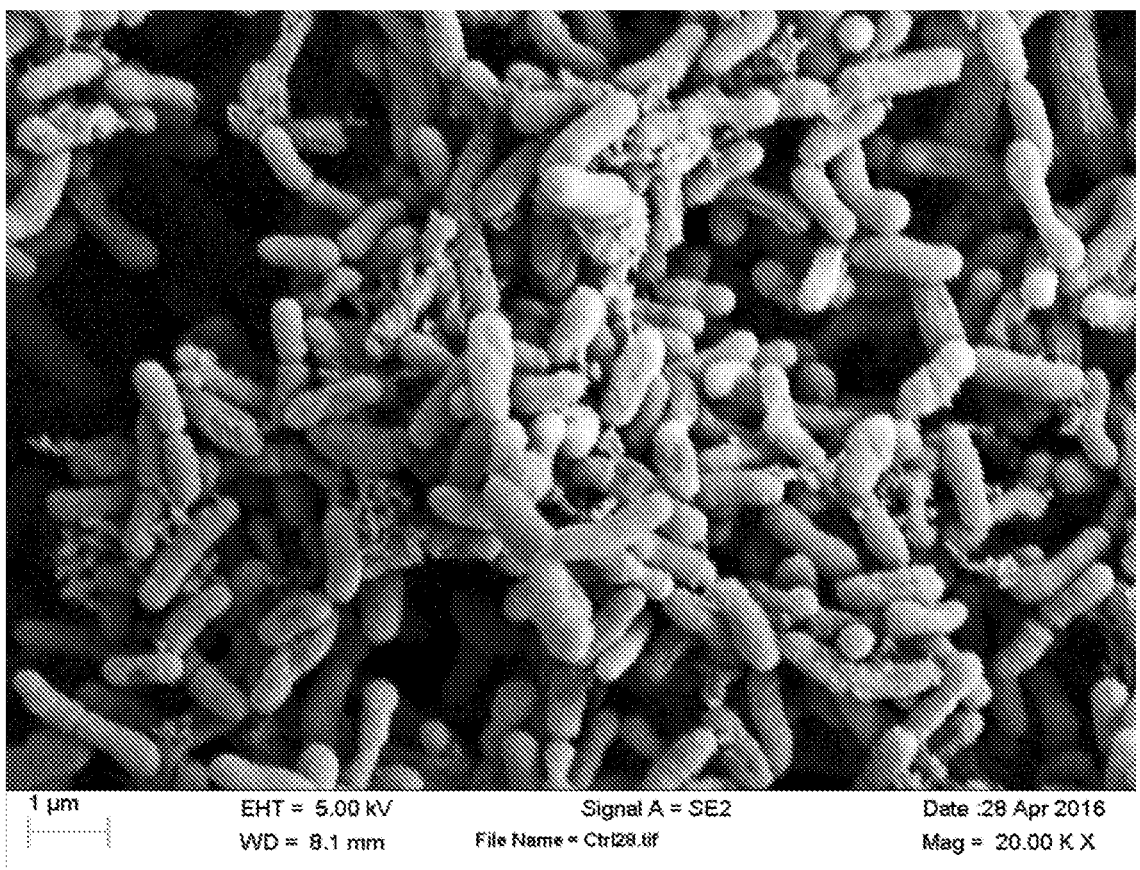
FIGS. 11A-C. Transmission electron microscopy images.
Figure 11B:
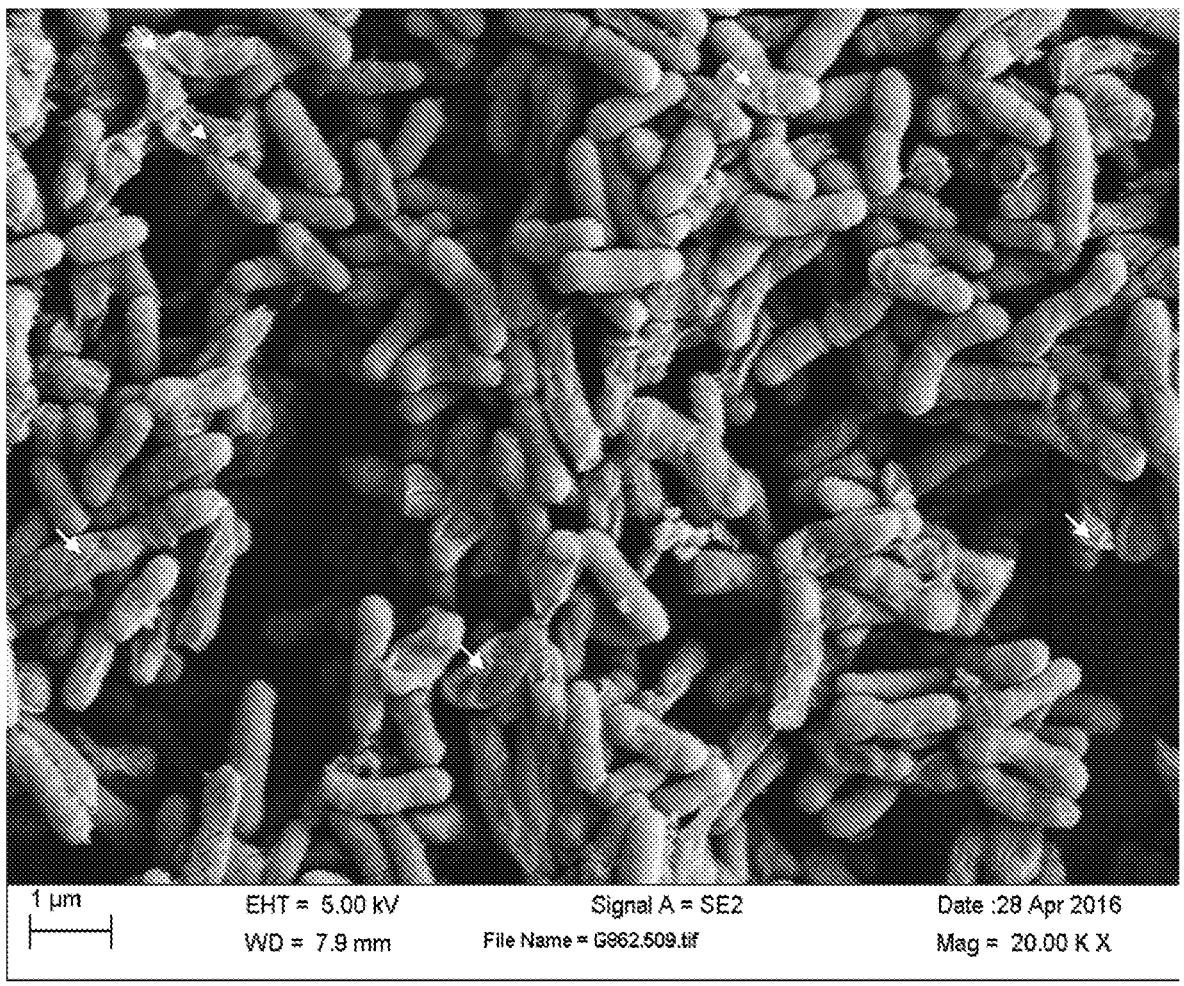
Figure 11C:
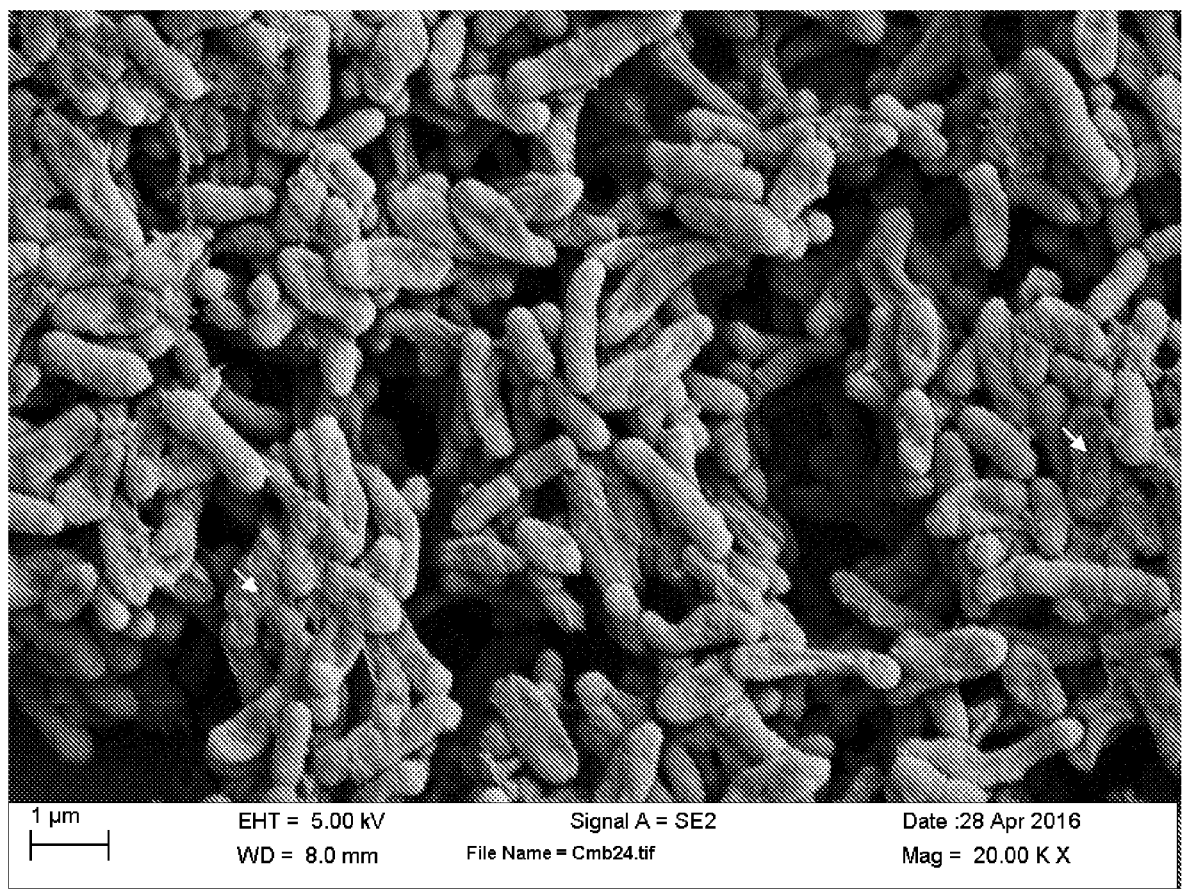

To confirm the hypothesis of CAms acting as membrane-targeting compounds, biofilm-associated *G. vaginalis* was treated with G8 antimicrobial alone at its MBC-B, and in combination with metronidazole. Scanning electron microscopy indicated considerable morphological and ultrastructural changes of treated biofilm cells as compared to untreated cells (control) (FIGS. 11A-C). Prior to treatment with CAms, *G. vaginalis* cells within the biofilm showed a cocco-bacilli shape and smooth surfaces (FIG. 11A). On the contrary, open holes, deep craters, severe membrane deformation and cellular debris were noticed within the treated sample, indicating strong evidence of membrane disruption and damage (FIG. 11B), with fragmentation also observed in the polar regions of the biofilm cells. In addition, degradation and deformation of biofilm exopolysaccharide (EPS) structures were seen as well. A combination of G8 ether and metronidazole was used against a biofilm of *G. vaginalis* (FIG. 11C); much greater killing activity, in addition to EPS reduction, was observed, indicating the importance of antimicrobial combinations for successful eradication of a biofilm and its biomass.

Discussion

Traditional antibiotics are falling short when it comes to effectively treating bacterial infections. Biofilm-associated infections have become increasingly resistant to antibiotics, often resulting in recurrence that can lead to severe health consequences. Thus, there is an urgent need for alternative medications and treatment strategies. Bacterial vaginosis is one such infection that is often resistant to conventional antibiotics, primarily metronidazole (Eschenbach D A. 2007. Clin Infect Dis 44:220-221). The infection arises from a decrease in commensal lactobacilli and an increase in anaerobic pathogenic species, predominantly *G. vaginalis*, which is often the main causative agent of BV (Hardy et al., 2015. PloS One 10: e0136658). Recurrence of bacterial vaginosis is common within three to twelve months, often due to failure of treatment with conventional antibiotics and therefore failed eradication and/or regrowth of pathogenic bacteria (Eschenbach D A. 2007. Clin Infect Dis 44:220-221). In this study, cationic amphiphilic molecules (CAms) were used to control biofilm formation of BV-associated *G. vaginalis*. Since bacterial vaginosis is a polymicrobial infection, CAms were evaluated against the most frequently isolated BV anaerobes including *M. curtisii*, *P. bivia*, and *Peptostreptococcus anaerobious*. The CAms were also evaluated against *Lactobacillus* species in order to observe the possible effect of CAms on the commensal bacteria, which are responsible for the stability and health of the vaginal flora (e.g. 49).

Biofilm-associated BV is characterized by the overgrowth of opportunistic, pathogenic bacteria, such as *G. vaginalis*, *P. bivia*, *Peptostreptococcus anaerobis*, and *M. curtisii*; all four pathogens have shown increasing resistance to conventional antibiotics (Nagaraja P. 2008. Indian J Med Microbiol 26:155). When evaluated against the pathogens, the most effective CAms were the ether compounds, particularly G10 ether. As shown in Table 1, G10 ether had the lowest MIC out of the evaluated CAms against each pathogen. When evaluated for biofilm inhibition of *G. vaginalis*, G10 ether at 1.6 μM was quite effective (FIG. 7B). as was G8 ether at 3.6 μM (FIG. 7A). Overall, it was observed that *Pep. anaerobius* was the most sensitive out of the tested BV-associated pathogens, and *P. bivia* and *M. curtisii* were more resistant to the highest concentrations of each CAm (Table 1). The CAms used in this study (FIG. 6) consisted of hydrophilic head groups and non-polar domains on opposite ends of the amphiphile's backbone, resulting in a facially amphiphilic conformation (Zhang et al., 2017. Nanomedicine: NBM 13:343-352). CAms' mode of action against the persistent pathogens, by insertion and disruption of the cytoplasmic membrane, makes them efficient as antibacterial agents (Findlay et al., 2010. Antimicrob Agents Chemother 54:4049-4058). CAms have been found to be more effective against Gram-positive bacteria, in contrast to Gram-negative organisms (Zhang et al., 2017. Nanomedicine: NBM 13:343-352). Compared to G. vaginalis and Pep. anaerobius, the higher MIC values of P. bivia and M. curtisii can be attributed to the existence of an additional lipopolysaccharide (LPS) layer in the Gram-negative organisms; the extra LPS layer forms a hydrophilic barrier, preventing the hydrophobic CAms from docking on the cytoplasmic membrane (Zhang et al., 2017. Nanomedicine: NBM 13:343-352). Resistance of M. curtisii to antibiotics, such as metronidazole and clindamycin was reported in some studies (Spiegel C A. 1987. Antimicrob Agents Chemother 31:249-252, Meltzer et al., 2008. Sex Transm Dis 35:611-613). It was suggested that 67.9% of BV recurrence is due to M. curtisii, which is frequently isolated from recurrent infections after initial treatment. M. curtisii, P. bivia and Pep. anaerobius co-exist with G. vaginalis to form a thick and adherent multispecies biofilm, as reported recently (Algburi et al., 2015. Path Dis 73(5), Turovskiy et al., 2012. Infect Dis Obstet Gynecol 2012:284762, Martin et al., 1999. J Infect Dis 180:1863-1868, Delcour et al., 1999. Antonie Van Leeuwenhoek 76:159-184). G. vaginalis is often classified as a Gram-variable bacterium, meaning it exhibits characteristics of both Gram-positive and Gram-negative bacteria. The thickness of its peptidoglycan layer varies depending on which phase the cell is at. G. vaginalis's cell wall exhibits Gram-positive characteristics in its early exponential phase, but as its life cycle advances, the peptidoglycan layer decreases in thickness and, the cell stains as a Gram-negative bacteria. Overall, cationic amphiphiles have shown to be quite effective against anaerobes: in Sovadinova et al. (Sovadinova et al., 2011. Polymers 3:1512-1532), antimicrobial peptide-mimetic amphiphilic polymethacrylate derivatives were evaluated against the anaerobe Propionibacterium acnes and were found to be highly effective in eradicating the bacterium. In Algburi et al. (Algburi et al., 2015. Path Dis 73(5)), the natural antimicrobials subtilosin and lauramide arginine ethyl ester (LAE) were evaluated against G. vaginalis as well. The cationic LAE altered the permeability of the cytoplasmic membrane, and was shown to further enhance the antibiotic susceptibility of the bacterial cells, as did subtilosin A without bactericidal effects on the healthy vaginal lactobacilli (Algburi et al., 2015. Path Dis 73(5)).

Lactobacilli are crucial to the stability and health of the vaginal microenvironment; they play a pivotal role in controlling the pH, which allows for inhibition of overgrowth of opportunistic pathogenic bacteria (Martin et al., 1999. J Infect Dis 180:1863-1868). Most studies that evaluate an antimicrobial agent against pathogenic bacteria often neglect the effect of the agent on the protective microbiota. The CAms used in this study were evaluated against three species of Lactobacillus: L. rhamnosus, L. plantarum, and L. gasseri. The most effective CAm on G. vaginalis, G10 ether, had much less effect on the Lactobacillus species, L. plantarum and L. rhamnosus especially. Resistance of lactobacilli strains to antibiotics is either acquired due to chromosomal mutation(s) or intrinsic mutations, which occur when lactobacilli replace their surface properties, such as replacing a D-alanine residue in the bacterial cell wall with D-lactate or D-serine, preventing vancomycin binding (Delcour et al., 1999. Antonie Van Leeuwenhoek 76:159-184) and in return, becoming resistant to vancomycin. Horizontal transfer of antibiotic resistance genes and presence of a variety of atypical antibiotic resistance genes such as chloramphenicol macrolides, lincosamides, and streptogramins (MLS) (van Hoek et al., 2008. Int J Antimicrob Agents 31:544-548) and different tetracycline resistance genes (Ammor et al., 2008. Appl Environ Microbiol 74:1394-1401) play a key role in lactobacilli resistance to antibiotics. Furthermore, all lactobacilli have been identified to have multidrug resistance (MDR) transporters (see review of Gueimonde et al. (Gueimonde et al., 2009. Int J Probiotics Prebiotics 4: 181-186)). Bile resistance in L. reuteri (Whitehead et al., 2008. Appl Environ Microbiol 74:1812-1819) was related to the role of MDR systems indicating the importance of such system in environmental stressors. Overall, it was observed that the MIC values of CAms for each species of Lactobacillus were significantly greater than those of G. vaginalis, leading us to propose that the CAms could be selectively targeting pathogens while having little or no effect on the protective microbiota.

Most often, persistent infections arise from bacterial biofilms rather than solely planktonic cells (Di Luca et al., 2014. Pathog Dis 70:257-270). Biofilms consist of a multitude of microbial cells that are associated with a surface and enclosed in a matrix consisting of extracellular polymeric substances (EPS), which often contributes to the antimicrobial-resistance properties of biofilms (Donlan R M. 2002. Emerg Infect Diseases 8:881-890). Quorum sensing has been attributed as being the main line of communication between microbial cells in a community, allowing for the construction and/or dissolution of a biofilm (Parsek M R, Greenberg E. 2005. Trends Microbiol 13:27-33). It has been demonstrated that prevention of biofilm formation is more effective than treatment of a biofilm, which includes prevention of bacterial attachment and/or communication, or by changing the attached-surface properties, as demonstrated by Shah et al. (Shah et al. 2013. Materials Today 16:177-182). Preventing biofilm formation can help lower the required antimicrobial concentration due to the easier targeting of bacterial cells while overall preventing antibiotic resistance stemming from microbial mutations. In our study, we observed that the biofilms of G. vaginalis were inhibited at the sub-MIC of CAms without influencing bacterial growth (FIGS. 7A and 7B). One possible explanation for this occurrence can be the interruption of quorum sensing by the CAms. Fuente-Núñex et al. reported that the small synthetic cationic peptide 1037 significantly affected the swarming motility (depends on flagellin and quorum sensing) of bacterial cells and inhibited biofilm formation (Fuente-Nunez et al., 2012. Antimicrob Agents Chemother 56:2696-2704). We tested the sub-minimum inhibitory concentrations (sub-MIC) of the four most promising compounds for their ability to inhibit quorum sensing. The Fe(III) reduction assay was utilized to evaluate all four compounds as quorum sensing inhibitors in Gram-positive bacteria. In Gram-negative bacteria, these four compounds were evaluated as quorum sensing inhibitors using Chromobacterium voilaceum as a microbial reporter (Algburi, et al., 2016. Probiotics Antimicrob Proteins, doi:10.1007/s12602-016-9242-x). As a result of these experiments, no quorum sensing inhibition was observed in either Gram-positive or Gram-negative bacteria by any of the four compounds. Consequently, we speculate that there are possibly different mechanisms involved in the interactions of these compounds with bacterial cells.

Another possible explanation can be that the CAms with sub-MICs coated the attachment surface, preventing the bacterial cells from gathering on the surface and therefore creating an inability to form a biofilm. Segev-Zarko et al. (Segev-Zarko et al., 2015. Biochem J 468:259-270) demonstrated AMPs's' ability to reduce bacterial adhesion to surfaces and inhibit biofilm formation, due to the AMPs' capability of coating either the surface of a biomaterial or the bacterium itself. The findings of Beckloff et al. (Beckloff et al., 2007. Antimicrob Agents Chemother 51:4125-4132) seem to conflict with this observation. The AMP mimetic used in their study, meta-phenylene ethynylene (mPE), required a very high concentration, nearly forty times the strength of the concentration needed to eradicate a biofilm of *Staphylococcus aureus*, in order to inhibit the biofilm.

Overall, the MIC-B of CAms against *G. vaginalis* were lower than the MIC values against the *Lactobacillus* species, reinforcing the observation that the CAms seem to be selectively targeting the pathogenic cells rather than the microorganisms of the healthy commensal microbiota.

Biofilm bactericidal activity of CAms was evaluated against pre-formed biofilms of *G. vaginalis* as well as *Lactobacillus* species. Unlike their activity against planktonic cells, G8 compounds were more effective against biofilm of *G. vaginalis* and *Lactobacillus* strains compared to G10 compounds. In addition, the highly hydrophobic compounds perhaps aggregate and stock in the biofilm matrix, delaying the delivery of antimicrobial to the biofilm associated cells. Findlay et al. (Findlay et al., 2010. Antimicrob Agents Chemother 54:4049-4058) found that shorter chain Arg-X-Arg peptide is highly active and able to penetrate biofilms. More studies are required to confirm that when lesser hydrophobic chains peptides are used, increased bactericidal activity is observed.

All of the *Lactobacillus* biofilms were significantly more tolerant to CAms as compared to the pathogenic biofilm of *G. vaginalis*. It is important for the health of the vaginal microbiota that lactobacilli biofilms are kept intact and are tolerant to antimicrobials. *Lactobacillus* species ferment glycogen secreted by vaginal epithelial cells into lactic acid, which controls the microenvironment of the vagina by maintaining a low pH and preventing an overgrowth of pathogens (Dover S E, et al., 2008. Int J Probiotics Prebiotics 3:219-230). Biofilm formation by protective bacteria, such as lactobacilli, enhances their beneficial properties and promotes their antimicrobial potential. Jones and Versalovic (Jones S E, Versalovic J. 2009. BMC Microbiol 9:1-9) reported a promotion in cytokine and antimicrobial production by *L. reuteri* growing in a biofilm. Moreover, the biofilm of *L. reuteri* may possibly eradicate and re-occupy the biofilm of *G. vaginalis* (Saunders et al., 2007. Colloids Surf B Biointerfaces. 55:138-142), controlling pathogenic infection. Therefore, it is a crucial observation that the CAms had very little, if any, bactericidal effect on the *Lactobacillus* biofilms.

Metronidazole was used in this study because it is frequently prescribed by OB/GYN (obstetrics/gynecology) doctors for the treatment of BV (Centers for Disease Control and Prevention (CDC). 2015. *Sexually Transmitted Diseases Treatment Guidelines*, Center for Surveillance, Epidemiology, and Laboratory Services, U.S. Department of Health and Human Services. Atlanta, Ga., Sobel R, Sobel J D. 2015. Expert Opin Pharmacother 16:1109-1115). The synergistic activity of metronidazole, when combined with natural antimicrobials, enhanced its antimicrobial potential (Algburi et al., 2015. Path Dis 73(5)). In this study, the nature of interactions between metronidazole and CAms against *G. vaginalis*, planktonic and biofilm cells, were investigated using isobolograms: all CAms synergized with metronidazole against *G. vaginalis*. Compared to other combinations, G10 ester more effectively synergized with metronidazole, reducing the required concentrations of each of the combined antimicrobials to kill the planktonic cells and biofilm cells. Synergism of two or more antimicrobials can be beneficial for the efficacy of each antimicrobial while lowering the risk of antimicrobial resistance, especially if the antimicrobials each have different modes of action (Rybak M J, Mcgrath B J. 1996. Drugs 52:390-405). Using natural or novel antimicrobials either alone or in combination with conventional antibiotics allows avoidance of consequences that come with the use of conventional antibiotics alone (Algburi et al., 2015. Path Dis 73(5)). The National Institute of Health has taken a new approach over the past few years in combating antibiotic resistance by combining conventional antibiotic treatments with complementary methods, i.e. natural antimicrobials, to determine if there is possible success with the use of natural products (National Center for Complementary and Integrative Health (NCCIH). 2014. Frequently Asked Questions: Name Change. nccih.nih.gov/news/name-change-faq. Accessed 5 Oct. 2016). As seen in the resulting isobolograms, metronidazole was synergized with each of the CAms against *G. vaginalis*; $G_{10}$ compounds were most strongly synergized with metronidazole. The higher the CAm concentration, the lower the metronidazole concentration needed for effective inhibition of *G. vaginalis*.

The SEM data (this study), together with Zhang et al. (Zhang et al., 2017. Nanomedicine: NBM 13:343-352) findings, suggest that the antimicrobial action of CAms is associated with the disruption of cellular membrane permeability, ultimately reducing the opportunity of bacterial resistance. These promising results could potentially lead to a decrease in conventional antibiotic use when treating bacterial vaginosis, therefore, decreasing the risk for antibiotic-resistant infections.

CONCLUSION

Antibiotic resistance of persistent infections is an important challenge which requires significant attention to find alternative antimicrobials. Here, we reported on the synthesized cationic amphiphiles (CAms) having antimicrobial and anti-biofilm activity against BV-associated pathogens. The structure of CAms can be modified and their biocidal potential improved to counteract resistance to antibiotics. CAms have effectively prevented and eradicated biofilms of *G. vaginalis* with small concentrations at M ranges without any harmful effects on the protective vaginal microbiota. In addition, CAms have shown synergistic activity when combined with metronidazole against planktonic cells and biofilm cells of *G. vaginalis*. With this, along with no resulting cytotoxicity on human cells or disruption of cellular membranes at or below MICs, in addition to selectively eradicating pathogenic biofilms and synergistically acting with traditionally prescribed antibiotics, CAms are a promising new generation of antimicrobials with the potential to transform modern therapeutic strategies of bacterial vaginosis.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I:

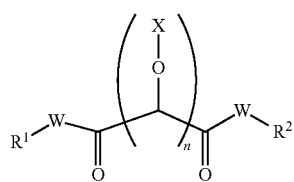

wherein:
R$^1$ is a polyether or a (C$_1$-C$_6$)alkyl that is substituted with one or more NR$_a$R$_b$;
R$^2$ is a polyether or a (C$_1$-C$_6$)alkyl that is substituted with one or more NR$_a$R$_b$;
each W is independently —NH—, —O— or —S—;
each X is independently (C$_4$-C$_{14}$)alkyl;
each R$_a$ is independently H or (C$_1$-C$_6$)alkyl;
each R$_b$ is independently H, (C$_1$-C$_6$)alkyl or —C(=NH)NH$_2$; and
n is 1, 2, 3, 4, 5, 6, 7, or 8;
or a salt thereof.

2. A compound of formula II:

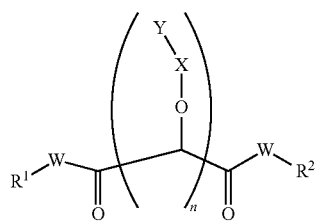

wherein:
R$^1$ is a polyether or a (C$_1$-C$_6$)alkyl that is optionally substituted with one or more NR$_a$R$_b$;
R$^2$ is a polyether or a (C$_1$-C$_6$)alkyl that is optionally substituted with one or more NR$_a$R$_b$;
each W is independently —NH—, —O— or —S—;
each X is independently (C$_2$-C$_{20}$)alkyl;
R$_a$ and R$_b$ are each independently H or (C$_1$-C$_6$)alkyl;
each Y is independently —NH$_2$, —N$^+$(R$^c$)$_3$Z$^-$, —NH—C(=NH)—NH$_2$ or NH—BOC;
each R$^c$ is independently (C$_1$-C$_6$)alkyl;
Z$^-$ is a counter ion; and
n is 1, 2, 3, 4, 5, 6, 7, or 8;
or a salt thereof.

3. The compound or salt of claim 1, wherein R$^1$ is (C$_1$-C$_6$)alkyl substituted with one or more NR$_a$R$_b$.

4. The compound or salt of claim 3 wherein R$^1$ is methyl, ethyl, propyl, isopropyl, butyl, isobutyl, or sec-butyl, substituted with one or more NR$_a$R$_b$.

5. The compound or salt of claim 1, wherein R$^2$ is a (C$_1$-C$_6$)alkyl that is substituted with one or more NR$_a$R$_b$.

6. The compound or salt of claim 5 wherein R$^2$ is methyl, ethyl, propyl, isopropyl, butyl, isobutyl, or sec-butyl, substituted with one or more NR$_a$R$_b$.

7. The compound or salt of claim 1, wherein each X is independently (C$_4$-C$_{12}$)alkyl.

8. The compound or salt of claim 1, wherein each X is independently (C$_{10}$)alkyl.

9. The compound or salt of claim 1, wherein each X is independently (C$_{12}$)alkyl.

10. The compound or salt of claim 1, wherein each W is independently —NH—.

11. The compound or salt of claim 1, wherein n is 2.

12. The compound or salt of claim 1 which is a compound of formula (Id):

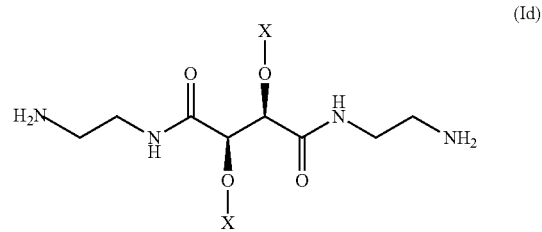

or a salt thereof.

13. The compound or salt of claim 1 which is selected from the group consisting of:

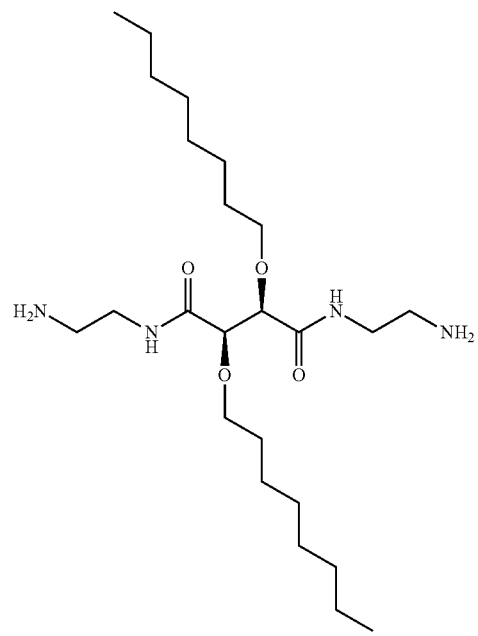

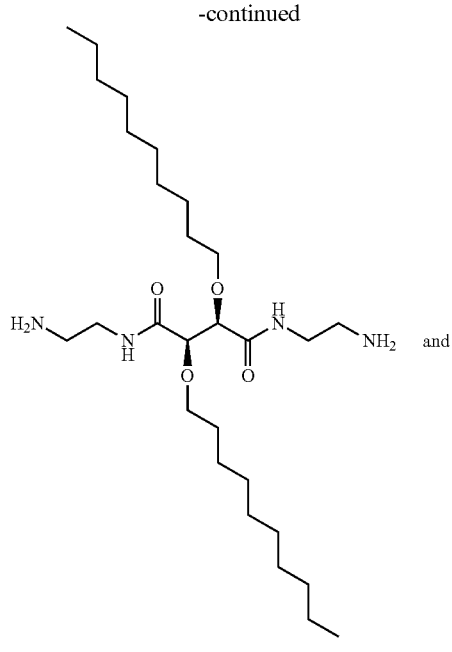
and
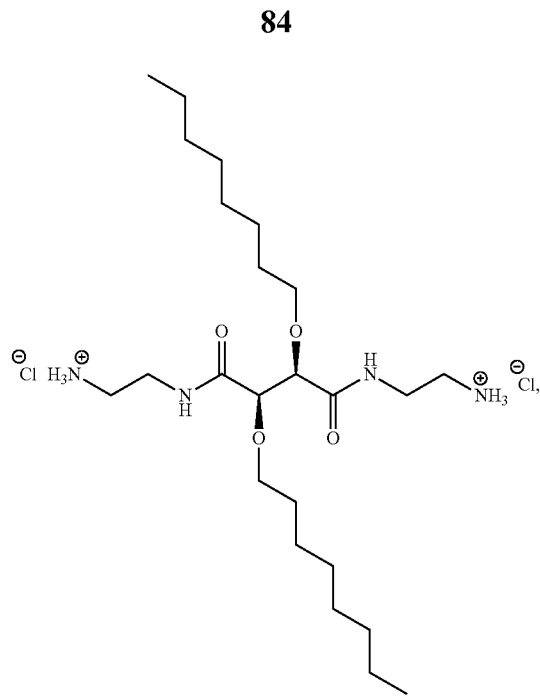
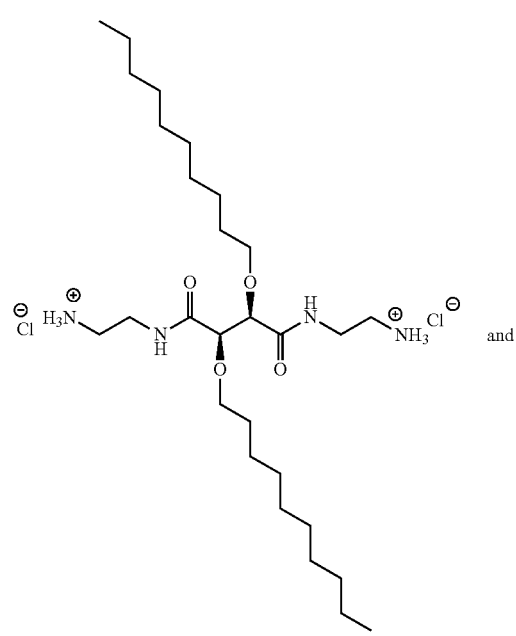
and
and salts thereof.
14. The salt of claim 1 which is selected from the group consisting of:

-continued

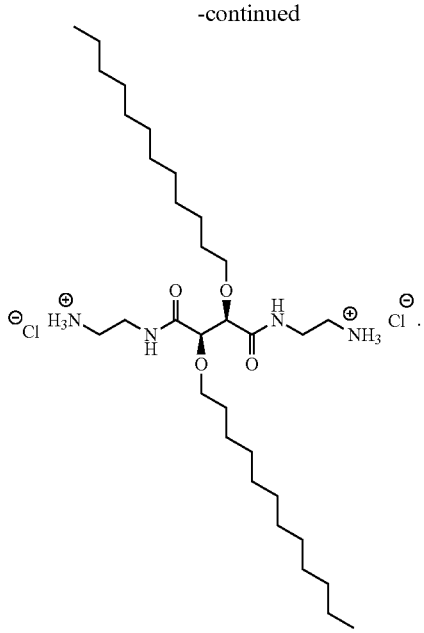

15. A pharmaceutical composition comprising a compound as described in claim 1, or a pharmaceutically acceptable salt thereof, and a pharmaceutically acceptable carrier.

16. A method for treating a bacterial infection in a mammal comprising administering to the mammal an effective amount of a compound as described in claim 1, or a pharmaceutically acceptable salt thereof.

17. The method of claim 16, wherein the bacterial infection is caused by a bacterial strain selected from the group consisting of *Escherichia coli, Caulobacter crescentus, Pseudomonas aeruginosa, Agrobacterium tumefaciens, Branhamella catarrhalis, Citrobacter diversus, Enterobacter aerogenes, Enterobacter cloacae, Enterobacter sakazakii, Enterobacter asburiae, Pantoea agglomerans, Klebsiella pneumoniae, Klebsiella oxytoca, Klebsiella rhinoscleromatis, Proteus mirabilis, Salmonella typhimurium, Salmonella enteriditis, Serratia marcescens, Shigella sonnei, Neisseria gonorrhoeae, Acinetobacter baumannii, Acinetobacter calcoaceticus, Acinetobacter lwoffi, Salmonella enteriditis, Fusobacterium nucleatum, Veillonella parvula, Bacteroides forsythus, Actinobacillus actinomycetemcomitans, Aggregatibacter actinomycetemcomitans, Porphyromonas gingivalis, Helicobacter pylori, Francisella tularensis, Yersinia pestis, Borrelia burgdorferi, Neisseria meningitides, Burkholderia cepacia, Brucella neotomae, Legionella pneumophila, Y. pseudotuberculosis, Salmonella enterica serovar typhimurium, Haemophilus influenza, Staphylococcus aureus, Staphylococcus epidermidis, Staphylococcus saprophyticus, Streptococcus pyogenes, Streptococcus faecalis, Enterococcus faecalis, Enterococcus faecium, Bacillus subtilis, Micrococcus luteus, Bacillus anthracis, Bacillus cereus, Clostridium difficile, Propionibacterium acnes, Streptococcus mutans, Actinomyces viscosus, Actinomyces naeslundii, Streptococcus sanguis, Streptococcus pneumoniae, Listeria monocytogenes, Streptococcus salivarius, Gardnerella vaginalis, Peptostreptococcus anaerobius, Mobiluncus curtisii, Prevotella bivia* and *Mycobacterium tuberculosis*.

18. The method of claim 16, further comprising administering a second therapeutic agent, wherein the second therapeutic agent is an antibiotic agent selected from the group consisting of clindamycin, metronidazole and tinidazole.

19. The pharmaceutical composition of claim 15, further comprising an antibiotic agent.

20. The method of claim 16, wherein the bacterial infection is vaginosis.

21. The method of claim 16, wherein the bacterial infection is caused by *Gardnerella vaginalis, Peptostreptococcus anaerobius, Mobiluncus curtisii*, and/or *Prevotella bivia*.

22. The compound or salt of claim 2, wherein $R^1$ is a $(C_1$-$C_6)$alkyl that is optionally substituted with one or more $NR_aR_b$.

23. The compound or salt of claim 22, wherein $R^1$ is methyl, ethyl, propyl, isopropyl, butyl, isobutyl, or sec-butyl.

24. The compound or salt of claim 2, wherein $R^1$ is $(C_1$-$C_6)$alkyl substituted with one or more $NR_aR_b$.

25. The compound or salt of claim 2, wherein $R^2$ is a $(C_1$-$C_6)$alkyl that is optionally substituted with one or more $NR_aR_b$.

26. The compound or salt of claim 25, wherein $R^2$ is methyl, ethyl, propyl, isopropyl, butyl, isobutyl, or sec-butyl.

27. The compound or salt of claim 2, wherein $R^2$ is a $(C_1$-$C_6)$alkyl that is substituted with one or more $NR_aR_b$.

28. The compound or salt of claim 2, wherein each Y is independently —$NH_2$.

29. The compound or salt of claim 2, wherein each X is independently $(C_4$-$C_{12})$alkyl.

30. The compound or salt of claim 2, wherein each X is independently $(C_7)$alkyl.

31. The compound or salt of claim 2, wherein each X is independently $(C_9)$alkyl.

32. The compound or salt of claim 2, wherein each X is independently $(C_{11})$alkyl.

33. The compound or salt of claim 2, wherein each W is independently —NH—.

34. The compound or salt of claim 2, wherein n is 2.

35. The compound or salt of claim 2, which is a compound of formula (IIc'):

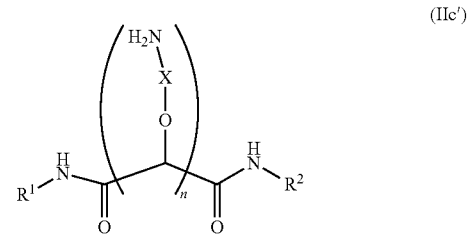

(IIc')

wherein:

$R^1$ is a polyether or a $(C_1$-$C_6)$alkyl; and $R^2$ is a polyether or a $(C_1$-$C_6)$alkyl;

or a salt thereof.

36. The compound or salt of claim 2, which is a compound of formula (IId):
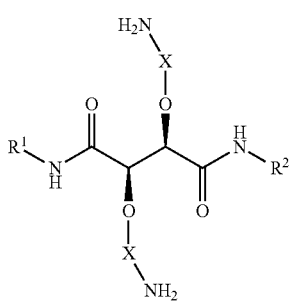
(IId)
or a salt thereof.
37. The compound or salt of claim 2, which is selected from the group consisting of:
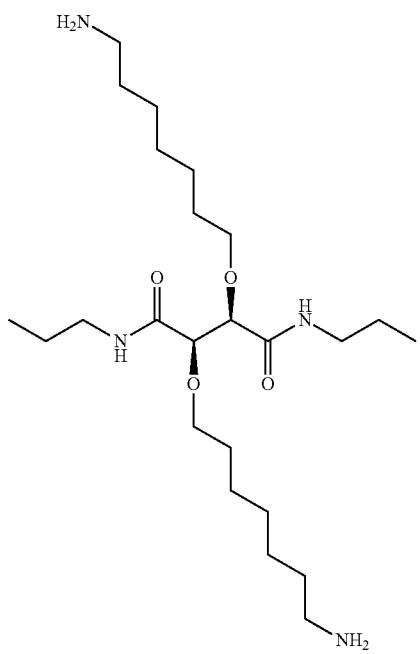
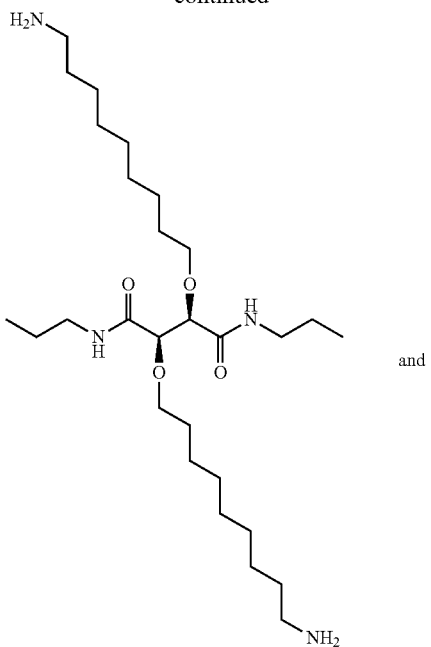
and
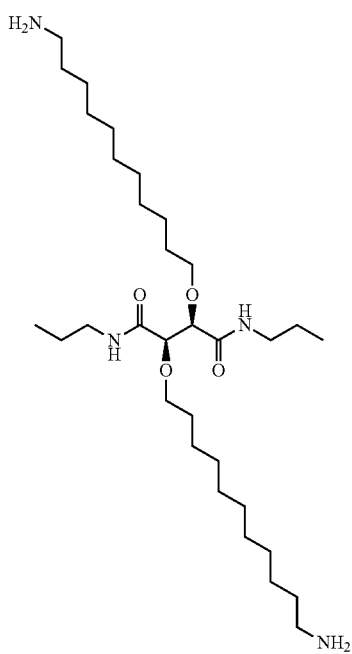 [SMILES: CCCNC(=O)[C@H](OCCCCCCCCCCCN)[C@@H](OCCCCCCCCCCCN)C(=O)NCCC]
and salts thereof.
38. The salt of claim 2, which is selected from the group consisting of:

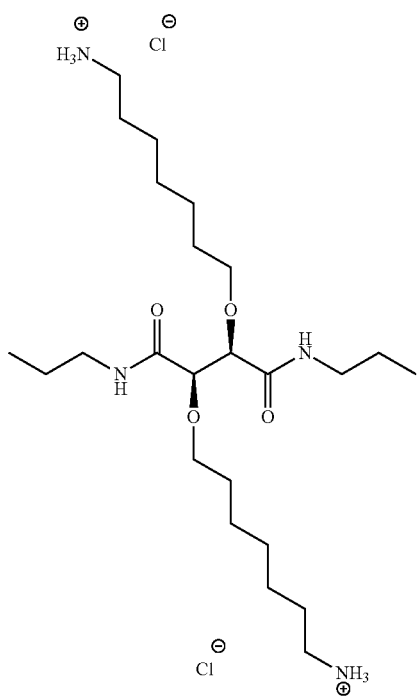

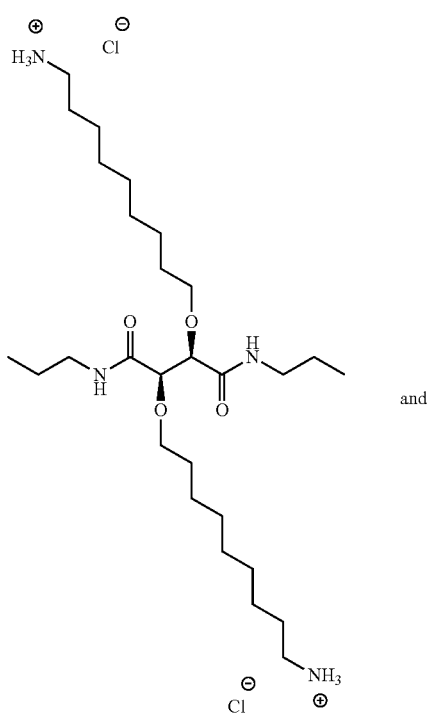

and

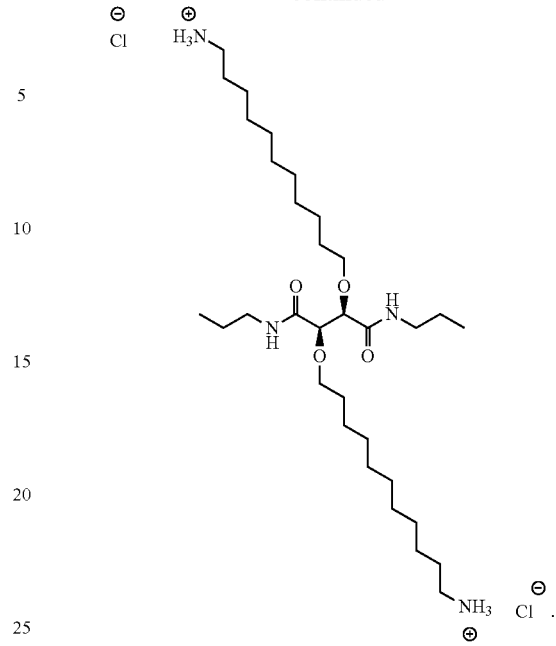

39. A pharmaceutical composition comprising a compound as described in claim 2, or a pharmaceutically acceptable salt thereof, and a pharmaceutically acceptable carrier.

40. The pharmaceutical composition of claim 39, further comprising an antibiotic agent.

41. A method for treating a bacterial infection in a mammal comprising administering to the mammal an effective amount of a compound as described in claim 2, or a pharmaceutically acceptable salt thereof.

42. The method of claim 41, wherein the bacterial infection is caused by a bacterial strain selected from the group consisting of *Escherichia coli, Caulobacter crescentus, Pseudomonas aeruginosa, Agrobacterium tumefaciens, Branhamella catarrhalis, Citrobacter diversus, Enterobacter aerogenes, Enterobacter cloacae, Enterobacter sakazakii, Enterobacter asburiae, Pantoea agglomerans, Klebsiella pneumoniae, Klebsiella oxytoca, Klebsiella rhinoscleromatis, Proteus mirabilis, Salmonella typhimurium, Salmonella enteriditis, Serratia marcescens, Shigella sonnei, Neisseria gonorrhoeae, Acinetobacter baumannii, Acinetobacter calcoaceticus, Acinetobacter lwoffi, Salmonella enteriditis, Fusobacterium nucleatum, Veillonella parvula, Bacteroides forsythus, Actinobacillus actinomycetemcomitans, Aggregatibacter actinomycetemcomitans, Porphyromonas gingivalis, Helicobacter pylori, Francisella tularensis, Yersinia pestis, Borrelia burgdorferi, Neisseria meningitides, Burkholderia cepacia, Brucella neotomae, Legionella pneumophila, Y. pseudotuberculosis, Salmonella enterica* serovar *typhimurium, Haemophilus influenza, Staphylococcus aureus, Staphylococcus epidermidis, Staphylococcus saprophyticus, Streptococcus pyogenes, Streptococcus faecalis, Enterococcus faecalis, Enterococcus faecium, Bacillus subtilis, Micrococcus luteus, Bacillus anthracis, Bacillus cereus, Clostridium difficile, Propionibacterium acnes, Streptococcus mutans, Actinomyces viscosus, Actinomyces naeslundii, Streptococcus sanguis, Streptococcus pneumoniae, Listeria monocytogenes, Streptococcus salivarius, Gardnerella vaginalis, Peptostreptococcus anaerobius, Mobiluncus curtisii, Prevotella bivia* and *Mycobacterium tuberculosis*.

43. The method of claim 41, wherein the bacterial infection is vaginosis.

44. The method of claim 41, wherein the bacterial infection is caused by *Gardnerella vaginalis, Peptostreptococcus anaerobius, Mobiluncus curtisii*, and/or *Prevotella bivia*.

45. The method of claim 41, further comprising administering a second therapeutic agent, wherein the second therapeutic agent is an antibiotic agent selected from the group consisting of clindamycin, metronidazole and tinidazole.

46. A compound of formula I:

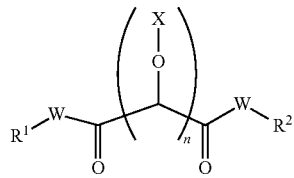

(I)

wherein:

$R^1$ is methyl, ethyl, propyl, isopropyl, butyl, isobutyl, or sec-butyl, substituted with one or more $NR_aR_b$;

$R^2$ is a polyether or a $(C_1-C_6)$alkyl that is substituted with one or more $NR_aR_b$;

each W is independently —NH—, —O— or —S—;

each X is independently $(C_1-C_{20})$alkyl;

each $R_a$ is independently H or $(C_1-C_6)$alkyl;

each $R_b$ is independently H, $(C_1-C_6)$alkyl or —C(=NH)NH$_2$; and n is 1, 2, 3, 4, 5, 6, 7, or 8;

or a salt thereof.

* * * * *